US010906943B2

(12) United States Patent
Carrillo Molina et al.

(10) Patent No.: US 10,906,943 B2
(45) Date of Patent: Feb. 2, 2021

(54) VIRUS-LIKE PARTICLES WITH HIGH-DENSITY COATING FOR INDUCING THE EXPRESSION OF ANTIBODIES

(71) Applicant: FUNDACIO PRIVADA INSTITUT DE RECERCA DE LA SIDA-CAIXA, Barcelona (ES)

(72) Inventors: Jorge Carrillo Molina, Barcelona (ES); Luis M. Molinos-Albert, Valencia (ES); Julián Miguel Blanco Arbués, Barcelona (ES)

(73) Assignee: Fundacio Privada Institut De Recerca De La Sida, Caixa (ES)

( * ) Notice: Subject to any disclaimer, the term of this patent is extended or adjusted under 35 U.S.C. 154(b) by 0 days.

(21) Appl. No.: 16/321,271

(22) PCT Filed: Jul. 26, 2017

(86) PCT No.: PCT/IB2017/001101

§ 371 (c)(1), (2) Date: Jan. 28, 2019

(87) PCT Pub. No.: WO2018/020324

PCT Pub. Date: Feb. 1, 2018

(65) Prior Publication Data

US 2019/0315807 A1 Oct. 17, 2019

(30) Foreign Application Priority Data

Jul. 27, 2016 (EP) .................................... 16382364

(51) Int. Cl.

| | |
|---|---|
| ***A61K 39/00*** | (2006.01) |
| ***A61K 39/12*** | (2006.01) |
| ***C12N 7/00*** | (2006.01) |
| ***C07K 14/005*** | (2006.01) |
| ***A61K 39/145*** | (2006.01) |
| ***A61P 31/18*** | (2006.01) |
| ***A61K 39/21*** | (2006.01) |
| ***C07K 14/705*** | (2006.01) |

(52) U.S. Cl.

CPC ............ *C07K 14/005* (2013.01); *A61K 39/21* (2013.01); *A61P 31/18* (2018.01); *C07K 14/70503* (2013.01); *C07K 14/70585* (2013.01); *C07K 14/70596* (2013.01); *A61K 2039/5258* (2013.01); *A61K 2039/545* (2013.01); *A61K 2039/6081* (2013.01); *C07K 2319/03* (2013.01); *C07K 2319/33* (2013.01); *C12N 2740/16022* (2013.01); *C12N 2740/16023* (2013.01); *C12N 2740/16034* (2013.01); *C12N 2740/16122* (2013.01); *C12N 2740/16134* (2013.01); *C12N 2740/16222* (2013.01); *C12N 2740/16234* (2013.01)

(58) Field of Classification Search

CPC ............ A61K 39/12; A61K 2039/5258; A61K 2039/545; C07K 14/005; C12N 7/00

See application file for complete search history.

(56) References Cited

U.S. PATENT DOCUMENTS

| | | |
|---|---|---|
| 4,554,101 A | 11/1985 | Hopp |
| 5,554,372 A | 9/1996 | Hunter |
| 5,643,756 A | 7/1997 | Kayman et al. |

FOREIGN PATENT DOCUMENTS

| | | |
|---|---|---|
| WO | 1997/028816 | 8/1997 |
| WO | 2012/055985 | 5/2012 |

OTHER PUBLICATIONS

Kuczowska et al. "Lactobacillus planatarum displaying CCL3 chemokine in fusion with HIV-1 Gag derived antigen causes increased recruitment of T cells", Microbial Cell Factories, 25(1), 2015: 1-12.*

Kuczkowska et al., "Lactobacillus plantarum displaying CCL3 chemokine in fusio with HIV-1 Gag derived antigen causes increased recruitment of T cells", Microbial Cell Factories, 2015, 14:1-12.*

Adachi, A. et al., "Production of Acquired Immunodeficiency Syndrome—Associated Retrovirus in Human and Nonhuman Cells Transfected with an Infectious Molecular Clone", Journal of Virology, vol. 59, No. 2, 1986, pp. 284-291.

Adler, M.W., "Range and Natural History of Infection", British Medical Journal, vol. 294, 1987, pp. 1145-1147.

Altschul, S.F. et al., "Basic Local Alignment Search Tool", J. Mol. Biol., vol. 215, 1990, pp. 403-410.

Altschul, S.F. and Gish, W., "[27] Local Alignment Statistics", Methods in Enzymology, vol. 266, 1996, pp. 460-480.

Altschul, S.F. et al., "Gapped BLAST and PSI-BLAST: a new generation of protein database search programs", Nucleic Acids Research, vol. 25, No. 17, 1997, pp. 3389-3402.

Auer, H.E., "Determining the meaning of claim terms", Nature Biotechnology, vol. 24, No. 1, 2006, pp. 41-43.

(Continued)

*Primary Examiner* — Barry A Chestnut

(74) *Attorney, Agent, or Firm* — Gary J. Gershik

(57) ABSTRACT

The invention relates to a fusion protein comprising a polypeptide of interest, a transmembrane domain and an HIV gag polypeptide, or their functionally equivalent variants. The invention also relates to the polynucleotides, vectors, host cells and virus-like particles expressing or presenting said fusion proteins and to the pharmaceutical, immunogenic or vaccines composition containing said fusion proteins, polynucleotides, vectors, host cells and virus-like particles and their use in human and veterinary medicine.

18 Claims, 24 Drawing Sheets

Specification includes a Sequence Listing.

(56) References Cited

OTHER PUBLICATIONS

Bryant, M. and Ratner, L., "Myristoylation-dependent replication and assembly of human immunodeficiency virus 1", Proc. Natl. Acad. Sci. USA, vol. 87, 1990, pp. 523-527.
Cervera, L. et al., "Generation of HIV-1 Gag VLPs by transient transfection of HEK 293 suspension cell cultures using an optimized animal-derived component free medium", Journal of Biotechnology, vol. 166, 2013, pp. 152-165.
Chambers, P. et al., "Heptad repeat sequences are located adjacent to hydrophobic regions in several types of virus fusion glycoproteins", Journal of General Virology, vol. 71, 1990, pp. 3075-3080.
Chan, D.C. et al., "Core Structure of gp41 from the HIV Envelope Glycoprotein", Cell, vol. 89, 1997, pp. 263-273.
Dhillon, A.K. et al., "Dissecting the Neutralizing Antibody Specificities of Broadly Neutralizing Sera from Human Immunodeficiency Virus Type 1—Infected Donors", Journal of Virology, vol. 81, No. 2, 2007, pp. 6548-6562.
Eggink, D. et al., "Selection of T1249-Resistant Human Immunodeficiency Virus Type 1 Variants", Journal of Virology, vol. 82, No. 13, 2008, pp. 6678-6688.
Feng, L. et al., "High-Level Expression and Mutagenesis of Recombinant Human Phosphatidylcholine Transfer Protein Using a Synthetic Gene: Evidence for a C-Terminal Membrane Binding Domain", Biochemistry, vol. 39, 2000, pp. 15399-15409.
Gartner, S. et al., "The Role of Mononuclear Phagocytes in HTLV-III/LAV Infection", Science Reports, vol. 233, 1986, pp. 215-219.
Humphreys, D.P. et al., "High-Level Periplasmic Expression in *Escherichia coli* Using a Eukaryotic Signal Peptide: Importance of Codon Usage at the 5' End of the Coding Sequence", Protein Expression and Purification, vol. 20, 2000, pp. 252-264.
Jain, S. et al., "Multiple tandem copies of conserved gp41 epitopes incorporated in gag virus-like particles elicit systemic and mucosal antibodies in an optimized heterologous vector delivery regimen", Vaccine, vol. 28, 2010, pp. 7070-7080.
Karlin, S. and Altschul, S.F., "Methods for assessing the, statistical significance of molecular sequence features by using general scoring schemes", Proc. Natl. Acad. Sci., vol. 87, 1990, pp. 2264-2268.
Karlin, S. and Altschul, S.F., "Applications and statistics for multiple high-scoring segments in molecular sequences", Proc. Natl. Acad. Sci., vol. 90, 1993, pp. 5873-5877.
Kolhekar, A.S. et al., "Peptidylglycine α-Hydroxylating Monooxygenase: Active Site Residues, Disulfide Linkages, and a Two-Domain Model of the Catalytic Core", Biochemistry, vol. 36, 1997, pp. 10901-10909.
Kuczkowska, K. et al., "*Lactobacillus plantarum* displaying CCL3 chemokine in fusion with HIV-1 Gag derived antigen causes increased recruitment of T cells", Microbial Cell Factories, vol. 14, No. 169, 2015, pp. 1-12.
Kyte, J. and Doolittle, R.F., "A Simple Method for Displaying the Hydropathic Character of a Protein", J. Mol. Biol., vol. 157, 1982, pp. 105-132.
Li., M. et al., "Human Immunodeficiency Virus Type 1 env Clones from Acute and Early Subtype B Infections for Standardized Assessments of Vaccine-Elicited Neutralizing Antibodies", Journal of Virology, vol. 79, No. 16, 2005, pp. 10108-10125.
Lua, L.H.L. et al., "Bioengineering Virus-Like Particles as Vaccines", Biotechnology and Bioengineering, vol. 111, No. 3, 2014, pp. 425-440.
Lupas, A., "Coiled coils: new structures and new functions", TIBS, vol. 21, 1996, pp. 375-382.
Mao, Y. et al., "Subunit organization of the membrane-bound HIV-1 envelope glycoprotein trimer", Nature Structural & Molecular Biology, vol. 19, No. 9, 2012, pp. 893-899.
Mather, J.P., "Establishment and Characterization of Two Distinct Mouse Testicular Epithelial Cell Lines", Biology of Reproduction, vol. 23, 1980, pp. 243-252.
Mather, J.P. et al., "Culture of Testicular Cells in Hormone-Supplemented Serum-Free Medium", Annals New York Academy of Sciences, 1982, pp. 44-68.
Molinos-Albert, L.M. et al., "Anti-MPER antibodies with heterogeneous neutralization capacity are detectable in most untreated HIV-1 infected individuals", Retrovirology, vol. 11, No. 44, 2014, pp. 1-12.
Montefiori, D.C., "Evaluating Neutralizing Antibodies Against HIV, SIV, and SHIV in Luciferase Reporter Gene Assays", Current Protocols in Immunology, vol. 12, No. 11, 2004, pp. 12.11.1-12.11.17.
Mothe, B. et al., "Definition of the viral targets of protective HIV-1-specific T cell responses", Journal of Translational Medicine, vol. 9, No. 208, 2011, pp. 1-20.
Narum, D.L. et al., "Codon Optimization of Gene Fragments Encoding *Plasmodium falciparum* Merzoite Proteins Enhances DNA Vaccine Protein Expression and Immunogenicity in Mice", Infection and Immunity, vol. 69, No. 12, 2001, pp. 7250-7253.
Needleman, S.B. and Wunsch, C.D., "A General Method Applicable to the Search for Similarities in the Amino Acid Sequence of Two Proteins", J. Mol. Biol., vol. 48, 1970, pp. 443-453.
Outchkourov, N. S. et al., "Optimization of the Expression of Equistatin in *Pichia pastoris*", Protein Expression and Purification, vol. 24, 2002, pp. 18-24.
Pearson, W.R. and Lipman, D.J., "Improved tools for biological sequence comparison", Proc. Natl. Acad. Sci. USA, vol. 85, 1988, pp. 2444-2448.
Peisajovich, S.G. and Shai, Y., "Viral fusion proteins: multiple regions contribute to membrane fusion", Biochimica et Biophysica Acta, vol. 1614, 2003, pp. 122-129.
Phogat, S. et al., "Analysis of the human immunodeficiency virus type 1 gp41 membrane proximal external region arrayed on hepatitis B surface antigen particles", Virology, vol. 373, 2008, pp. 72-84.
Sánchez-Palomino, S. et al., "A cell-to-cell HIV transfer assay identifies humoral responses with broad neutralization activity", Vaccine, vol. 29, 2011, pp. 5250-5259.
Smith, T.F. and Waterman, M.S., "Comparison of Biosequences", Advances in Applied Mathematics, vol. 2, 1981, pp. 482-489.
Suárez, T. et al., "The pre-transmembrane region of the human immunodeficiency virus type-1 glycoprotein: a novel fusogenic sequence", FEBS Letters, vol. 477, 2000, pp. 145-149.
Urlaub, G. and Chasin, L.A., "Isolation of Chinese hamster cell mutants deficient in dihydrofolate reductase activity", Proc. Natl. Acad. Sci. USA, vol. 77, No. 7, 1980, pp. 4216-4220.
Urlaub, G. et al., "Effect of Gamma Rays at the Dihydrofolate Reductase Locus: Deletions and Inversions", Somatic Cell and Molecular Genetics, vol. 12, No. 6, 1986, pp. 555-566.
Visciano, M.L. et al., "Generation of HIV-1 Virus-Like Particles expressing different HIV-1 glycoproteins", Vaccine, vol. 29, 2011, pp. 4903-4912.
Wei, X. et al., "Antibody neutralization and escape by HIV-1", Nature, vol. 422, 2003, pp. 307-312.
Zhou, W. et al., "Identification of a Membrane-Binding Domain within the Amino-Terminal Region of Human Immunodeficiency Virus Type 1 Gag Protein Which Interacts with Acidic Phospholipids", Journal of Virology, vol. 68, No. 4, 1994, pp. 2556-2569.
Zhu, P. et al., "Distribution and three-dimensional structure of AIDS virus envelope spikes", Nature, vol. 441, 2006, pp. 847-852.
International Search Report issued by the International Searching Authority (ISA/O.E.P.M.) dated Nov. 23, 2017 in connection with International Application No. PCT/IB2017/001101.

* cited by examiner

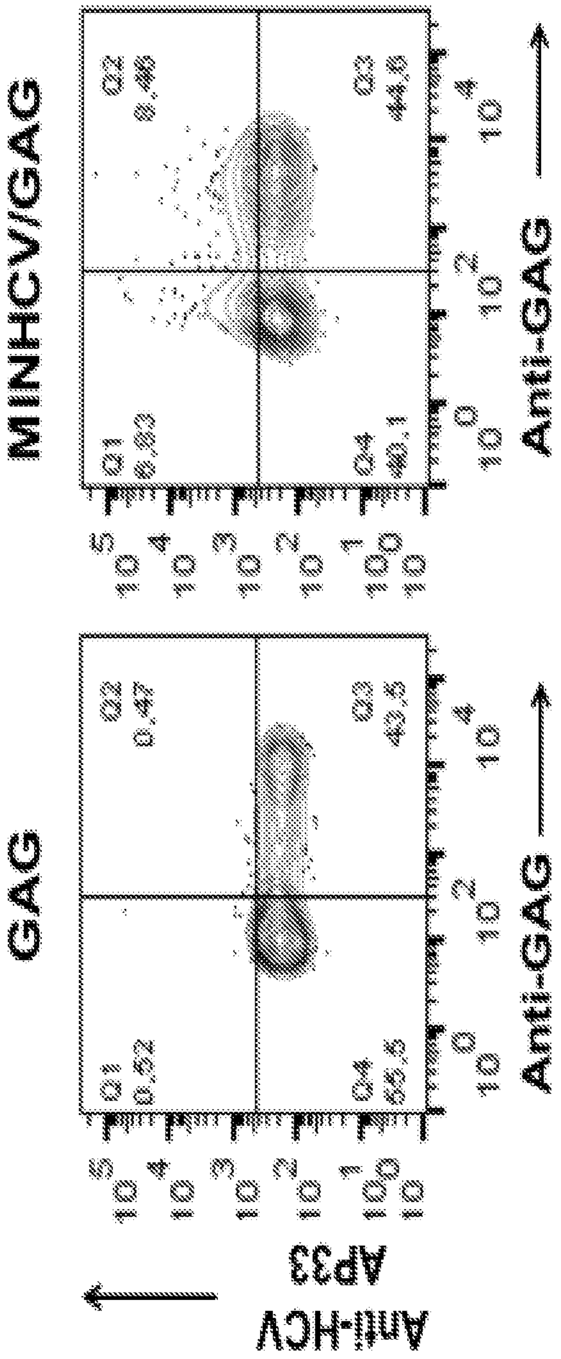
Fig. 11B (1)

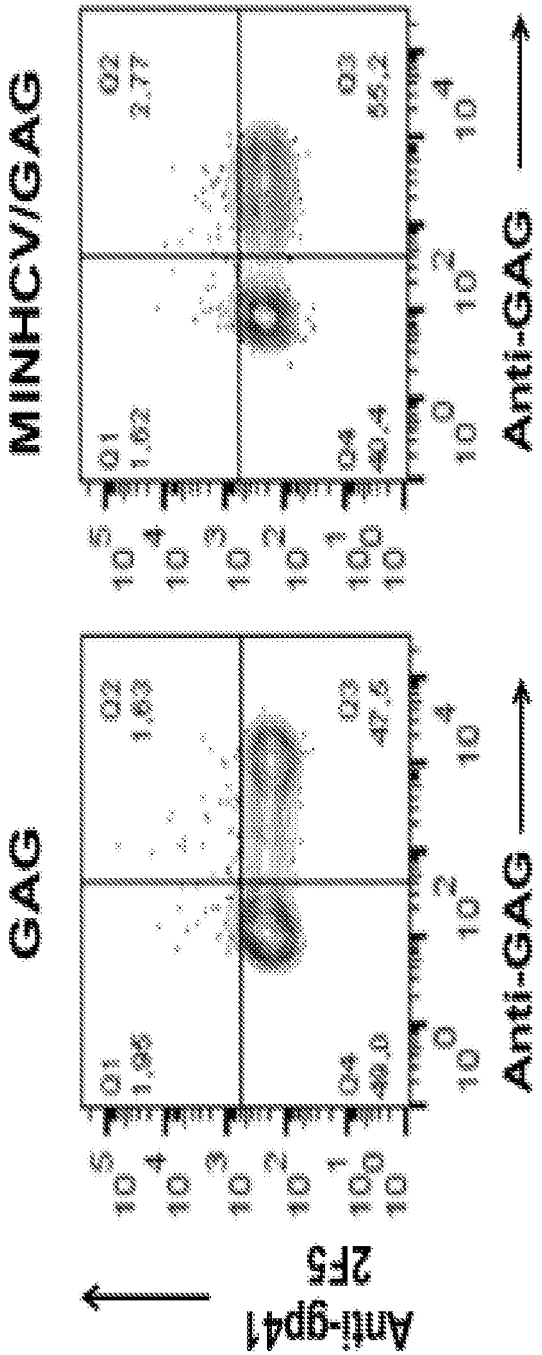
Fig. 11B (2)

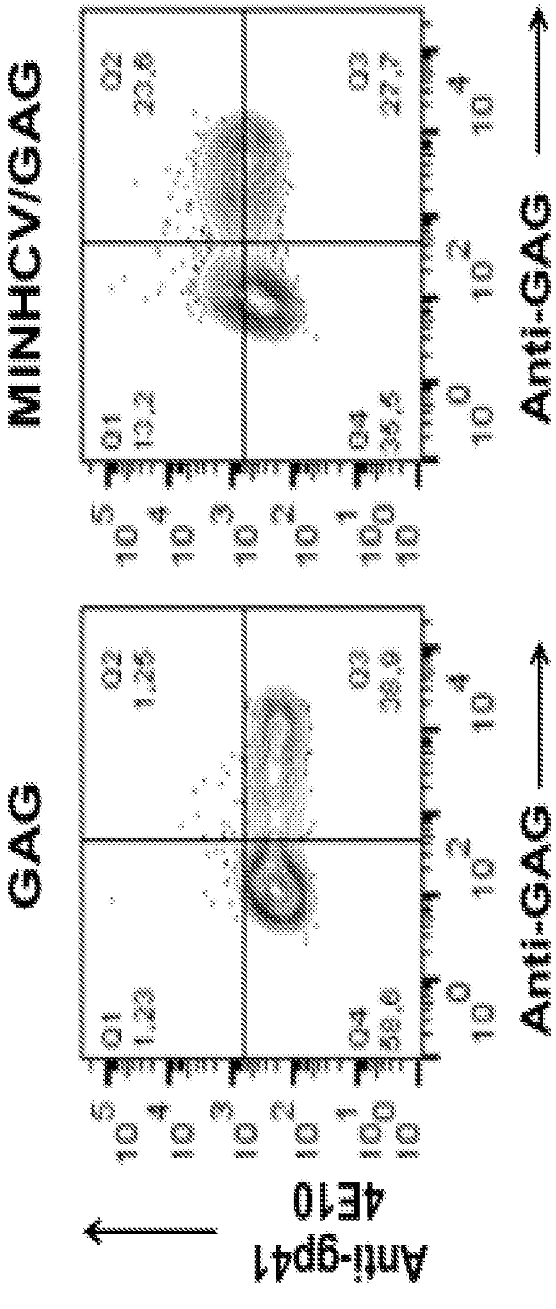
Fig. 11B (3)

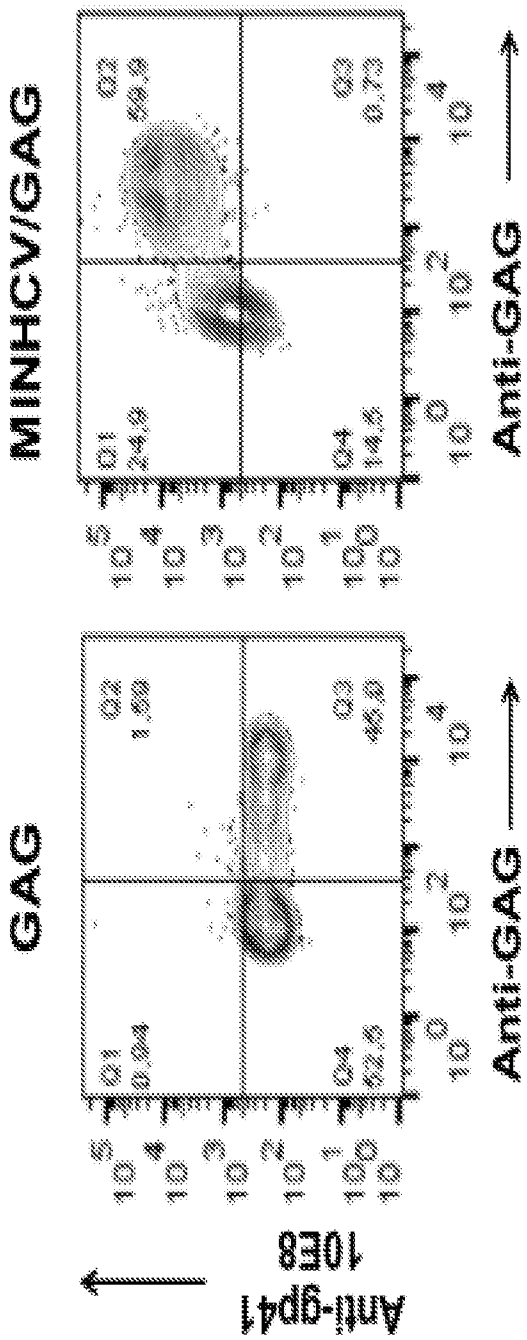
Fig. 11B (4)

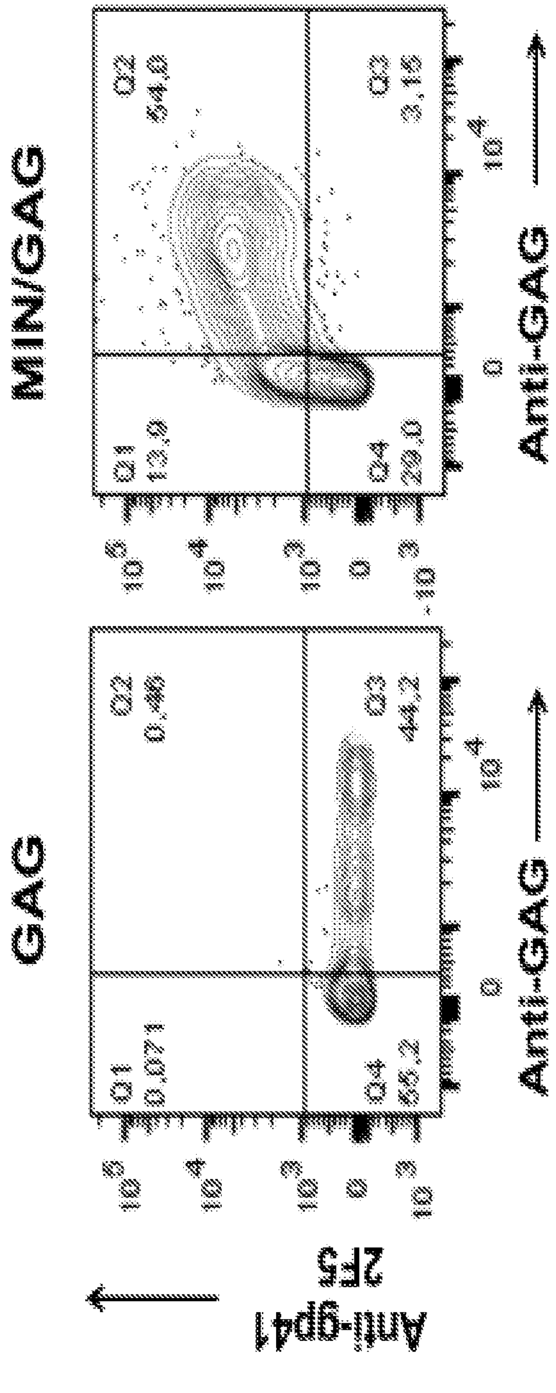
Fig. 12B (1)

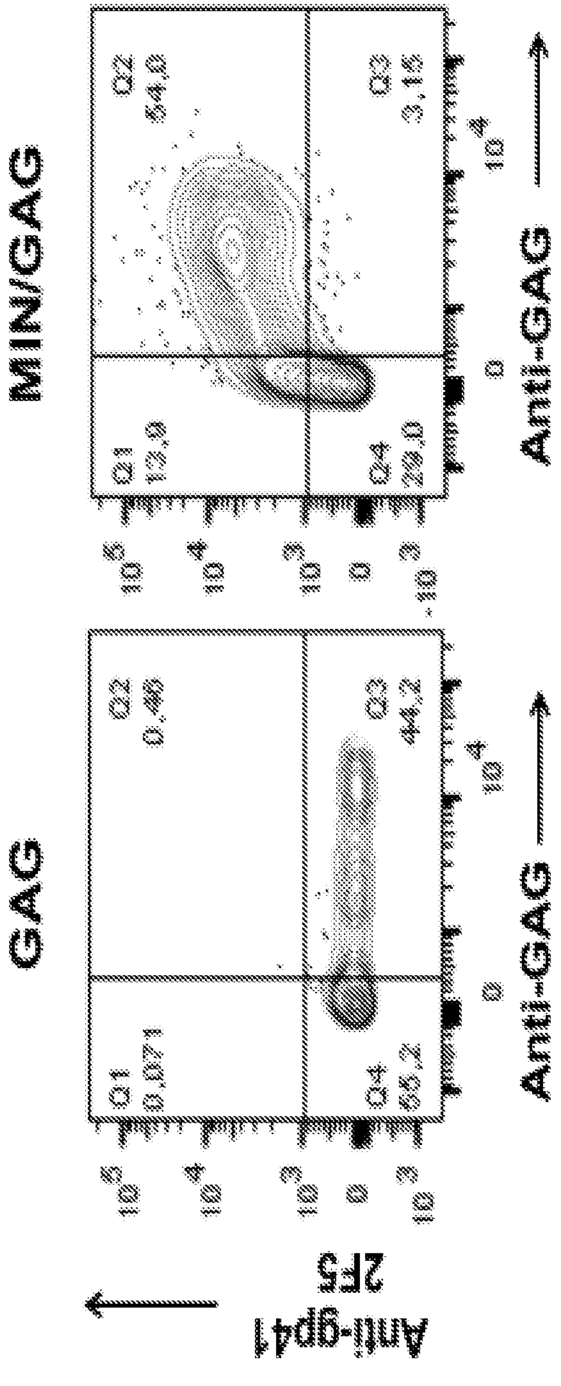
Fig. 12B (2)

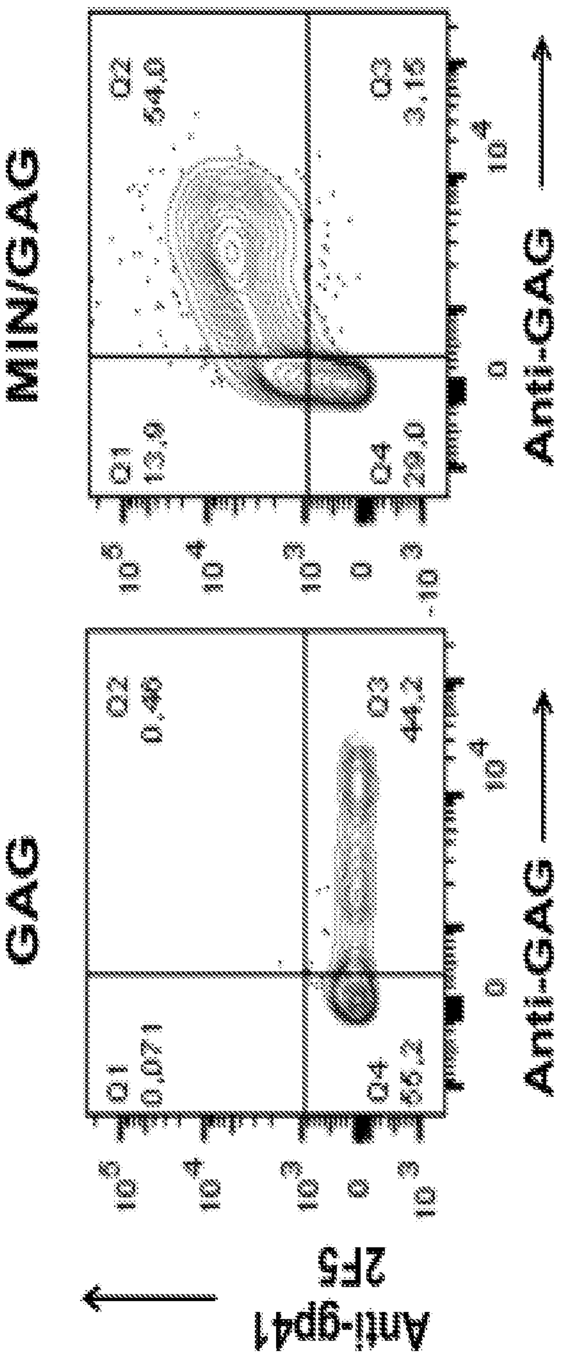
Fig. 12B (3)

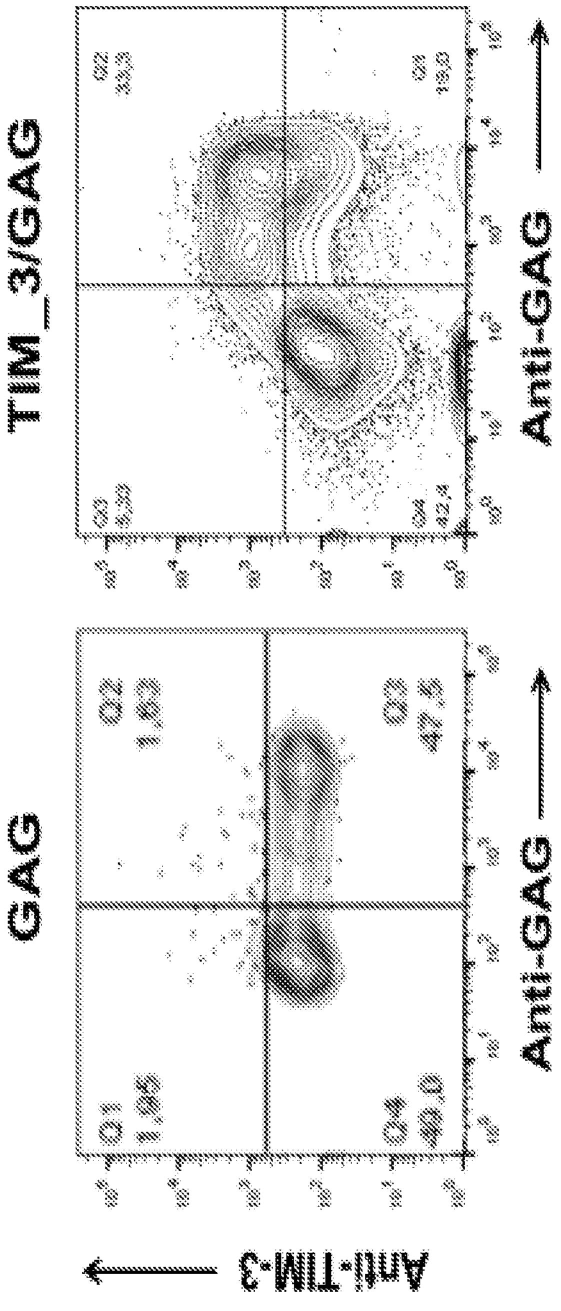
Fig. 12B (4)

VIRUS-LIKE PARTICLES WITH HIGH-DENSITY COATING FOR INDUCING THE EXPRESSION OF ANTIBODIES

CROSS REFERENCE TO RELATED APPLICATIONS

This application is a § 371 national stage of PCT International Application No. PCT/IB2017/001101, filed Jul. 26, 2017, claiming priority of European Patent Application No. 16382364.4, filed Jul. 27, 2016, the contents of each of which are hereby incorporated by reference into the application.

CROSS REFERENCE TO RELATED APPLICATIONS

This application incorporates-by-reference nucleotide and/or amino acid sequences which are present in the file named "200724 90822_Substitute_Sequence_Listing_AWG.txt", which is 78 kilobytes in size, and which was created Jul. 23, 2020 in the IBM-PC machine format, having an operating system compatibility with MS-Windows, which is contained in the text file filed Jul. 24, 2020 as part of this application.

FIELD OF THE INVENTION

The present invention relates to fusion proteins and virus-like particles (VLPs) useful in human and veterinary medicine. The invention refers also to a fusion protein comprising a polypeptide of interest, a transmembrane domain and an HIV gag polypeptide and their functionally equivalent variants. The invention relates additionally to the polynucleotides, vectors, host cells and VLPs particles expressing or presenting said fusion proteins, and to the pharmaceutical compositions, immunogenic or vaccines composition containing said fusion proteins, polynucleotides, vectors, host cells and VLPs and their use in treatment and prevention on infectious diseases.

BACKGROUND OF THE INVENTION

Virus-like particles (VLP) represent an excellent vaccine platform that has been proven effective against non-enveloped viruses such as the hepatitis B virus (HBV), human papilloma virus (HPV) or hepatitis E virus (HEV). See Lua L, et al., Biotechnol. Bioeng. 2014; 111:425-440. In these cases, VLPs contain a single capsid protein that is produced in prokaryotic or eukaryotic cell systems to spontaneously form VLP with excellent immunogenic results. The success and versatility of VLP production platforms has prompted the exploration of more complex designs. Some examples could be the generation of VLPs with heterologous antigen presentation by engrafting exogenous sequences in viral capsid proteins and the generation of enveloped VLPs, which contain a lipid bilayer derived from the VLP-producer cell and show higher heterogeneity than non-enveloped VLPs. See Bryant M, et al., Proc. Natl. Acad. Sci. USA 1990; 87:523-527 and Visciano M, et al., Vaccine 2011; 29(31):4903-4912.

Human immunodeficiency Virus (HIV) vaccine research has also approached the VLP technology. As for other retroviruses, HIV particles are enveloped structures formed by the multimerization of Gag structural proteins on the inner part of plasma membrane of infected cells through the myrystoylation of its N-term end. See Bryant, 1990, supra.

During the budding process, Gag polymers incorporate genomic viral RNA, different viral enzymes and accessory proteins and recruit cell surface expressed envelope glycoprotein complexes to ensure infectivity. However, it is well known that expression of a retroviral gag gene is sufficient to produce VLP structures lacking infectivity. See Visciano, 2011, supra and Cervera L, et al., J. Biotechnol. 2013; 166:152-165. These nude Gag VLPs can be modified either to incorporate proteins or RNAs and act as delivery vectors or to incorporate proteins on their surface to act as vaccine preparations. See Visciano, 2011, supra.

Over the last years, several groups have developed the production process of enveloped VLP focusing on HIV vaccine research. See Visciano, 2011 and Cervera, 2013, supra. However, the optimal generation of enveloped VLPs is not the only obstacle in these approaches. A second major difficulty is the complexity of HIV envelope glycoprotein (Env). See Mao Y, et al., Nat. Struct. Mol. Biol. 2012; 19:893-899. This large glycoprotein contains two subunits gp120 and gp41 capable of generating neutralizing and non-neutralizing antibodies. Despite multiple approaches to redesign protein mimics that act as immunogens to elicit neutralizing antibodies against Env, few positive results have been achieved See Mao, 2012, supra. Nevertheless, despite the efforts made to date, there still exists a continuing need in the art for novel ways of introducing antigen epitopes in VLPs compounds, as well as developing VLPs useful in eliciting an immune response against particular antigen epitopes.

SUMMARY OF THE INVENTION

In a first aspect, the present invention relates to a fusion protein which comprises from the N- to the C-terminus:

(a) a polypeptide of interest, or a functionally equivalent variant thereof, (b) a transmembrane domain, or a functionally equivalent variant thereof, and (c) an HIV gag polypeptide, or a functionally equivalent variant thereof.

In an additional aspect, the invention relates to a polynucleotide encoding a fusion protein according to the invention.

In a further aspect, the invention refers to a vector comprising a polynucleotide according to the invention.

In another aspect, the invention is directed to a host cell comprising a fusion protein or a vector according to the invention.

In a still further aspect, the invention relates to a method for preparing a VLP loaded with an immunogenic polypeptide comprising:

(a) expressing in a cell a fusion protein according to the invention, and (b) recovering the VLP from the extracellular medium.

Additionally, the present invention relates to a virus like-particle comprising the fusion protein according to the invention or obtained through using a method of the invention.

In a further aspect, the invention refers to a pharmaceutical composition comprising a fusion protein, a polynucleotide, a vector, a host cell or a virus-like particle according to the invention, or a combination thereof.

In another aspect, the invention is directed to a fusion protein, a polynucleotide, a vector, a host cell, a virus-like particle or a pharmaceutical composition according to the invention, or combination thereof, for use in medicine.

In a still further aspect, the invention relates to a fusion protein, a polynucleotide, a vector, a host cell, a virus-like particle or a pharmaceutical composition according to the invention, or combination thereof, for use in the treatment or prevention of a disease caused by an infection or tumor in a subject. In an alternative form of this aspect, the invention relates to a method of treating or preventing disease caused by an infection or tumor in a subject which comprises the administration of a therapeutically effective amount of a fusion protein, a polynucleotide, a vector, a host cell, a virus-like particle or a pharmaceutical composition according to the invention, or combination thereof, to a subject. In a further alternative form of this aspect, the invention refers to the use of a fusion protein, a polynucleotide, a vector, a host cell, a virus-like particle or a pharmaceutical composition according to the invention, or combination thereof, in the manufacture of a medicament for the treatment or prevention of a disease caused by an infection or tumor in a subject.

Additionally, the present invention relates to a kit comprising a fusion protein, a polynucleotide, a vector, a host cell, a virus-like particle or a pharmaceutical composition according to the invention, or a combination thereof.

DEPOSIT OF MICROORGANISMS

Figure 1:
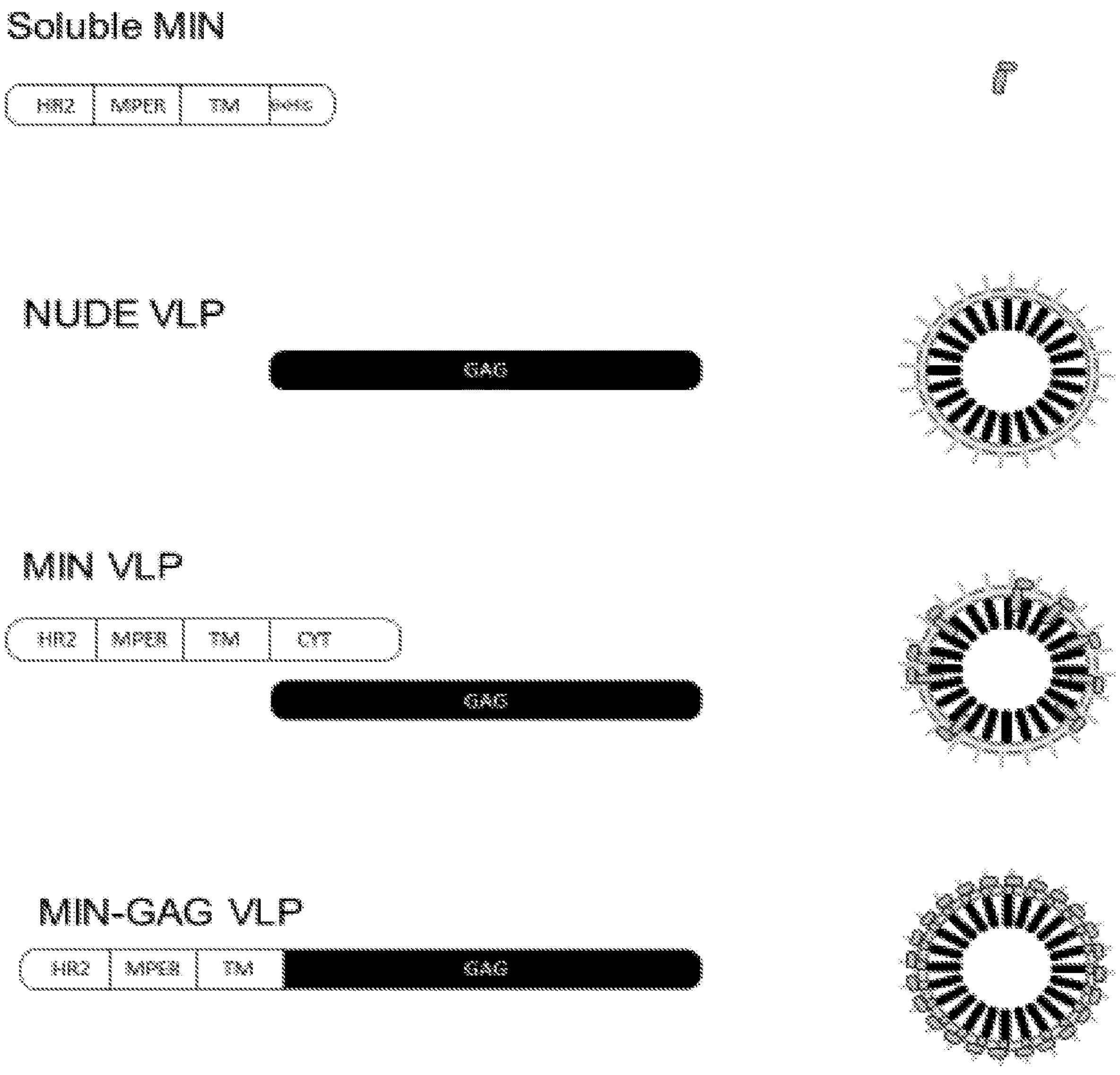
FIG. 1. Different protein and VLP preparations used for immunogenicity assays. A gp41-derived protein (MIN) encompassing the HR2, MPER and TM regions of the gp41 glycoprotein was expressed in *E. coli*, a 6×His tag was included in the design at the C-terminus of the protein for purification. Nude VLPs were generated by transfection of an HIV-1 gag coding plasmid in HEK-293T cells. These nude VLPs expose human proteins coming from the producer cell membrane (light grey elements on the surface of VLP). Alternatively, MIN-VLPs were produced by co-transfection of the same gag expressing plasmid with a plasmid coding for the MIN protein that contains the full cytoplasmic tail of gp41. MIN protein is incorporated on the surface of VLPs. A final VLP preparation was produced by expressing a variant of MIN protein lacking the cytoplasmic tail fused to a gag sequence (starting at residue 2). The VLPs formed are expected to display high density MPER epitopes on their surface (gag:gp41 stoichiometry 1:1).

The plasmid pcDNA3.1/MINGAG-3.7 was deposited on Jul. 25, 2012, under accession number DSM 26214 at the DSMZ—Deutsche Sammlung von Mikroorganismen and Zellkulturen, InhoffenstraBe 7 B, D-38124 Braunschweig, Federal Republic of Germany.

SEQUENCE LISTING

The nucleic and amino acid sequences depicted in the accompanying sequence listing are shown using the standard letter abbreviations and codes applied conventionally in the art. Only one strand of each nucleic acid sequence is shown, but the complementary strand is understood as included by any reference to the displayed strand. The accompanying sequence listing an integral part of the present invention.

DETAILED DESCRIPTION OF THE INVENTION

One of the main limitations of the generation of antibodies is the poor incorporation of antigens of interest into VLPs in vitro. The present invention describes novel VLPs using gp41-based and other proteins, which include a transmembrane domain fused to gag for overcoming this limitation. This design disclosed in the present invention: (i) allows for the membrane localization of these proteins, (ii) maintains the VLP self-packing ability of Gag, (iii) shows increased gp41 surface density and (iv) improves the correct spatial presentation of antigens, thus (v) enhances the immunogenic responses to said antigens. The results clearly demonstrate the increased immunogenicity of the VLPs of the invention.

1. Definitions of General Terms and Expressions

The term "AIDS", as used herein, refers to the symptomatic phase of HIV infection, and includes both Acquired Immune Deficiency Syndrome (commonly known as AIDS) and "ARC," or AIDS-Related Complex. See Adler M, et al., Brit. Med. J. 1987; 294: 1145-1147. The immunological and clinical manifestations of AIDS are well known in the art and include, for example, opportunistic infections and cancers resulting from immune deficiency.

The term "allergen", as used herein, refers to a peptide, polypeptide or protein to which a subject is sensitive and that may cause an immune reaction (e.g. allergen extracts of pollens, insects, food or food products; components present in saliva, insect claws or stings; plant components).

The term "amino acid", as used herein, refers to naturally occurring and synthetic amino acids, as well as amino acid analogs and amino acid mimetics that function in a manner similar to the naturally occurring amino acids. Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes.

The term "codon optimized", as used herein, refers to the alteration of codons in nucleic acids to reflect the typical codon usage of the host organism to improve the expression of a reference polypeptide without altering its amino acid sequence. There are several methods and software tools known in the art for codon optimization. See Narum D, et al., Infect. Immun. 2001; 69(12):7250-7253), Outchkourov N, et al., Protein Expr. Purif 2002; 24(1):18-24, Feng L, et al., Biochemistry 2000; 39(50):15399-15409 and Humphreys D, et al., Protein Expr. Purif 2000; 20(2):252-264.

The term "comprising" or "comprises", as used herein, discloses also "consisting of" according to the generally accepted patent practice.

The terms "Env" or "gp160", as used herein, refer to a glycoprotein having either the antigenic specificity or the biological function of the outer envelope protein (Env) of HIV and encompassing two subunits, the gp120 and the gp41 glycoproteins. Exemplary sequences of wild-type (wt) gp160 polypeptides are available. See GenBank accession nos. AAB05604 and AAD12142.

The term "epitope", as used herein, refers to that portion of a given immunogenic substance that is the target of (i.e. is bound by) an antibody or cell-surface receptor of a subject's immune system that has mounted an immune response against said immunogenic substance, as determined by any methods known in the art. Further, an epitope may be defined as a portion of an immunogenic substance that is recognized by a humoral or cellular response, and in particular, an antibody response or a T-cell response in a subject, as determined by any method available in the art. An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site".

The terms "express", "expresses" or "expression", as used herein, refers to the transcription of a nucleic acid molecule, and optionally, its translation. Typically, transcription and translation of a coding sequence will result in the production of polypeptide such as the fusion proteins of the invention.

The expression "functionally equivalent variant", as used herein, refers to: (i) a polypeptide resulting from the modification, deletion or insertion or one or more amino acids and which substantially preserves the activity of its reference polypeptide and (ii) a polynucleotide resulting from the modification, deletion or insertion of one or more bases and which substantially preserves the activity of the polypeptide expressed by the reference nucleic acid. Functionally equivalent variants contemplated in the context of the present invention, include polypeptides which show at least 60%, 70%, 80%, 85%, 90%, 92%, 94%, 96%, 98%, 99% of similarity or identity with sequences SEQ ID NOs: 1-2, 5, 15-28, 30, 32, 34, 36 and 38 and which retain substantially equivalent ability to induce VLP formation in the case of a gag polypeptide variant or retains the ability to be embedded into the plasma membrane in the case of a functionally equivalent variant of the HIV gp41 polypeptide. Functionally equivalent variants contemplated in the context of the present invention include also polynucleotides which show at least 60%, 70%, 80%, 85%, 90%, 92%, 94%, 96%, 98%, 99% of similarity or identity with sequences SEQ ID NOs: 3-4, 6-14, 29, 31, 33, 35 and 37 and that, when expressed, retain substantially equivalent ability to induce VLP formation in the case of a gag polypeptide variant or retains the ability to be embedded into the plasma membrane in the case of a functionally equivalent variant of the HIV gp41 polypeptide. The degree of identity or similarity between two polypeptides or two polynucleotides is determined by using computer-implemented algorithms and methods that are widely known in the art. The identity and similarity between two sequences of amino acids is preferably determined using the BLASTP algorithm. See Altschul S, et al., "BLAST Manual" (NCBI NLM NIH, Bethesda, Md., USA, 2001).

The term "fusion protein", as used herein, relates to proteins generated by gene technology which consist of two or more functional domains derived from different proteins. A fusion protein may be obtained by conventional means (e.g. by means of gene expression of the nucleotide sequence encoding for said fusion protein in a suitable cell).

The term "gag polypeptide", as used herein relates to a primary protein product of the gag gene of HIV, which provides the basic physical infrastructure of the virus, and which is processed by viral protease during maturation to MA (matrix protein, p17), CA (capsid protein, p24), SP1 (spacer peptide 1, p2), NC (nucleocapsid protein, p7), SP2 (spacer peptide 2, p1) and P6 protein.

The term "gp41", as used herein, refers to human immunodeficiency virus-I envelope glycoprotein gp4 1. Gp4 1 is a subunit which forms the Env glycoprotein of HIV-1 together with gp120. Env is a trimer composed of three external subunits (gp120) and three transmembrane subunits (gp41). The extracellular moiety of gp41 protein contains three essential functional regions: a fusion peptide (FP), a N-terminal heptad repeat (HR1) and a C-terminal heptad repeat (HR2). The HR1 and HR2 regions contain several leucine zipper-like motifs which have tendency to form coiled structures. See Peisajovich S, Shai Y, Biochem. Biophys. Acta 2003; 1614:122-129; Suarez T, et al., FEBS Lett. 2000; 477:145-149; Chan D, et al., Cell 1997; 89:263-273. The nucleic acid and amino acid sequences of a large number of HIV gp-41 are readily available to the public. See HIV Sequence Database, hiv.1an1.gov, July 2017.

The term "gp120", as used herein, refers to a glycoprotein having either the antigenic specificity or the biological function of the outer envelope protein (env) of HIV. A "gp120 protein" is a molecule derived from a gp120 region of an Env polypeptide. The amino acid sequence of gp120 is approximately 511 amino acids. Gp120 is a heavily N-glycosylated protein with an apparent molecular weight of 120 kDa. Gp120 contains five relatively conserved domains (C1-C5) interspersed with five variable domains (V1-V5). The variable domains contain extensive amino acid substitutions, insertions and deletions. A "gp120 polypeptide" includes both single subunits and multimers. The gp41 portion is anchored in (and spans) the membrane bilayer of the virion, while the gp120 segment protrudes into the surrounding environment. The receptor binding domain of gp120 is localized to N-terminal half of the protein. This is followed by a proline rich region (PRR), which behaves either as a hinge or trigger to communicate receptor binding to the fusion machinery. The C-terminus of gp120 is highly conserved and interacts with gp41. See GenBank accession nos. AAB05604 and AAD12142.

The terms "heptad repeat 2" or "HR2", as used herein, refer, but is not limited to, a heptad repeat region located at the carboxy terminus of the extracellular portion of the wild-type gp41. See Eggink D, et al., J. Virol. 2008; 82(13): 6678-6688. A heptad repeat is a motif in which a hydrophobic amino acid is repeated every seven residues. Such motifs are designated a through g. See Lupas A, Trends Biochem. Sci. 1996; 21:375-382. Heptad repeats which contain hydrophobic or neutral residues at the a and d positions can form alpha helices and are able to interact with other heptad repeats by forming coiled coils. See Chambers P, et al., J. Gen. Virol. 1990; 71:3075-3080 and Lupas, 1996, supra.

The term "HIV", as used herein, include HIV-1 and HIV-2, SHIV and SIV. "HIV-1" means the human immunodeficiency virus type-1. HIV-1 includes, but is not limited to, extracellular virus particles and the forms of HIV-1 associated with HIV-1 infected cells. The HIV-1 virus may represent any of the known major subtypes (Classes A, B, C, D E, F, G and H) or outlying subtype (Group 0) including laboratory strains and primary isolates. "HIV-2" means the human immunodeficiency virus type-2. The HIV-1 strains include, but are not limited to, the HIV-$1_{JR-FL}$, HIV-$1_{DH123}$, HIV-$1_{Gun-1}$, HIV-$1_{89.6}$, and HIV-$1_{HXB2}$ strains. HIV-2 includes, but is not limited to, extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes, but is not limited to, extracellular virus particles and the forms of SIV associated with SIV infected cells.

The term "HIV exposure", as used herein, refers to the contact of an uninfected subject with a subject having an HIV infection or AIDS, or the contact with body fluids from such HIV-infected subject, in which such fluids from the infected subject contact a mucous membrane, a cut or abrasion in the tissue (e.g. needle stick, unprotected sexual intercourse), or other surface of the uninfected subject in such a way that the virus could be transmitted from the infected subject or infected subject's body fluids to the uninfected subject.

The term "HIV infection", as used herein, refers to indications of the presence of the HIV virus in an individual including asymptomatic seropositivity, AIDS-related complex (ARC), and acquired immunodeficiency syndrome (AIDS).

The term "HIV-$1_{JR-FL}$", as used herein, refers to an HIV-1 strain originally isolated from the brain tissue of an AIDS patient taken at autopsy and co-cultured with lectin-activated normal human PBMCs.

The terms "host cell" and "recombinant host cell", as used interchangeably herein, refer to a cell into which a nucleic acid or vector according to the invention has been introduced. "Host cell" and "recombinant host cell" includes also the progeny, or potential progeny, of such a cell. Because certain modifications may occur in succeeding generations due to either mutation or environmental influences, such progeny may not, in fact, be identical to the parent cell, but can be still included within the scope of the term as used herein.

The terms "identical" or percent "identity" in the context of two or more nucleic acids or polypeptides refer to two or more sequences or subsequences that are the same or have a specified percentage of nucleotides or amino acid residues that are the same when compared and aligned (introducing gaps, if necessary) for maximum correspondence, not considering any conservative amino acid substitutions as part of the sequence identity. The percent of identity can be measured using sequence comparison software or algorithms or by visual inspection. Various algorithms and software are known in the art which can be used to obtain alignments of amino acid or nucleotide sequences. Examples of algorithms suitable for determining sequence similarity include, but are not limited to, the BLAST, Gapped BLAST, and BLAST 2.0, WU-BLAST-2, ALIGN, and ALIGN-2 algorithms. See Altschul S, et al., Nuc. Acids Res. 1977; 25:3389-3402, Altschul S, et al., J. Mol. Biol. 1990; 215:403-410, Altschul S, et al., Meth. Enzymol. 1996; 266:460-480, Karlin S, et al., Proc. Natl. Acad. Sci. USA 1990; 87:2264-2268, Karlin S, et al., Proc. Natl. Acad. Sci. USA 1993; 90:5873-5877, Genentech Corp, South San Francisco, Calif., US, blast.ncbi.nlm-.nih.gov, July 2017. Methods of alignment of sequences for comparison are well known in the art. Optimal alignment of sequences for comparison can be conducted, for instance, by the Smith-Waterman local homology algorithm, by the Needleman-Wunsch homology alignment algorithm, by the Pearson-Lipman similarity search method, by computerized implementations of these algorithms or by manual alignment and visual inspection. See Smith T, et al., Adv. Appl. Math. 1981; 2:482-489, Needleman S, et al., J. Mol. Biol. 1970; 48:443-453, Pearson W, et al., Lipman D, Proc. Natl. Acad. Sci. USA 1988; 85:2444-2448, the GAP, BESTFIT, FASTA and TFASTA programs, Wisconsin Genetics Software Package, Genetics Computer Group, Madison, Wis., USA; Ausubel F, et al., Eds., "Short Protocols in Molecular Biology", 5th Ed. (John Wiley and Sons, Inc., New York, N.Y., USA, 2002).

The term "immunogenic composition", as used herein, refers to a pharmaceutical composition capable of eliciting a humoral (e.g. antibodies) or cellular (e.g. cytotoxic T-cell) immune response in a subject against a specific immunogen.

The term "immunogenic polypeptide", as used herein, relates to a polypeptide from a pathogenic organism, tumor marker or allergen that, when administered to a subject, can induce a protective immune response against the organism, tumor marker or allergen.

The term "immunologically functional equivalent", as used herein, refers to a variant of a polypeptide that retains substantially equivalent ability to induce an immune response in a subject as the reference polypeptide. The term "immunologically functional equivalent" is well known in the art and is further defined in detail herein. Immunologically functional equivalents may increase the antigenicity of a polypeptide, maintain the same level of antigenicity of the reference polypeptide, or decrease the antigenicity of a polypeptide only slightly so that it maintains its usefulness as an antigen in an immunogenic composition.

The term "infectious disease", as used herein, relates to diseases caused by pathogens such as viruses, bacteria, fungi, protozoa and parasites.

The term "kit", as used herein, refers to a product containing the different reagents necessary for carrying out the uses and methods according to the invention which is packed as to allow their transport and storage. Materials suitable for packing the components of the kit include crystal, plastic (e.g. polyethylene, polypropylene, polycarbonate), bottles, vials, paper or envelopes.

The term "KLH", as used herein, relates to a large, multisubunit, oxygen-carrying, metalloprotein that is found in the hemolymph of the giant keyhole limpet, Megathura crenulata, a species of keyhole limpet that lives off the coast of California, from Monterey Bay to Isla Asuncion off Baja California.

The terms "linker region" or "linker", as used herein, refer to any heterologous polypeptide of at least 1, 2, 3, 4 or 5 or more amino acids in length, which when inserted between a first and second region yields a functional linkage joining both regions and wherein each region can preserve its functional and immunological properties.

The terms "membrane-proximal external region" or "MPER", as used herein, refer, but are not limited to, a highly conserved region of the gp41 ectodomain adjacent to the viral membrane.

The terms "neutralizing antibody" or "nAb", as used herein, is any antibody or antigen-binding fragment that binds to an extracellular molecule (e.g. a protein or a protein domain in the surface of a pathogenic virus or bacteria) and interferes with the ability of the pathogen to infect a cell or modulates its activity. In the context of the invention, the pathogen is preferably HIV, and more specifically, the gp120 protein of the HIV viral envelope. In particular, the term "HIV neutralizing antibody" refers to a neutralizing antibody with affinity to the CD4 binding site of gp120 such as IgGb12. The term "neutralizing antibodies" includes the subclass of bnAbs. As used herein, "broadly neutralizing antibody" or "bnAb" is understood as an antibody obtained by any method that, when delivered at an effective dose, can be used as a therapeutic agent for the prevention or treatment of HIV infection or AIDS against more than 7 strains of HIV, preferably more than 8, 9, 10, 11, 12, 13, 14, 15, 16, 17, 18, 19, 20 or more strains of HIV.

The terms "NL4-3" and "BaL", as used herein, refer to two different HIV isolates commonly used in the laboratory. The NL4-3 isolate was cloned from NY5 and LAV proviruses. See Adachi A, et al., J. Virol. 1986; 59:284-291. The BaL isolate was obtained from a primary culture of adherent cells grown from explanted lung tissue. See Gartner S, et al., Science 1986; 233:215-219.

The terms "nucleic acid", "polynucleotide" and "nucleotide sequence", as used interchangeably herein, relate to any polymeric form of nucleotides of any length and composed of ribonucleotides or deoxyribonucleotides. The terms include both single-stranded and double-stranded polynucleotides, as well as modified polynucleotides (e.g. methylated, protected). Typically, the nucleic acid is a "coding sequence" which, as used herein, refers to a DNA sequence that is transcribed and translated into a polypeptide in a host cell when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g. mammalian) DNA, and even synthetic DNA sequences. A transcription termination sequence will usually be located 3' to the coding sequence.

The term "operably linked", as used herein, means that the nucleotide sequence of interest is linked to the regulatory sequence(s) in a manner that allows for expression of the nucleotide sequence (e.g. in an in vitro transcription/translation system or in a host cell when the vector is introduced into the host cell). See Auer H, Nature Biotechnol. 2006; 24: 41-43.

The expression "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and, intrasternal injection and infusion.

The expression "peripheral blood mononuclear cell" or its abbreviation "PBMC", as used herein, refer to any peripheral blood cell having a round nucleus. These cells consist of lymphocytes (i.e. T cells, B cells, NK cells) and monocytes.

The expression "pharmaceutically acceptable carrier", as used herein, includes any and all solvents, dispersion media, coatings, antibacterial and antifungal agents, isotonic and absorption delaying agents that are physiologically compatible with the fusion proteins, polynucleotides, vectors, host cells or VLP according to the invention.

The term "pharmaceutical composition", as used herein, refers to a combination of at least one fusion protein, polynucleotide, vector, host cell or VLP according to the invention and at least one other ingredient, including but not limited to a pharmaceutically acceptable carrier, that render the combination suitable for administration to a subject. The term "pharmaceutical composition" includes, but is not limited to, immunogenic and vaccine compositions.

The terms "polypeptide," "peptide" and "protein" are used interchangeably herein to refer to a polymer of amino acid residues, which may contain more than one amino acid residue (e.g. dipeptide, tripeptide, oligopeptide). The terms apply to amino acid polymers in which one or more amino acid residue is an artificial chemical mimetic of a corresponding naturally occurring amino acid, as well as to naturally occurring amino acid polymers and non-naturally occurring amino acid polymer.

The terms "prevent," "preventing" and "prevention", as used herein, refer to inhibiting the inception or decreasing the occurrence of a disease in a subject. The prevention may be complete (e.g. the total absence of pathological cells in a subject). The prevention may also be partial, such as, for example, lowering the occurrence of pathological cells in a subject. Prevention also refers to a reduced susceptibility to a clinical condition. Within the context of the present invention, the terms "prevent," "preventing" and "prevention", refer specifically to averting or reducing the probability of HIV infection in a subject sustaining HIV exposure.

The expression term "product result from the processing of the Env protein", as used herein, refers to any of the proteins produced by the processing of the gp160 protein.

The term "recombinant bacterium", as used herein, refers to any bacterium modified by the introduction of heterologous DNA. "Wild-type" or "control" bacterium include bacterium as found in its natural state without genetic manipulation or that are substantially identical to the recombinant bacterium, but do not express one or more of the proteins encoded by the heterologous DNA (e.g. contains a plasmid without the coding sequence of the heterologous polypeptide of interest). The term is intended to include progeny of the bacterium originally modified by the introduction of heterologous DNA.

The expression "stringent hybridization conditions", as used herein, refers to conditions under which a probe will hybridize to its target subsequence, typically in a complex mixture of nucleic acid, but to no other sequences.

The term "subject", as used herein, refers to an individual, plant or animal, such as a human, a nonhuman primate (e.g. chimpanzees and other apes and monkey species); farm animals, such as birds, fish, rabbits, goats, sheep, pigs, cattle and horses; companion animals, such as dogs and cats; laboratory animals including rodents, such as mice, rats and guinea pigs. The term does not denote a particular age or sex. The term "subject" encompasses an embryo and a fetus. In a preferred embodiment, the subject is a human.

The term "substantially equivalent", as used herein, refers to variants which are able to generate an immune response which is differs from the immune response generated with the native region by no more than 5%, 10%, 15%, 20%, 25%, 30%, 35%, 40%, 45%, 50%, 55%, 60%, 65%, 70%, 75%, 80%, 85%, 90% or 95%.

The term "therapeutic agent" as used herein, refers to an atom, molecule or compound useful in the treatment or prevention of a disease. Examples of therapeutic agents include, but are not limited to, epitopes, antigens, immunogens, antibodies, antibody fragments, drugs, cytotoxic agents, pro-apopoptotic agents, toxins, nucleases (e.g. DNAses and RNAses), hormones, immunomodulators, chelators, photoactive agents or dyes, anti-angiogenic agents, chemotherapeutic agents, cytokines, chemokines, prodrugs, enzymes, binding proteins, peptides or combinations thereof.

The term "therapeutically effective amount", as used herein, refers to the dose or amount of a fusion protein, polynucleotide, vector, host cell, VLP, pharmaceutical composition or immunogenic or vaccine composition according to the invention, or a combination thereof, that produces a therapeutic response or desired effect in a subject.

The terms "transmembrane domain" and "TM domain", as used herein, refer to an amino acid sequence of approximately hydrophobic residues with an occasional polar residue of integral proteins that pass across membrane.

The expression "transmembrane domain of the HIV gp41 polypeptide", as used herein, refers to the region of the gp41 polypeptide that is embedded into the plasma membrane once gp41 has acquired its native topology.

The terms "treat" and "treatment", as used herein, refer to the administration of a fusion protein, polynucleotide, vector, host cell, VLP, pharmaceutical composition, immunogenic or vaccine composition according to the invention, or a combination thereof, for controlling the progression of a disease after its clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state and remission (both partial and total). The control of progression of the disease also involves an extension of survival compared with the expected survival if treatment was not applied. Within the context of the present invention, the terms "treat" and "treatment" refer specifically to stopping or slowing the infection and destruction of healthy CD4+ T cells in an HIV infected subject. It also refers to the stopping and slowing of the onset of symptoms of the acquired immunodeficiency disease such as extreme low CD4+ T cell count and repeated infections by opportunistic pathogens. Beneficial or desired clinical results include, but are not limited to, an increase in absolute naïve CD4+ T cell count (range 10-3520), an increase in the percentage of CD4+ T cell over total circulating immune cells (range 1-50%), or an increase in CD4+ T cell count as a percentage of normal CD4+ T cell count in an uninfected subject (range 1-161%). "Treatment" can also mean prolonging survival of the infected subject as compared to expected survival if the subject does not receive any HIV targeted treatment.

The terms "vaccine" and "vaccine composition", as used herein, refers to an immunogenic composition for in vivo administration to a subject, to confer protection against disease, and particularly, a bacterial or viral disease.

The term "vector", as used herein, refers to a nucleic acid molecule, linear or circular, that comprises a nucleic acid according to the invention operably linked to additional segments that provide for its autonomous replication in a host cell or according to the expression cassette of the nucleic acid molecule.

The terms "virus-like particle vector" and "VLP", as used herein, refer to non-infectious particles resembling viruses that do not contain any viral genetic material. VLPs are the result of the expression of viral structural proteins, such as capsid proteins, and their self-assembly.

2. Fusion Proteins

In a first aspect, the present invention relates to a fusion protein which comprises from the N- to the C-terminus:

(a) a polypeptide of interest, or a functionally equivalent variant thereof, (b) a transmembrane domain, or a functionally equivalent variant thereof, and (c) an HIV gag polypeptide, or a functionally equivalent variant thereof.

In a preferred embodiment, the polypeptide of interest comprises a therapeutic agent, a region of a therapeutic agent, or a functionally equivalent variant thereof. Examples of therapeutic agents include, but are not limited to, epitopes, antigens, immunogens, antibodies, antibody fragments, drugs, cytotoxic agents, pro-apopoptotic agents, toxins, nucleases (e.g. DNAses and RNAses), hormones, immunomodulators, chelators, photoactive agents or dyes, anti-angiogenic agents, chemotherapeutic agents, cytokines, chemokines, prodrugs, enzymes, binding proteins, peptides, or a region thereof. Preferably, the therapeutic agent is an epitope, antigen, immunogen, or a functionally equivalent variant thereof. In another embodiment, the polypeptide of interest includes a combination of one or more therapeutic agents, their regions or functionally equivalent variants. Examples of these combinations include, but are not limited to, a polypeptide of interest comprising two or more therapeutic agents of different origin (e.g. viral antigen/bacterial antigen, tumor marker/bacterial antigen) or of the same origin (e.g. two or more antigens of the same pathogen).

Preferably, the HIV gag polypeptide, or the functionally equivalent variant thereof, is from HIV-$1_{HXB2}$. The full sequence of the gag polypeptide from HXB2 has accession number P04585-1 in the UniProt database (6 Jul. 2016) and comprises sequence SEQ ID NO: 1. Preferably, the functional equivalent variants of the HIV gag polypeptide show at least by 60%, 70%, 80%, 90%, 95%, 97%, 98% or 99% of the formation activity of its reference polypeptide. There are several techniques known in the art for evaluating the formation activity of the functionally equivalent variants of the VLPs according to the invention.

Accordingly, a functionally equivalent variant of the HIV gag polypeptide shows a degree of similarity of at least 50%, 55%, 60%, 65%, 70%, 75%, 80%, 85%, 90%, 95%, 96%, 97%, 98% or 99% with respect to the amino acid sequence of the corresponding native HIV gag polypeptide, provided the VLP formation ability of the protein is maintained. Preferably, the similarity exists over a region that is at least about 25 amino acids or nucleotides in length, or more preferably over a region that is 50-100 amino acids or nucleotides in length. An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically deemed substantially identical to a second polypeptide, for example, when the two peptides differ only by conservative substitutions. The degree of similarity between two peptides can be determined using computer algorithms and methods, which are widely known by the persons skilled in the art. The identity between two amino acid sequences of two peptides is preferably determined using the BLASTP algorithm. See Altschul, S, et al., "BLAST Manual", (NCBI NLM NIH Bethesda, Md. 20894, Altschul S, et al., J., 1990, Mol. Biol. 215:403-410). In a preferred embodiment, the degree of identity of the functionally equivalent variant with respect to gag is determined along the complete sequence of the variant, of gag or both.

In a preferred embodiment, the HIV gag polypeptide, or the functionally equivalent variant thereof, lacks the myristoylation sequence. Myristoylation is a lipidation modification where a myristoyl group derived from myristic acid, is covalently attached by an amide bond to the alpha-amino group of an N-terminal glycine residue. In the HIV gag polypeptide, the glycine susceptible to be myristoylated is the glycine in position 2 of SEQ ID NO: 1. The first methionine is removed by the host cell machinery. Preferably, the functionally equivalent variant of HIV gag lacking the myristoylation sequence comprises sequence SEQ ID NO: 2.

Any single-pass transmembrane protein may be used in the present invention. Examples include, but are not limited, to the transmembrane domain of CD22 (SEQ ID NO: 17), CD36 (SEQ ID NO: 18), CD44 (SEQ ID NO: 19) and the R696A mutant of HIV-1 Env (SEQ ID NO: 30). The capability of a sequence for forming a transmembrane domain can be analyzed by various assays known in the art.

In a preferred embodiment, the transmembrane domain is the transmembrane domain of the HIV gp41 polypeptide or a functionally equivalent variant thereof.

In a particular embodiment, the transmembrane region of the HIV gp41 polypeptide comprises sequence SEQ ID NO: 16

The fusion protein according to the invention comprises the immunogenic polypeptide located N-terminal to the HIV gag polypeptide, or the functionally equivalent variant.

The immunodominant polypeptide may comprise one or more epitopes. Generally, but not always, such immunodominant polypeptide or epitopes are highly immunogenic when tested according to methods that are known to those of skill in the art.

The proteins or peptides capable of inducing an immune response can be recombinant proteins or peptides, identical or similar to the natural antigens of a specific microorganism.

In a preferred embodiment, the polypeptide of interest comprises an immunogenic polypeptide. Preferably, the immunogenic polypeptide is a polypeptide capable of (suitable or designed for) inducing an immune response against an infectious disease in a subject, such as a disease caused by pathogenic microorganisms (e.g. virus, bacteria, fungi, mycoplasma, endo and ectoparasites). Preferably, the subject is a human being, a companion or farm animal. More preferably, the subject is human.

Viral pathogens include, but are not limited to, RNA viruses; DNA viruses; adenovirdiae (e.g. mastadenovirus, aviadeno virus); herpesviridae (e.g. herpes simplex virus 1, herpes simplex virus 2, herpes simplex virus 5, herpes simplex virus 6); leviviridae (e.g. levivirus, enterobacteria phase MS2, allolevirus); poxyiridae (e.g. chordopoxyirinae, parapoxvirus, avipoxvirus, capripoxvirus, leporipoxvirus, suipoxvirus, molluscipox virus, entomopoxyirinae); papovaviridae (e.g. polyomavirus, papillomavirus); paramyxoviridae (e.g. paramyxovirus, parainfluenza virus 1, mobillivirus (e.g. measles virus), rubulavirus (e.g. mumps virus); pneumonoviridae (e.g. pneumovirus, human RSV); metapneumovirus (e.g. avian pneumovirus, human metapneumo virus); picornaviridae (e.g. enterovirus, rhinovirus, hepatovirus (e.g. human hepatitis A virus), cardiovirus, apthovirus); reoviridae (e.g. orthoreo virus, orbivirus, rotavirus, cypo virus, fijivirus, phytoreo virus, oryzavirus); retroviridae (e.g. mammalian type B retroviruses, mammalian type C retroviruses, avian type C retroviruses, type D retrovirus group, BLV-HTLV retroviruses, lentivirus (e.g. HIV-1, HIV-2, spuma virus)); flaviviridae (e.g. hepatitis C virus); hepadnaviridae (e.g. hepatitis B virus); togaviridae (e.g. alphavirus (such as sindbis virus and rubivirus such as rubella virus); rhabdoviridae (e.g. vesiculovirus, lyssavirus, ephemera virus, cytorhabdovirus, necleorhabdovirus); arenaviridae (e.g. arenavirus, lymphocytic choriomeningitis virus, Ippy virus, lassa virus); and coronaviridae (e.g. coronavirus, torovirus); Cytomegalovirus (mononucleosis); Dengue virus (dengue fever, shock syndrome); Epstein-Barr virus (mononucleosis, Burkitt's lymphoma); Human T-cell lymphotropic virus type 1 (T-cell leukemia); Influenza A, B, and C (respiratory disease); Japanese encephalitis virus (pneumonia, encephalopathy); Poliovirus (paralysis); Rhinovirus (common cold); Rubella virus (fetal malformations); Vaccinia virus (generalized infection); Yellow fever virus (jaundice, renal and hepatic failure); and Varicella zoster virus (chickenpox). Examples of antigens of these viral pathogens include, hepatitis B surface antigen, rotavirus antigens such as VP4 and VP7, influenza virus antigens such as hemagglutinin or nucleoprotein and the thymidine kinase herpes simplex antigen.

The viral pathogens also include HIV antigens capable of generating an HIV-specific immune response. HIV antigens include, but are not limited to, peptides derived from HIV early regulatory proteins including HIV Tat, Rev and Nef (e.g. Nef-V3) proteins, or other HIV proteins such as Gag, Pol, Env, Vif, Vpr and Vpu. In particular, peptide epitopes of these proteins are those that are capable of generating neutralizing antibodies. Numerous HIV CTL/CD8+ and T-helper/CD4+ epitopes are known in the art and are contemplated for use in compositions effective for generating an HIV-specific immune response and are contemplated for use in the fusion proteins, VLPs and pharmaceutical compositions of the invention. See Korber B, et al., Eds., "HIV Molecular Immunology", (Los Alamos National Laboratory, Los Alamos, N. Mex., USA, 2006/2007).

Examples of specific viral pathogens which are important in veterinary medicine include, but are not limited to, Classical swine fever virus, PCV2 (postweaning multisystemic wasting syndrome) and Pseudorabies virus (Aujeszky's disease) (pigs); BHV-1 (bovine herpesvirus type 1) (cattle); Equine influenza virus and WNV (West Nile virus) (horses); Avian influenza virus (e.g. H5N1, HKN3), HTV (Turkey herpesvirus), MDV (Marek's disease virus) and IBDV (infectious bursal disease virus) and NVD (Newcastle disease virus) (poultry); Feline leukemia virus and Rabies virus (cats); and Canine coronavirus, Canine distemper virus, Canine parvovirus and IHN virus (dogs).

Bacterial pathogens include, but are not limited to, *Actinornyces israelli, Bacillus anthraces, Bacteroides* spp., *Bordetella pertussis, Borrelia burgdorferi, Brucella* spp., *Campylobacter* spp., *Campylobacter jejuni, Chlamydia* spp., *Chlamydia trachomatis, Clostridium botulinum, Clostridium perfringens, Clostridium tetani, Corynebacterium dipththeriae, Enterococcus* spp., *Erysipelothrix rhusiopathiae, Escherichia coli*, enterohemorrhagic *E. coli*, enterotoxigenic *E. coli, Fusobacterium nucleatum, Haemophilus influenzae* type B and non-typable, *Helicobacter pylori, Klebsiella pneumoniae, Legionella pneumophila, Leptospira* spp. *Listeria monocytogenes, Mycobacterium* spp. (e.g. *M. avium, M. gordonae, M. intracellulare, M. kansaii, M. leprae, M. tuberculosis*), *Mycobacterium tuberculosis, Neisseria gonorrhoeae, Neisseria meningitidis, Pasteurella* spp., *Pasteurella multocida, Pneumococcus* spp., *Pseudomonas aeruginosa, Rickettsia* spp., *Salmonella* spp., *Shigella* spp., *Staphylococcus aureus, Streptococcus* spp., *Streptococcus* (anaerobic species), *Streptococcus* (viridans group), *Streptococcus agalactiae* (*Streptococcus* Group B), *Streptococcus* B, *Streptococcus bovis, Streptococcus faecalis, Streptobacillus moniliformis, Streptococcus mutans, Streptococcus pneumoniae, Streptococcus pyogenes*, Group A beta hemolytic *Streptococcus, Treponema pallidum, Treponema pertenue, Vibrio cholera* and *Yersinia pestis.*

Examples of specific bacterial pathogens which are important in veterinary medicine include, but are not limited to, *Actinobacillus pleuropneumoniae* and *Lawsonia intrac-*

*ellularis* (pigs); *Anaplasma centrale, Anaplasma marginate, Brucella abortus, Brucella melitensis* and *Ehrlichia ruminantium* (cattle); *Streptococcus equi* (horses); *Chlamydophila abortus* (sheep); *Bordetella avium, Mycoplasma gallisepticum, Mycoplasma synoviae* and *Salmonella* spp. (poultry); *Aeromonas salmonicida, Vibrio anguillarum* and *Yersinia ruckeri* (fish); and *Porphyromonas gulae, Porphyromonas denticanis* and *Porphyromonas salivosa* (dogs).

Pathogenic fungi include, but are not limited to, the genera *Aspergillus, Blastomyces, Candida, Coccidiodes, Cryptococcus, Histoplasma, Phycomyces, Tinea corporis, Tinea unguis, Sporothrix schenckii* and *Pneumocystis carinii*. Specific examples of pathogenic fungi include, but are not limited to, *Blastomyces* dermatitides, *Candida albicans, Chlamydia trachomatis, Coccidioides immitis, Cryptococcus neoformans* and *Histoplasma capsulatum*.

Pathogenic parasites include, but are not limited to, the genera *Dirofilaria, Leishmania, Plasmodium, Schistosoma, Toxoplasma* and *Tripanosoma*. Specific examples of pathogenic parasites include, but are not limited to, *Dirofilaria immitis, Leishmania major, Leishmania donovani, Leishmania infantum, Leishmania braziliensis, Leishmania. panamensis, Leishmania mexicana, Plasmodium falciparum, Plasmodium malariae, Plasmodium ovale Plasmodium vivax, Toxoplasma gondii, Tripanosoma brucei* and *Tripanosoma cruzi*. Examples of specific antigens for these pathogenic parasites include *Plasmodium* spp. circumsporozoite antigen, *Plasmodium* spp. merozoite surface antigen and *Leishmania* spp. gp63.

Examples of specific pathogenic fungi and parasites which are important in veterinary medicine include, but are not limited to, *Babesia bigemina, Babesia bovis, Dictyocaulus viviparous, Fasciola gigantica, Fasciola hepatica, Neospora caninum, Theileria annulata, Theileria hirci* and *Theileria parva* (cattle); *Sarcocystis neurona* (horses); *Toxoplasma gondii* (sheep); *Eimeria* spp. (coccidiosis), *Eimeria maxima* and *Eimeria tenella* (poultry); and *Babesia canis, Giardia duodenalis* and *Leishmania donovani* (dogs).

In another preferred embodiment, the immunogenic polypeptide is a polypeptide associated with tumors or cancers ("tumor markers") capable of (suitable or designed for) inducing or modulating an immune response against a tumor or cancer cell. Therefore, the fusion proteins according to the invention could be used for the treatment or prevention of cancers by means of the stimulation of an antigen-specific immune response against a tumor antigen.

Over a thousand proteins are differentially expressed in human cancers and thus may serve as tumo rmarkers. Such proteins play a role in cancer-related processes including, but not limited to, angiogenesis, apoptosis, cell differentiation, cell signaling, hematopoiesis, hormonal control and immune reactions. Exemplary tumor markers include, but are not limited to, carcinoembryonic antigen (CEA) for both malignant pleural effusion and peritoneal cancer dissemination; human epidermal growth factor receptor 2 (HER-2/neu) for stage IV breast cancer; bladder tumor antigen for urothelial cell carcinoma; thyroglobulin for thyroid cancer metastasis; α-fetoprotein for hepatocellular carcinoma; prostate specific antigen (PSA) for prostate cancer; cancer antigen 125 (CA 125) for non-small cell lung cancer; cancer antigen 19.9 (CA 19.9) for pancreatic cancer; cancer antigen 15.3 (CA 15.3) for breast cancer; the combination of leptin, prolactin, osteopontin, and insulin-like growth factor II (IGF-II) for ovarian cancer; the combination of CD98, fascin, secreted chain of the polymeric immunoglobulin receptor (sPIgR), and 14-3-3 eta proteins for lung cancer; troponin I for myocardial infarction, and B-type natriuretic peptide for congestive heart failure.

Other common tumor markers include the estrogen receptor/progesterone receptor (ER/PR), HER-2/neu, and epidermal growth factor receptor (EGFR) for breast cancer, and tissue inhibitor of metalloproteinases (TIMP-1)-associated with serum HER2-positive breast cancer; Kirsten Ras oncogene (KRAS) and UDP glucuronosyltransferase family 1 member A (UGT1A1) for colorectal cancer; HER-2/neu for gastric cancer, c-KIT, CD20 antigen, CD30, and factoril interacting with PAPOLA and CPSF1-platelet-derived growth factor receptor alpha fusion protein (FIP1L1-PDGRF alpha), and platelet-derived growth factor receptor (PDGFR) for gastrointestinal stromal tumor (GIST); Philadelphia Chromosome (BCR/ABL)/PML/RAR alpha and anaplastic lymphoma kinase (TPMT/UGT1A1/ALK EGFR) for leukemia/lymphoma; KRAS/EGFR for lung cancer, and BRAF and S100 for melanoma.

Other examples of tumor markers include tumor suppressors that are lost in cancers, such as Breast Cancer Gene 1 (BRCA1), Breast Cancer Gene 2 (BRCA2); RNA such as mRNA, microRNA; proteins found in body fluids or tissue such as prostate specific antigen and CA-125; gene and protein based biomarkers; and nonspecific biomarkers such as glycosaminoglycans in body fluids; alkaline phosphatase and urinary hydroxyproline in skeletal involvement; hyaluronic acid excretion and urinary hydroxyproline in bone disease, and combinations thereof.

Tumor markers associated with important veterinary malignancies suchs as Canine malignant melanoma (CMM), the most common oral tumor in dogs and bovine ocular squamous cell carcinoma, can also be presented using the fusion proteins and VLPs of the invention.

In another preferred embodiment, the immunogenic polypeptide is a polypeptide capable of (suitable or designed for) inducing an immune response against an allergen.

Non-limiting illustrative examples of allergens include, but are not limited to, protein extracts of pollens from trees and flowers (e.g. *Lolium perenne, Poa pratense, Phleum pratense, Cynodon dactylon, Festuca pratensis, Dactylis glomerata, Secale cereale, Hordeum vulgare, Avena sativa, Triticum sativa, Artemisia vulgaris, Chenopodium album, Plantago lanceolata, Taraxacum vulgare, Parietaria judaica, Salsola kali, Urtica dioica, Olea europea, Platanus* spp., *Cupressus* spp), protein extracts of insects (e.g. *Dermatophagoides pteronyssinus, Dermatophagoides farinae, Acari* spp. (e.g. *Acarus siro*), *Blomia tropicalis, Euroglyphus maynei, Glyciphagus domesticus, Lepidoglyphus destructor, Tyrophagus putrescentiae*), protein extracts of fungi or of animal dander (e.g. *Penicillium* spp., *Alternaria alternata, Cladosporium herbarum*, dog dander, cat dander, horse dander) and protein extracts of food or food products.

In a preferred embodiment, the immunogenic polypeptide is from a protein of a virus. Preferably, the virus is HIV.

In a preferred embodiment, the immunogenic polypeptide does not contain an epitope from the HIV gag polypeptide.

In another preferred embodiment, the immunogenic polypeptide is from an Env protein of the HIV virus or a product results from the processing of the Env protein.

In a preferred embodiment, the sequence of the Env protein of HIV comprises SEQ ID NO: 20, or a functionally equivalent variant thereof.

In a preferred embodiment, the product resulting from the processing of the Env protein, is gp41, or a functionally equivalent variant.

The functional equivalent variants of the gp41 polypeptide have preferably at least 60%, 70%, 80%, 90%, 95%, 97%, 98% or 99% the formation activity of their reference polypeptide. The skilled person knows several techniques to detect VLP formation of a functional variant of an HIV gag polypeptide.

In a preferred embodiment, the gp41 variant sequence comprises SEQ ID NO: 5 and comprises the gp41 HR2 region and the MPER region.

In another preferred embodiment, the size of the immunogenic polypeptide has less than 90 amino acids, less than 80 amino acids, less than 70 amino acids or less than 60 amino acids.

In another preferred embodiment, the immunogenic polypeptide comprises from the N to C terminus:

(a) the HR2 region of the HIV gp41 polypeptide or a functionally equivalent variant thereof, and (b) the MPER region of the HIV gp41 polypeptide or a functionally equivalent variant thereof.

The gp41 HR1 and HR2 sequences are well known in the art. In a preferred embodiment, the HR2 region comprises SEQ ID NO: 21. Preferably, the MPER region comprises SEQ ID NO: 21, in the particular case of the HXB2 Env protein.

As modifications and changes may be made in the structure of the regions forming the gp41 variants according to the invention and still obtain molecules having like or otherwise desirable characteristics, such functional equivalents are also encompassed within the scope of the present invention.

For the purposes of the present invention, a polypeptide that is useful as an antigen in an immunogenic composition (i.e. has sufficient "immunogenic activity") can be identified by any method commonly known in the art for measuring the ability of a given polypeptide to trigger the generation of antibodies specific for said polypeptide when administered to a host organism. The ability of a given variant of the polypeptide according to the invention to be an immunologically equivalent variant may be determined using standard neutralization assays, wherein the suspected variant is inoculated into a test animal and the resulting antibodies are tested for their ability to neutralize the infection of susceptible cells by HIV strains.

Immunologically functional equivalents of the immunogenic polypeptide according to the invention can be obtained by modifying the polypeptide. Said modifications can be, without limitation, amino acid changes, deletions, truncations, polypeptide fragments, fusions to other polypeptides, insertions or any combination thereof. Accordingly, immunologically functional equivalents of the immunogenic polypeptide show a degree of identity with respect to the amino acid sequence shown of the corresponding region in the native immunogenic polypeptide of at least 50%, 55%, 60%, 65%, 70%, 75%, 80%, 85%, 90%, 95%, 96%, 97%, 98% or at least 99% provided that the immunogenic activity of the reference polypeptide is maintained. Preferably, the identity exists over a region that is at least about 25 amino acids or nucleotides in length, or more preferably over a region that is at least 50-100 amino acids or nucleotides in length. An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. The degree of identity between two peptides can be determined using computer algorithms and methods, which are widely known by the persons skilled in the art. The identity between two amino acid sequences of two peptides is preferably determined using the BLASTP algorithm. See Altschul, S. et al., "BLAST Manual", (NCBI NLM NIH Bethesda, Md. 20894, Altschul, S., et al., J., 1990, Mol. Biol. 215:403-410).

As an example of modifications contemplated to be within the scope of the present invention, certain amino acids may be substituted for other amino acids in a polypeptide structure without appreciable loss of interactive binding capacity of the structure such as, for example, the epitope of an antigen that is recognized and bound by an antibody. Since it is the interactive capacity and nature of a polypeptide that defines its biological (e.g. immunological) functional activity, certain amino acid sequence substitutions can be made in an amino acid sequence (or its underlying DNA coding sequence) and nevertheless obtain a polypeptide with comparable properties. Various changes may be made to the amino acid sequences of the antigens of the present invention without appreciable loss of immunogenic activity.

It is understood in the art that for making functionally equivalent amino acid substitutions, the hydropathic index of amino acids may be considered. The importance of the hydropathic amino acid index in conferring interactive biological function on a polypeptide is generally understood in the art. See Kyte J, et al., J. Mol. Biol. 1982; 15(1):105-132. It is known that certain amino acids may be substituted for other amino acids having a similar hydropathic index or score and still retain a similar biological activity. In making changes based upon the hydropathic index, the substitution of amino acids whose hydropathic indices are within plus or minus 2 is preferred, those which are within plus or minus 1 are particularly preferred, and those within plus or minus 0.5 are even more particularly preferred. Each amino acid has been assigned a hydropathic index on the basis of its hydrophobicity and charge characteristics; these are: isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9) and arginine (−4.5).

It is also understood in the art that the substitution of similar amino acids can be made effectively based on their hydrophilicity; particularly where the immunologically functional equivalent polypeptide thereby created is intended for use in immunological embodiments, as in certain embodiments of the present invention. The greatest local average hydrophilicity of a protein, as governed by the hydrophilicity of its adjacent amino acids, correlates with its immunogenicity and antigenicity. See Hopp T, U.S. Pat. No. 4,554,101. In making changes based upon similar hydrophilicity values, the substitution of amino acids whose hydrophilicity values are within plus or minus 2 is preferred, those which are within plus or minus 1 are particularly preferred, and those within plus or minus 0.5 are even more particularly preferred. The following hydrophilicity values have been assigned to amino acid residues: arginine (+3.0), lysine (+3.0), aspartate (+3.0 plus or minus 1), glutamate (+3.0 plus or minus 1), serine (+0.3), asparagine (+0.2), glutamine (+0.2), glycine (0), threonine (−0.4), proline (−0.5 plus or minus 1), alanine (−0.5), histidine (−0.5), cysteine (−1.0), methionine (−1.3), valine (−1.5), leucine (−1.8), isoleucine (−1.8), tyrosine (−2.3), phenylalanine (−2.5) and tryptophan (−3.4).

It is well known in the art that where certain residues are shown to be particularly important to the immunological or structural properties of a protein or peptide, like for example, residues in binding regions or epitopes, such residues may not generally be exchanged. In this manner, functional equivalents are defined herein as those polypeptides, which maintain a substantial amount of their native immunological activity. In general, the shorter the length of the molecule, the fewer changes can be made to the molecule without affecting its function. Longer domains may have an intermediate number of changes. The full-length protein will have the most tolerance for a larger number of changes. However, it must be appreciated that certain molecules or domains that are highly dependent upon their structure may tolerate little or no modification.

Immunologically equivalent variants can also be obtained by the expression from nucleic acid sequences which are substantially identical to the molecule encoding the regions in the native immunogenic polypeptide or their complements hybridize to each other under stringent conditions, as described below, provided that the immunogenic activity of the polypeptide encoded by said nucleic acids is preserved.

Stringent conditions are sequence-dependent and will be different in different circumstances. Longer sequences hybridize specifically at higher temperatures. See Tijssen S, "Overview of principles of hybridization and the strategy of nucleic acid assays", Laboratory Techniques in Biochemistry and Molecular Biology (Elsevier Science Publishers B.V., Amsterdam, N L 1993). Generally, stringent conditions are selected to be about 5-10° C. degrees lower than the thermal melting point (Tm) for the specific sequence at a defined ionic strength pH. The Tm is the temperature (under defined ionic strength, pH, and nucleic concentration) at which 50 percent of the probes complementary to the target hybridize to the target sequence at equilibrium (as the target sequences are present in excess, at Tm 50 percent of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50 percent formamide, 5×SSC and 1 percent SDS incubated at 42° C. or 5×SSC and 1 percent SDS incubated at 65° C., with a wash in 0.2×SSC and 0.1 percent SDS at 65° C.

A person skilled in the art will appreciate that the different components which form part of the fusion protein according to the present invention may be functionally linked directly or indirectly through a linker region.

In a preferred embodiment, the fusion protein according to the invention further comprises at least one linker. Preferably, the linker comprises glycine residues and, more preferably glycine and serine residues. Even more preferably, the linker comprises three glycine residues and one serine residue. Preferably, the linker comprises sequences SEQ ID NO: 23 or SEQ ID NO: 24. More preferably, the linker sequence is selected from the group consisting of sequences SEQ ID NO: 23 and SEQ ID NO: 24.

In another preferred embodiment, the fusion protein according to the invention further comprises a tag which may be used for the detection or for the purification of the gp41 variant using reagents showing specific affinity towards said tags. Adequate detection/purification tags includes hexa-his (metal chelate moiety), hexa-hat GST (glutathione 5-tranferase) glutathione affinity, calmodulin-binding peptide (CBP), strep-tag, cellulose binding domain, maltose binding protein, S-peptide tag, chitin binding tag, immuno-reactive epitopes, epitope tags, E2tag, HA epitope tag, Myc epitope, FLAG epitope, AU1 and AU5 epitopes, Glu-Glu epitope, KT3 epitope, IRS epitope, Btag epitope, protein kinase-C epitope, VSV epitope or any other tag as long as the tag does not affect the stability of the protein or the immunogenicity of the antigen attached thereto.

Several types of amino acid sequences may be added to the fusion proteins according to the invention to attain different objectives such as, for example, facilitating their handling or monitoring their expression. The addition of these peptide sequences to the fusion protein according to the invention does not affect their functional or immunogenic capabilities.

In a preferred embodiment, the linker sequence comprises sequences SEQ ID NO: 25, SEQ ID NO: 26 or SEQ ID NO: 27. Preferably, the linker sequence is selected from the group consisting of sequences SEQ ID NO: 25, SEQ ID NO: 26 and SEQ ID NO: 27.

In another preferred embodiment, the fusion protein according to the invention comprises sequence SEQ ID NO: 28.

3. Nucleic Acids, Vectors and Host Cells a) Nucleic Acids

In an additional aspect, the invention relates to a polynucleotide encoding a fusion protein according to the invention.

In a preferred embodiment, the polynucleotide according to the invention comprises sequence SEQ ID NO: 9.

In a preferred embodiment, the sequence of the polynucleotide according to the invention is codon-optimized according to the host selected for its expression. In another preferred embodiment, the codon-optimized sequence coding for the immunogenic polypeptide according to the invention comprises sequence SEQ ID NO: 11. In an additional preferred embodiment, the codon-optimized sequence coding for the HIV gag polypeptide according to the invention comprises sequence SEQ ID NO:13

Many methods and software tools for codon optimization are known to the skilled person. Codon-optimized nucleic acids for use according to the present invention can be prepared by replacing the codons of the nucleic acid encoding the immunogen by codons with appear with a high frequency in the selected host genome (e.g. "humanized" codons, codons that appear frequently in highly expressed human genes).

In a preferred embodiment, the codon-optimized polynucleotide according to the invention (i.e. human) comprises sequence SEQ ID NO: 14.

The polynucleotide of this invention can be operably linked to any promoter or enhancer capable of driving expression of the nucleic acid following introduction into a host cell. A promoter is an array of nucleic acid control sequences that directs transcription of a nucleic acid. A promoter includes necessary nucleic acid sequences (which can be) near the start site of transcription, such as in the case of a polymerase II type promoter (a TATA element). A promoter also can include distal enhancer or repressor elements which can be located as much as several thousand base pairs from the start site of transcription. Both constitutive and inducible promoters are included.

The polynucleotides according to the invention can be incorporated into a vector, for the purposes of cloning, performing other laboratory manipulations, manufacturing recombinant peptides or gene delivery.

b) Vectors

In a further aspect, the invention refers to a vector comprising a polynucleotide according to the invention.

A person skilled in the art will understand that there is no limitation regarding the type of vector that can be used with the present invention. The vector can be a cloning vector, suitable for propagation and for obtaining polynucleotides, gene constructs or expression vectors incorporated to several heterologous organisms. Thus, suitable vectors according to the present invention include prokaryotic expression vectors (e.g. pUC18, pUC19, Bluescript and their derivatives), mp18, mp19, pBR322, pMB9, CoIEl, pCR1, RP4, phages and shuttle vectors (e.g. pSA3 and pAT28), yeast expression vectors (e.g. vectors of the type of 2 micron plasmids), integration plasmids, YEP vectors, centromeric plasmids and the like, insect cell expression vectors (e.g. the pAC series and pVL series vectors), plant expression vectors, such as vectors of expression in plants (e.g. pIBI, pEarley-Gate, pAVA, pCAMBIA, pGSA, pGWB, pMDC, pMY, pORE series vectors), and eukaryotic expression vectors based on viral vectors (e.g. adenoviruses, viruses associated to adenoviruses as well as retroviruses and lentiviruses), as well as non-viral vectors such as pSilencer 4.1-CMV (Ambion, Applied Biosystems, Foster City, Calif., USA), pcDNA3, pcDNA3.1/hyg pHCMV/Zeo, pCR3.1, pEFl/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1. In a preferred embodiment, the vector is pcDNA3.1.

In a particular embodiments, the vector is an expression vector that can include a regulatory element, such as the cytomegalovirus hCMV immediate early gene, the early promoter of SV40 adenovirus, the late promoter of SV40 adenovirus, the lac system, the TAC system, the TRC system, the major operator and promoter regions of phage, the control regions of fd coat protein, the promoter for 3-phosphoglycerate kinase, the promoters of acid phosphatase or the promoters of the yeast mating factors. Exemplary vectors include, but are not limited to, bacterial artificial chromosomes, cosmids, yeast artificial chromosomes, phage, plasmids, lipid vectors and viral vectors (e.g. retrovirus). Suitable expression vectors for fusion protein have been previously described. See Kayman, U.S. Pat. No. 5,643,756.

c) Host Cells

In another aspect, the invention is directed to a host cell comprising the fusion proteins according to the invention, the polynucleotides encoding them or the vectors comprising said polynucleotides.

Cells suitable in the present invention include, without limitation, mammal, plant, insect, fungal and bacterial cells. Bacterial cells include, but are not limited to, Gram-positive bacterial cells such as species of the *Bacillus, Streptomyces* and *Staphylococcus* genus and Gram-negative bacterial cells such as cells of the *Escherichia* and *Pseudomonas* genus. Fungal cells preferably include yeast cells such as *Saccharomyces, Pichia pastoris* and *Hansenula polymorpha*. Insect cells include, but are not limited to, *Drosophila* cells and Sf9 cells. Plant cells include, among others, cells of crop plants such as cereals, medicinal, ornamental or bulbous plants. Mammalian cells include, but are not limited to, Chinese hamster ovary (CHO) cells such as CHO-K1 (ATCC accession number CCL-61), DG44 (Chasin L, et al., Som. Cell Mol. Genet. 1986; 12:555-556; and Kolkekar A, et al., Biochemistry 1997; 36:10901-10909), CHO-K1 Tet-On (Clontech, Mountain View, Calif., USA), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), CHO cells negative for dihydrofolate reductase (CHO/−DHFR, Urlaub G, et al., Proc. Natl. Acad. Sci. USA 1980; 77:4216-4220), SV40-transformed monkey kidney CV1 cells (COS, COS-7, ATCC accession number CRL-1651); human embryonic kidney cells (HEK-293, HEK-293T cells); baby hamster kidney cells (BHK, ATCC accession number CCL-IO); monkey kidney cells (CV1, ATCC accession number CCL-70); African Green Monkey kidney cells (VERO-76, ATCC accession number CRL-1587; VERO, ATCC accession number CCL-81); mouse Sertoli cells (TM4, Mather J, Biol. Reprod. 1980; 23:243-251); human cervical carcinoma cells (HELA, ATCC accession number CCL-2); dog kidney cells (MDCK, ATCC accession number CCL-34); human lung cells (W138, ATCC accession number CCL-75); human hepatoma cells (HEP-G2, HB 8065); mouse mammary tumor cells (MMT 060562, ATCC accession number CCL-51); buffalo rat liver cells (BRL 3A, ATCC accession number CRL-1442); TRI cells (Mather J, Ann. NY Acad. Sci. 1982, 383:44-68); MCR 5 cells and FS4 cells. Preferably, the host cells utilized are HEK-293T cells.

In a preferred embodiment, the host cell according to the invention is a recombinant bacterium.

In a preferred embodiment, the bacterium is a Gram-negative bacterial cell, and this term is intended to include all facultative Gram-negative cells of the family Enterobacteriaceace such as *Escherichia* spp., *Shigella* spp., *Citrobacter* spp., *Salmonella* spp., *Klebsiella* spp., *Enterobacter* spp., *Erwinia* spp., *Kluyvera* spp., *Serratia* spp., *Cedecea* spp., *Morganella* spp., *Hafhia* spp., *Edwardsiella* spp., *Providencia* spp., *Proteus* and *Yersinia* spp.

All the terms and embodiments previously described in relation to the fusion proteins the invention are equally applicable to polynucleotides, vectors or host cells according to the invention.

4. Method of Preparing VLPs

In a still further aspect, the invention relates to a method for preparing a VLP loaded with a polypeptide of interest comprising:

(a) expressing in a cell a fusion protein according to the invention, and (b) recovering the VLP from the extracellular medium.

The first step of the method according to the invention comprises the transformation of a host cell with a vector comprising the polynucleotide according to the invention. Said transformation can be carried out by conventional techniques that are well known to those of ordinary skill in the art. Where the host is prokaryotic, such as *E. coli*, competent cells which are capable of DNA uptake can be prepared from cells harvested after exponential growth phase and subsequently treated by the $CaCl_2$) method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes or virus vectors can be used. Eukaryotic cells can also be co-transformed with polynucleotide sequences encoding an immunogenic gp120 polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein The cell culture should be maintained under suitable conditions to allow the polynucleotide according to the invention to be expressed.

The second step of the method according to the invention comprises recovering the VLP from the extracellular medium, for example by centrifugation and filtration through 0.45 μm filters.

In the case of the VLPs obtained using the fusion proteins according to the invention, the VLPs are characterized for having a viral capsid enclosed by a lipidic envelope, which lipid envelope is derived from the cell that formed the VLP.

In another aspect, the invention relates to a virus like-particle comprising the fusion protein according to the invention or obtained using the method according to the invention.

All the terms and embodiments previously described are equally applicable to the method for preparing a VLP according to the invention and to the VLP according to the invention.

5. Pharmaceutical Compositions

In a further aspect, the invention refers to a pharmaceutical composition comprising a fusion protein, a polynucleotide, a vector, a host cell or a virus-like particle according to the invention, or a combination thereof.

The pharmaceutical composition according to the invention may further comprise a pharmaceutically acceptable carrier.

A pharmaceutically acceptable carrier is essentially non-toxic to recipients at the dosages and concentrations employed, and is compatible with other ingredients of the formulation. For example, the carrier for a formulation containing polypeptides would not normally include oxidizing agents and other compounds that are known to be deleterious to polypeptides. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation.

The pharmaceutical composition according to the invention can be administered by any means known to one skilled in the art, such as by intramuscular, subcutaneous or intravenous injection, and oral, nasal, or anal administration. See Banga A, "Parenteral Controlled Delivery of Therapeutic Peptides and Proteins," in Therapeutic Peptides and Proteins (Technomic Publishing Co., Inc., Lancaster, Pa., USA, 1995). The polypeptide of interest according to the invention can be provided as an implant, an oily injection or as a particulate system to prolong it therapeutic benefits (e.g. increase immunogenic response). The particulate system can be a microparticle, a microcapsule, a microsphere, a nanocapsule or similar particle. See Banga, 1995, supra. Preferably, the pharmaceutical compositions according to the invention are administered parenterally.

The pharmaceutical compositions according to the invention can be formulated in unit dosage form, suitable for individual administration of precise dosages. A therapeutically effective amount of pharmaceutical composition can be administered in a single dose, or in multiple doses, for example daily, during a course of treatment or as part of a prevention protocol. In specific, non-limiting examples, pulse doses of a pharmaceutical composition according to the invention include at least daily, at least weekly and at least monthly administration regimens. The dosage, frequency and route of administration of the pharmaceutical composition may be varied by the skilled person according to the needs of the subject and following the applicable protocols in human and veterinary medicine.

The therapeutically effective amount of the pharmaceutical composition according to the invention can depend on the severity of the disease and the age, weight, general state of the subject, and other clinical factors, such as the subject's sensitivity to the polypeptide of interest. Thus, the final determination of the appropriate treatment regimen will be made by the attending clinician. Typically, dosages used in vitro can provide useful guidance in the amounts useful for in situ administration of the pharmaceutical composition, and animal models may be used to determine effective dosages for treatment of particular disorders. See Gilman R, et al., Eds., Goodman and Gilman's: The Pharmacological Basis of Therapeutics, 8th Ed. (Pergamon Press, New York, N.Y., US, 1990), and Gennaro A, Ed., Remington's Pharmaceutical Sciences, 18th Ed. (Mack Publishing Co., Easton, Pa., US, 1990). Typically, the dose range is from about 0.1 μg/kg body weight to about 100 mg/kg body weight. Other suitable ranges include doses of from about 1 μg/kg to 10 mg/kg body weight. In one example, the dose is about 1.0 μg to about 50 mg, for example, 1 μg to 1 mg, such as 1 mg peptide per subject.

a) Immunogenic or Vaccine Compositions

In a preferred embodiment, the pharmaceutical composition according to the invention is an immunogenic or vaccine composition. Said immunogenic or vaccine composition comprises a therapeutically effective amount a fusion protein, a polynucleotide, a vector, a host cell or a virus-like particle according to the invention, or a combination thereof.

The immunogenic or vaccine composition according to the invention may further comprise a pharmaceutically acceptable carrier and other excipients such as adjuvant. Examples of adjuvant that can be used with the immunogenic or vaccine compositions according to the invention include, but are not limited to, $AlK(SO_4)_2$, $AlNa(SO_4)_2$, $AlNH_4(SO_4)$, silica, alum, $Al(OH)_3$, $Ca_3(PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2 percent squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium tuberculosis*, substances found in *Corynebacterium parvum, Bordetella pertussis*, and members of the genus *Brucella* spp., Titermax, ISCOMS, Quil A, ALUN, Lipid A derivatives, choleratoxin derivatives, HSP derivatives, LPS derivatives, synthetic peptide matrixes or GMDP, interleukin 1, interleukin 2, Montanide ISA-51 and QS-21, CpG oligonucleotide, poly I:C and GM-CSF. See Hunter, U.S. Pat. No. 5,554,372, and Jager, WO1997028816. A particulate carrier based on a synthetic polymer has been shown to act as an adjuvant to enhance the immune response, in addition to providing a controlled release. Aluminum salts can also be used as adjuvants to produce an immune response.

In a preferred embodiment, the immunogenic or vaccine composition according to the invention comprises a therapeutically effective amount of the virus-like particles according to the invention and is devoid of adjuvant. In a more preferred embodiment, the immunogenic or vaccine composition according to the invention is essentially free from aluminum phosphate.

The immunogenic or vaccine compositions according to the invention can be administered whenever its therapeutic effect is desired (e.g. decreased signs, symptoms, or laboratory results of HIV-1 infection). Generally, the dose is sufficient to treat or ameliorate symptoms or signs of disease without producing unacceptable toxicity to the subject. Systemic or local administration can be utilized. The immunogenic or vaccine compositions may be administered to a subject according to a prime/boost protocol, whereby a first administration of the composition is followed by at least one second administration at a different date using the same or a different dosage to reinforce or maintain the subject's immune response against the polypeptide of interest (i.e. immunogen).

All the terms and embodiments previously described are equally applicable to the immunogenic composition or the vaccine composition according to the invention.

6. Therapeutic Methods

In another aspect, the invention is directed to a fusion protein, a polynucleotide, a vector, a host cell, a virus-like particle or a pharmaceutical composition according to the invention, or combination thereof, for use in medicine. In a preferred embodiment, the fusion protein, polynucleotide, vector, host cell, virus-like particle or pharmaceutical composition according to the invention, or combination thereof, is for use in human medicine. In another preferred embodiment, the fusion protein, polynucleotide, vector, host cell, virus-like particle or pharmaceutical composition according to the invention, or combination thereof, is for use in veterinary medicine.

In a still further aspect, the invention relates to a fusion protein, a polynucleotide, a vector, a host cell, a virus-like particle or a pharmaceutical composition according to the invention, or combination thereof, for use in the treatment or prevention of a disease caused by an infection or tumor in a subject. In a preferred embodiment, the subject is a human being. In another preferred embodiment, the subject is a farm or companion animal. In an alternative form of this aspect, the invention relates to a method of treating or preventing a disease caused by an infection or tumor in a subject which comprises the administration of a therapeutically effective amount of a fusion protein, a polynucleotide, a vector, a host cell, a virus-like particle or a pharmaceutical composition according to the invention, or combination thereof, to a subject. In a further alternative form of this aspect, the invention refers to the use of a fusion protein, a polynucleotide, a vector, a host cell, a virus-like particle or a pharmaceutical composition according to the invention, or combination thereof, in the manufacture of a medicament for the treatment or prevention of a disease caused by an infection or tumor in a subject.

In an additional aspect, the invention relates to a fusion protein, a polynucleotide, a vector, a host cell, a virus-like particle or a pharmaceutical composition according to the invention, or combination thereof, for use in the delivery of therapeutic agents to cells or in diagnosis.

In a preferred embodiment, the polypeptide of interest is an HIV polypeptide. In a more preferred embodiment, the HIV polypeptide comprises the MPER region of gp41 or a functionally equivalent variant thereof. Preferably, the subject is a human, chimpanzee, macaque or baboon. More preferably, the subject is a human.

Other diseases that may be treated or prevented using the fusion proteins, polynucleotides, vectors, host cells, virus-like particles or pharmaceutical compositions according to the invention, or their combinations, include infectious diseases caused by viruses, bacteria, fungi, protozoa and parasites. Examples of virus or viral infections that may be treated or prevented by using the fusion proteins, polynucleotides, vectors, host cells, virus-like particles or pharmaceutical compositions according to the invention, or their combinations, include, but are not limited to, adenovirus, cytomegalovirus, Epstein-Barr virus, hanta virus, dengue, hepatitis A, hepatitis B, hepatitis C, herpes simplex type I, herpes simplex type II, human immunodeficiency virus (HIV), human papilloma virus (HPV), influenza, measles, mumps, papova virus, polio, respiratory syncytial virus, rinderpest, rhinovirus, rotavirus, rubella, SARS virus, smallpox and viral meningitis. Examples of suitable bacteria or bacterial infection include, but are not limited to, *Bacillus antracis, Borrelia burgdorferi, Campylobacter jejuni, Chlamydia trachomatis, Clostridium botulinum, Clostridium tetani, Diptheria* spp., *E. coli, Legionella* spp., *Helicobacter pylori, Mycobacterium rickettsia, Mycoplasma nesisseria, Pertussis* spp., *Pseudomonas aeruginosa, S. pneumonia, Streptococcus* spp., *Staphylococcus* spp., *Vibria cholerae* and *Yersinia pestis*. Examples of suitable fungi or fungal infections include, but are not limited to, *Aspergillus fumigatus, Blastomyces dermatitides, Candida albicans, Coccidioides immitis, Cryptococcus neoformans, Histoplasma capsulatum* and *Penicillium marneffei*. Examples of suitable protozoa and parasites or fungi or protozoal and parasitic infections include, but are not limited, *Chlamydia* spp., *Leishmania* spp., *Plasmodium* spp. (e.g. malaria), *Rickettsia* spp. and *Trypanosoma* spp.

The fusion proteins, polynucleotides, vectors, host cells, virus-like particles or pharmaceutical compositions according to the invention, or their combinations, could also be useful for counteracting pathogens involved in bioterrorism such as, for example, *Botulinum toxin, Bacillus anthraces, Clostridium perfringens, Bacillus subtilus, Bacillus thuringiensis*, hemorrhagic conjunctivitis virus (Enterovirus 70) and rotavirus.

The fusion proteins, polynucleotides, vectors, host cells, virus-like particles or pharmaceutical compositions according to the invention, or their combinations, could be additionally useful for the treatment or prevention of chronic conditions, such as Alzheimer's disease, Parkinson's disease and rheumatoid arthritis or other conditions, such as allergies and tumors. An example of the latter could consist of a chimeric protein simultaneously including antibodies or fragment of antibodies against tumoral markers or radioactive elements for radiotherapy. The fusion proteins according to the present invention, and the antibodies derived elicited by from them, could also be used for the diagnosis of fertility and pregnancy, or of diseases such as colon, lung, breast and prostate cancer. These fusion proteins could also be used to monitor and control drug abuse or the progress of therapeutic treatments.

The present invention further relates to preventing or reducing symptoms associated with HIV infection. These include symptoms associated with the minor symptomatic phase of HIV infection, including, for instance, shingles, skin rash and nail infection, mouth sores, recurrent nose and throat infection and weight loss. In addition, further symptoms associated with the major symptomatic phase of HIV infection, include, for example, oral and vaginal thrush (*Candida*), persistent diarrhea, weight loss, persistent cough, reactivated tuberculosis, and recurrent herpes infections, such as cold sores (herpes simplex). Symptoms of full-blown AIDS which can be treated in accordance with the present invention, include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii* pneumonia (PCP), herpes zoster (or shingles), nervous system problems, such as pains, numbness or "pins and needles" in the hands and feet, neurological abnormalities, Kaposi's sarcoma, lymphoma, tuberculosis, and other opportunistic infections.

The fusion proteins, polynucleotides, vectors, host cells, virus-like particles, and pharmaceutical compositions according to the invention, or their combination, can induce the expression of antibodies in a subject. In one embodiment, the antibodies are neutralizing antibodies (i.e. nAbs). In a preferred embodiment, the fusion proteins, polynucleotides, vectors, host cells, virus-like particles, and pharmaceutical compositions according to the invention, or their combination, are used for preventing HIV infection or AIDS in a non-infected subject under HIV exposure.

The fusion proteins according to the invention may also have multiple uses in the breeding of companion and farm animals and fish. These fusion proteins may be used to prepare immunogenic or vaccine compositions against animal retroviruses, such as Feline Leukemia Virus (FeLV), but also against non-viral pathogens such as *Brucella* spp., a bacterial agent that causes many problems in cattle, or against *Piscirickettsia salmonis*, which affects mainly the commercial breeding of salmon. Other possible uses of the fusion proteins according to the invention are the preparation of vaccines against *Mycoplasma hyopneumoniae*, a pneumonic agent that produces great losses in pigs. It would also be possible to use the fusion proteins according to the invention for modulating the expression of certain hormones to accelerate the growth rate and increase the production of milk, in farming animals, or make their meat leaner. An example of these non-conventional indications would be the use of these entities for the immunocastration of farm animals, such like pigs.

Typically, the neutralizing antibodies used in the method of the present invention bind to the surface of the pathogen and inhibit or reduce infection by the pathogen by at least 99%, 95%, 90%, 85%, 80%, 75%, 70%, 60%, 50%, 45%, 40%, 35%, 30%, 25%, 20% or 10% relative to the infection by the pathogen in the absence of said antibody(ies) or in the presence of a negative control. The nAbs can then be tested to determine if they are broadly neutralizing (i.e. bnAbs) using any of the methods provided herein. If the nAbs or bnAbs were raised in a non-human animal, the CDRs or the complete sequence can be transferred from the non-human framework to a human framework to generate an antibody suitable for administration to a human. Methods for determining whether an antibody is a nAb have been described in the art. See Li M, et al., J. Virol. 2005; 79:10108-10125, Wei X, et al., Nature 2003; 422:307-312, and Montefiori D, Curr. Protoc. Immunol. 2005; January, Chapter 12:Unit 12.11. These methods are based on the determination of the reduction in expression of a reporter gene after a single round of viral infection using a receptive cell line using a virus which encodes the reporter gene.

In another preferred embodiment the fusion protein, the polynucleotide, the vector, the host cell or the virus like-particle is for use according to the invention, wherein the subject is previously treated with a conjugate comprising the immunogenic polypeptide forming part of the fusion protein coupled to a carrier.

In a preferred embodiment, the immunogenic polypeptide corresponds to any region of HIV gp41 polypeptide or a functionally equivalent variant thereof. Preferably, the region is the MPER region. More preferably, the MPER region comprises SEQ ID NO: 22.

In another preferred embodiment, the carrier is KLH (Keyhole Limpet hemocyanin)

7. Kits

In a further aspect, the present invention refers to kits comprising at least one of the fusion proteins, polynucleotides, vectors, host cells, virus-like particles or pharmaceutical compositions according to the invention, or a combination thereof. The components of the kits according to the invention may be optionally packed in suitable containers and be labeled for their intended use, including the treatment or prevention of infectious diseases. In one embodiment, the infectious disease is HIV, AIDS or their related diseases or conditions. The components of the kits may be stored in unit or multi-dose containers as an aqueous, preferably sterile, solution or as a lyophilized, preferably sterile, formulation for reconstitution. The containers may be formed from a variety of materials such as glass or plastic and may have a sterile access port (e.g. the container may be an intravenous solution bag or a vial having a stopper pierceable by a hypodermic injection needle). The kits may further comprise more containers comprising a pharmaceutically acceptable carrier. They may further include other materials desirable from a commercial and user standpoint, including, but not limited to, buffers, diluents, filters, needles, syringes, culture medium for one or more of the suitable host cells or other active agents. The kits can contain instructions customarily included in commercial packages for therapeutic products that contain information, for example, about the indications, usage, dosage, manufacture, administration, contraindications or warnings concerning the use of such therapeutic products.

All publications mentioned herein are incorporated in their entirety by reference. Having now generally described the invention, the same will be more readily understood through reference to the following examples, which are provided by way of illustration and are not intended to be limiting of the present invention, unless specified.

General Procedures

1. Expression Vectors for Small Gp41-Derived Proteins, Gag and Fusion Proteins The pMIN mammalian expression plasmid coding for a small protein containing the C-terminal HR2 region, the MPER and TM domain has been described previously. See Molinos-Albert L, et al., Retrovirology 2014, 11:44. A similar plasmid pMINFULL coding for a gp41-derived protein that contains the MIN sequence and the cytoplasmic tail of gp41 was also generated. See FIG. 1. MIN sequence was cloned in a pET-21D+ expression vector (Novagen, Merck KGaA, Darmstadt, DE) for *E. coli* production of recombinant proteins.

Gag sequences were amplified from the pGag-EGFP plasmid that codes for a Rev-independent HIV-1 Gag protein fused in frame to the enhanced GFP. The plasmid was obtained from the NIH AIDS Reagent Program (Cat No. 11468). See Dhillon A, et al., J. Virol. 2007; 81:6548-6562. The gag amplicon was subcloned in frame into a pcDNA3.1MIN plasmid to generate the pcDNA3.1/MIN-GAG-3.7 plasmid that codes for the fusion protein MIN-GAG. A pGAG plasmid coding for the full Gag sequence was generated by excision of the gag coding sequence from the pGag-EGFP plasmid and subcloning in a pcDNA3.1 plasmid (Invitrogen, Carlsbad, Calif., USA; Cat. Nos. K4900-01, K4900-40) See FIG. 1. All amplification reactions were performed using Platinum™ Taq DNA Polymerase High Fidelity (Thermo Fisher Scientific, Waltham, Mass., USA) in a 2720 Thermal cycler (Applied Biosystems, Foster City, Calif., USA). All plasmids were sequenced to confirm the expected sequence and insertion sites.

2. Peptides, Gp41-Derived Proteins and VLP

The C34, T-20 and MPER peptides (HXB2 sequence) and Keyhole Limpet hemocyanin (KLH) and MPER coupled to KLH (KLH-MPER) were employed (Thermo Fisher Scientific, Waltham, Mass., USA). 15-mer overlapping peptides covering the gp41 HR2 and MPER regions were kindly provided by C. Brander (IrsiCaixa, Badalona, ES). The MIN protein containing a C-terminal 6×His tag was produced in *E. coli* BL21 DE3 strain (Invitrogen, Thermo Fisher Scientific, Waltham, Mass., USA). See FIG. 1A. Inclusion bodies were obtained from a 1 L culture bacterial extract and solubilized by using an 8M urea solution. Highly pure protein was obtained through niquel-based Immobilized Metal Affinity Chromatography (GE Healthcare, Inc., Stamford, Conn., USA) and gel filtration using a Sephacryl S-200 HR column (GE Healthcare, Inc., Stamford, Conn., USA).

VLP were obtained by transfection of different derivatives of HEK-293T cells according to the production scale. For stable transfection, we transfected HEK-293T cells with pMINFULL and pGAG, pGAG or pcDNA3.1/MINGAG-3.7 using calphos mammalian transfection kit (Clontech®, Takara Bio Inc., Otsu, JP), and selected the transfected cells by using geneticine plus hygromicine, hygromicine or geneticine, respectively.

Given the poor yield of MINGAG VLPs, large scale production of GAG and MINGAG VLPs was carried out in a different setting. Large amounts of the pcDNA3.1/MIN-GAG-3.7 expression plasmid were produced using maxiprep kits (Qiagen NV, Venlo, NL) and were used for transient transfection of HEK-293T cells. Gag VLP were produced in 1 L culture flask, while MINGAG VLP were produced in a 5 L bag. 48 hours after transfection, supernatants were collected, ultrafiltered, concentrated (to 1 L in the case of MINGAG) and ultracentrifuged. Both preparations contained large amounts of gag protein as assessed by Nanoparticle Tracking Analysis (NTA, NanoSight Ltd., Malvern, GB) and electron microscopy.

3. Antigenicity Studies

To evaluate the antigen exposure on the surface of VLPs, HEK-293T cells were transfected with fusion proteins including the extracellular epitope of interest and the full HIV gag sequence. 24 hours after transfection cells were harvested and stained with specific antibodies against cell surface antigens (anti gp41 antibodies 2F5, 4E10 or 10E8 or specific antibodies against other proteins of interest), after washing the excess of antibody, cells were fixed and permeabilized using FIX and PERM® Cell Fixation and Cell Permeabilization Kit (Thermo Fisher Scientific, Waltham, Mass., USA) and intracellularly stained with the anti-gag antibody Kc57 (Beckman Coulter, Brea Calif., USA). After a final wash, cells were analyzed in a LSRII flow cytometer (BD Biosciences, San Jose, Calif., USA). The frequency of cell-surface antigen positive cells among GAG positive cells was used as a measure of antigen exposure.

4. Immunogenicity Studies

Female C57BL/6 mice (Harlan Sprague Dawley Inc., Indianapolis, Ind., USA) aged 6-8 weeks were used for murine immunization protocols. Groups of mice (5 mice per group) were immunized subdermally with 50 μg of recombinant proteins or VLPs at 3-week intervals. Blood samples were collected by maxillary artery puncture before immunization and at 3 weeks. Mice were observed daily to record body weight changes.

For rabbit immunization, 3- to 4-month-old New Zealand White rabbits were inoculated subcutaneously with different immunogens. A control rabbit group (n=4) was primed with full gag DNA and nude VLP, and the immunized twice at weeks 0 and 3 with nude VLP. A second group of rabbits (n=4) was primed with DNA coding for the HTI immunogen, full HIV gag and full HIV env genes and then immunized at week 0 and 3 with MINGAG VLP. See Mothe B, et al., J. Transl. Med. 2011; 9:208. Sera were collected at weeks 1, 3, 4 and at sacrifice.

All animal and husbandry experiments were conducted according to the applicable rules and regulations.

5. Enzyme-Linked Immunosorbent Assays (ELISA)

Peptides C34, T20, MPER, overlapping 15mer gp41 peptides or recombinant GAG or MIN protein were used to coat 96-well Maxisorp Nunc-immuno plates (Thermo Fisher Scientific, Waltham, Mass., USA). After blocking, plates were incubated with 100 μL of previously diluted plasma samples overnight at 4° C. Plates were then washed and 100 μL of a horseradish peroxidase (HRP)-conjugated F(ab)2 goat anti-mouse IgG (Fc specific, Jackson ImmunoResearch Labs, Inc., West Grove, Pa., USA) were dispensed for one hour at room temperature. Plates were developed with 100 μl of 0-phenylenediamine dihydrochloride (OPD) substrate (Sigma-Aldrich, Saint Louis, Mo., USA) and stopped with 100 μL of 4N H2504. Optical density was measured at 492 nm for specific signal and at 620 nm for background.

6. Viruses and Neutralization Assays

HIV-2 chimeras were made in the context of the full-length p7312A HIV-2 molecular clone (GenBank accession number L36874). Expression vectors for the wild type HIV-2 (p7312A) and HIV-2 chimeras containing the HIV-1 gp41 MPER (p7312A-C1), the 2F5 (p7312A-C3) or 4E10 epitopes (p7312A-C4), were kindly provided by G. M. Shawn (University of Pennsylvania). See Dhillon, 2007, supra. Pseudoviruses were generated by transfection of plasmids in HEK-293T cells. After 24 hours post-transfection, supernatants were harvested, filtered at 0.45 micron and viral stocks frozen at −80° C.

HIV-1 isolates NL4.3, BaL, AC10 and SVPB16 were generated as pseudoviruses using Env expression plasmids and the pSG3 vector as previously described. See Sanchez-Palomino S, et al., Vaccine 2011, 29:5250-5259. Cell-free virus neutralization by plasma samples was tested by a standard TZM-b1 based assay. See Sanchez-Palomino S, 2011, supra. Vaccine 2011, 29:5250-5259. Briefly, in a 96-well culture plate, 100 μL of previously diluted plasma samples were preincubated with 50 μL of pseudovirus stock, using 200 TCID50, at 37° C., one hour. Then, 100 μL containing 10,000 TZM-b1 luciferase-reporter target cells per well were added. Plates were cultured at 37° C. and 5% CO2 for 48 hours. 2F5, 4E10 and IgGb12 (Polymun Scientific GmbH, Klosterneuburg, AT), and anti-CD4 clone SK3 (BD Biosciences Corp., Franklin Lakes, N.J., USA) were used as controls. Plasma samples were inactivated (56° C., 30 minutes) prior to the assay. TZM-b1 reporter cells were treated with dextran (Sigma-Aldrich, Saint Louis, Mo., USA) to enhance infectivity. Luciferase substrate, Britelite Plus (PerkinElmer, Inc., Waltham, Mass., USA) was used for the read out of HIV infectivity.

Example 1

Generation of VLP Presenting HIV MPER Epitopes

Figure 2:
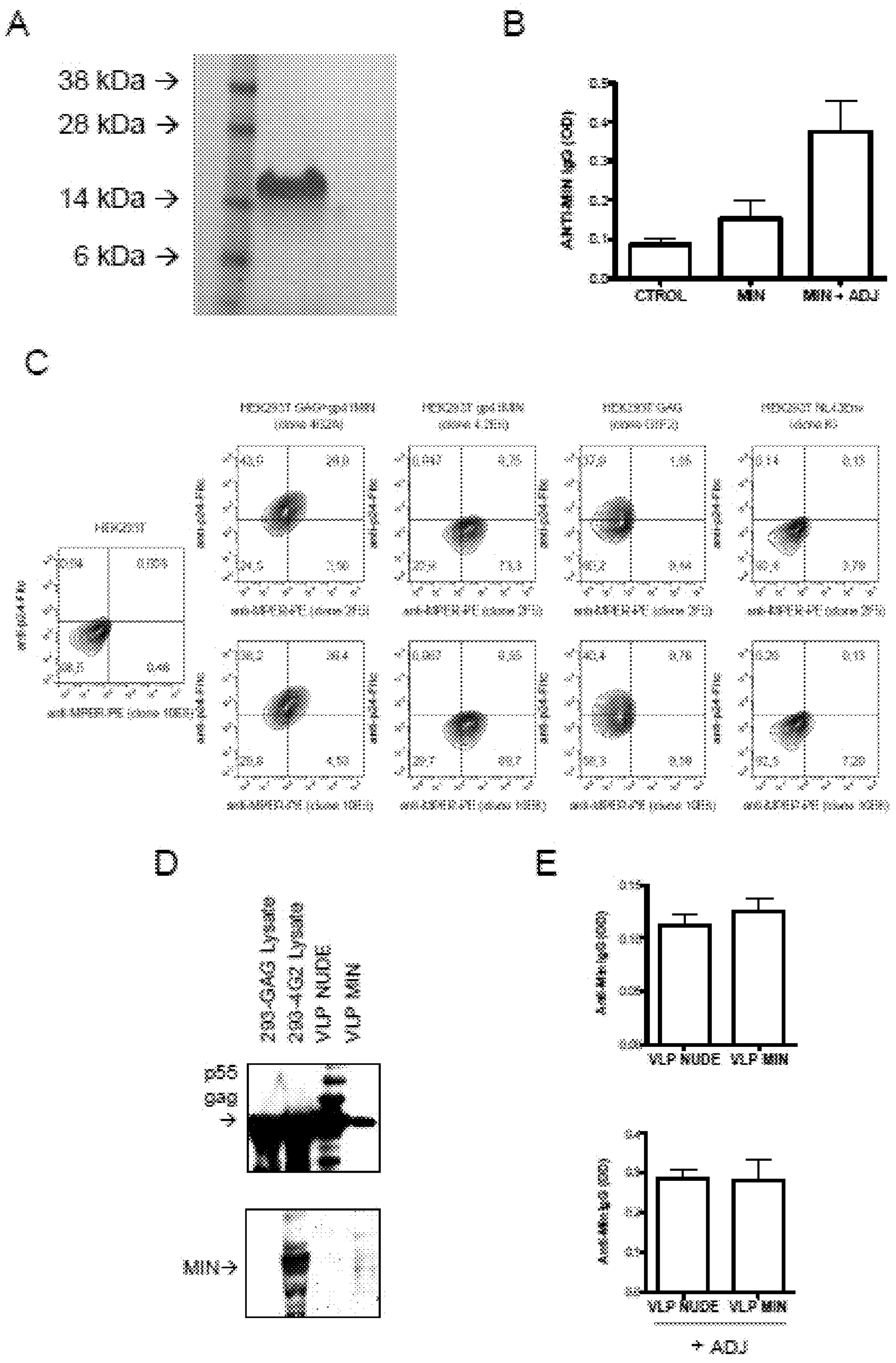
FIG. 2. Characterization and immunogenicity of soluble MIN and MIN-VLPs obtained by cotransfection. (A) The soluble MIN protein was expressed in *E. coli* and purified to homogeneity by $Ni^{2+}$ affinity and gel filtration chromatography. The final preparation contained a single 17 kDa band. Molecular weight markers are shown on the left. (B) The immunogenicity of soluble MIN preparations was tested in C57BL/6 mice. ELISA data against the MIN protein for sera (1/100 dilution) from control animals or animals immunized with MIN (50 μg/dose) with or without aluminum phosphate are shown. (C) HEK-293T cells stably transfected to express Env glycoprotein (NL4.3 isolate, clone K) (right), GAG (clone G1F2), MIN (clone, 4.2E6) or both Gag and MIN (left, clone 4G2A) were stained for cell surface expression of MPER epitopes and for intracellular expression of CA-p24 protein (Gag). Un-transfected HEK-293T cells were included as negative control. Flow cytometry analysis is shown. (D) Cell pellets and supernatants from HEK-293T G1F2 (expressing Gag) and HEK-293T 4G2A cells (co-expressing both Gag and MIN) were analyzed by WB using an anti-p24 antibody (upper) and the anti-MPER antibody 2F5 (lower). (E) In parallel, the immunogenicity of MIN-VLP preparations was tested in C57BL/6 mice. ELISA data against the MIN protein for sera (1/100 dilution) from control animals or animals immunized with MINVLPs (50 μg total protein/dose) with or without aluminum phosphate are shown.

The MIN protein was selected due to its high expression and proper MPER exposure on the cell-surface of transfected cells. See Molinos-Albert, 2014, supra. As a first approach to test its potential immunogenicity, both the recombinant MIN protein and the VLP displaying the selected MIN protein were produced. See FIG. 1. For the recombinant MIN protein, production was carried out in *E. coli* and protein was purified to homogeneity, showing the expected 17 kDa molecular weight. See FIG. 2A. The immunogenicity of the recombinant MIN protein was assayed in C57BL/6 mice. Animals immunized with recombinant preparation of MIN (3 doses, 20 μg each) showed IgGs reactive against this protein. The reactivity of these IgGs was increased by the presence of aluminum phosphate as adjuvant. See FIG. 2B.

For VLPs, the cytoplasmic domain of gp41 was added to the MIN sequence (MINFULL construction) in order to increase the interaction with Gag during VLP budding. A HEK-293T cell clone stably expressing both MINFULL and GAG HIV-1 proteins was selected according to protein expression and VLP production. The selected clone (4G2A) showed cell surface MPER exposure and an intracellular GAG content comparable to a GAG expressing HEK-293T cell clone selected in parallel and lacking gp41 expression. See FIG. 2B. Supernatants from these clones contained gag protein mostly in a high molecular weight form (>300 kDa) suggesting the proper formation of VLP. This observation was further confirmed by the WB analysis of centrifuged VLP and cellular lysates that contained GAG protein in control cells and both GAG and GP41 proteins in the MINFULL and GAG co-expressing cells. See FIG. 2C. In immunogenicity assays, C57BL/6 mice immunized with MIN-VLPs (three doses 10 μg of total protein each) in the presence or absence of adjuvant (aluminum phosphate) showed non-significant anti gp41 IgG response compared to control animals although a high reactivity against HEK-293T cell surface proteins and HIV-1 GAG antigen could be readily detected. See FIG. 2E. Furthermore, no significant anti-HIV-1 neutralizing activity was detected in any animal, either immunized with MIN recombinant protein or VLP, when assayed against a mini panel of four viruses (i.e. NL4-3, BaL, AC-10 and SVBP16).

Example 2

Engineered VLPs: Self-Packing Gp41-Gag Fused Proteins

Figure 3:
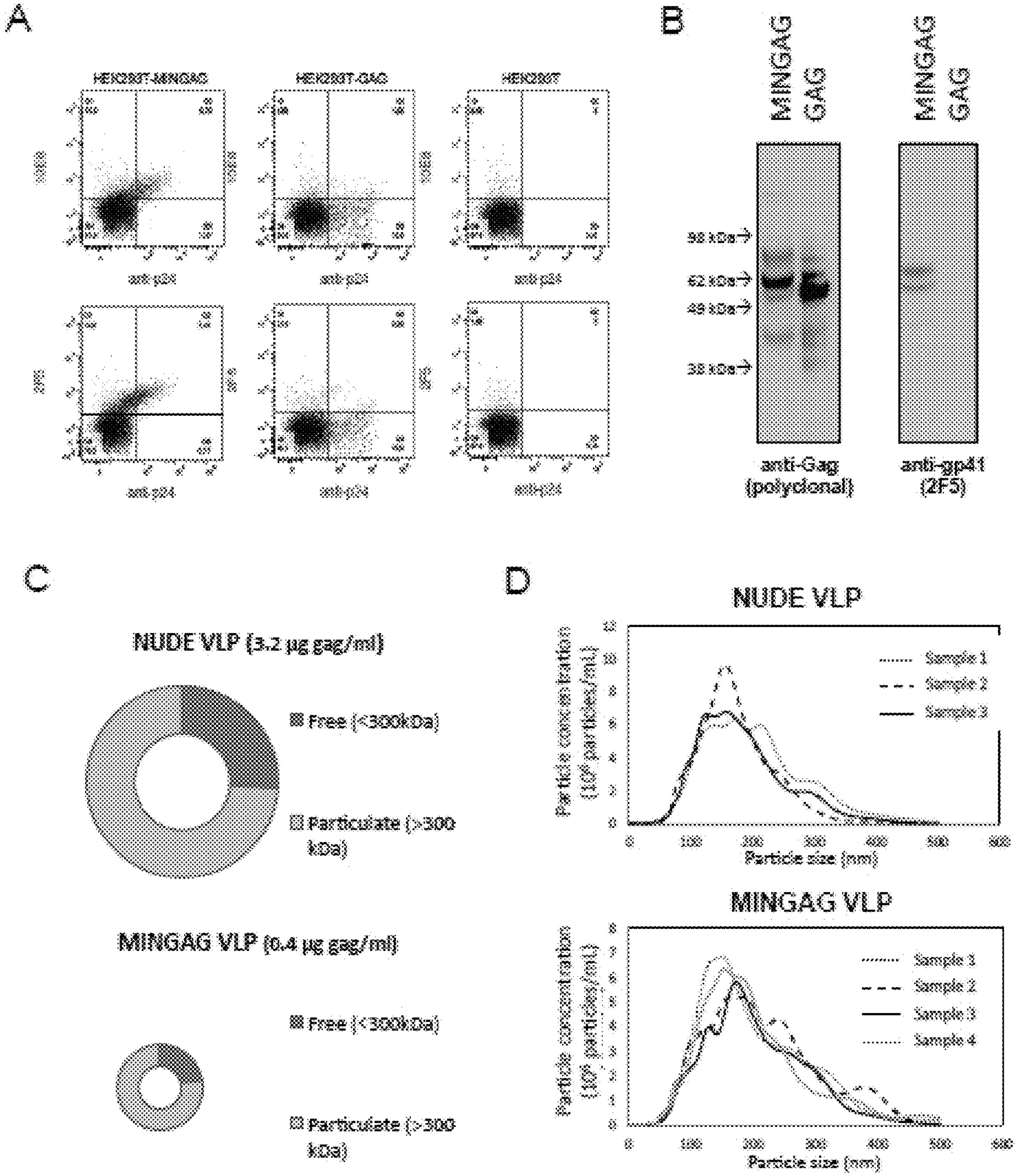
FIG. 3. Characterization of MINGAG VLPs. (A) HEK-293T cells were transfected with the plasmid pcDNA3.1/MINGAG-3.7 coding for the MINGAG fusion protein, the plasmid pcDNA3.1 GAG coding for full-length gag or with an empty pcDNA3.1 plasmid. After 24 hours, cells were cell surface stained with anti-MPER antibodies 2F5 (top) or 10E8 (bottom) and intracellularly stained with the anti-p24 antibody Kc57. Co-expression of both Gag and MPER antigens is clearly observed in both cases. (B) Supernatants from transfected cells were collected and assayed by Western blot with a polyclonal anti-Gag antibody (left) and anti-MPER antibody 2F5 (right). Molecular weight markers are shown for reference. (C) Supernatants were also assayed for total p24 content before and after filtration through a 300 kDa molecular cutoff device. Values represent total p24 content (relative to diameter of the graph) and the fraction of particulate (VLP associated, light grey) and filterable (free, dark grey) material is shown. (D) Supernatants were assayed for particle diameter using Nanosight. Preparations of nude VLPs (top) or MINGAG VLPs (bottom) were assayed in triplicate or quadruplicate, respectively, showing comparable results. Each line corresponds to individual determinations.

Considering the low amounts of MIN protein incorporated in VLP and the low number of Env spikes reported in HIV virions, it was hypothesized that the poor incorporation of MIN protein into the VLPs could be a limiting factor in the above described approach. Then, it was considered whether increasing the density of MPER epitopes on the surface of VLP could enhance its immunogenic potential. See FIG. 2C, Zhu P, et al., Nature 2006, 441:847-885. To test this hypothesis, an expression plasmid (pcDNA3.1/MINGAG-3.7) coding for a fusion protein encompassing the HR2, the MPER and the TM region of gp41 fused to the GAG protein of HIV was constructed. The pcDNA3.1/MINGAG-3.7 plasmid, a control pcDNA3.1GAG and an empty plasmid were transfected in HEK-293T cells and the expression of gp41 and Gag epitopes was analyzed either by flow cytometry or western-blot. FIG. 3A shows the specific cell surface staining using two anti-MPER antibodies (10E8 and 2F5) of Gag+ cells in HEK-293T cultures transfected with the MINGAG construction. MPER cell surface staining is absent in GAG transfected cells, suggesting that the MINGAG protein is properly expressed and reaches the cell surface. Further confirmation of proper expression was achieved in Western Blot analyses of cell lysates showing the expression of a major protein recognized by anti-gag antibodies with an apparent molecular weight of 65 kDa and 57 kDa in MINGAG and Gag transfected cells respectively. The same lysates showed a 65 kDa and a second protein when revealed with the 2F5 antibody. See FIG. 3B.

The release of VLP by transfected cells was assessed by ELISA in cleared supernatant collected 48 hours after transfection. Although VLP production was 8-fold lower for the MINGAG construct than for nude VLPs, both proteins showed similar levels of particulate material, suggesting proper particle generation. See FIG. 3C. Further characterization of particle diameter by Nanosight showed similar mean diameter: 160+/−40 nm for nude VLPs and 170+/−50 nm for MINGAG VLPs (Mean+/−SD of four experiments). See FIG. 3D.

Example 3

Immunogenicity of VLP-Gag and VLP-MinGag in Mice

The immunogenicity of the MINGAG VLPs in C57BL/6 mice was tested. Five animals per group were injected with a 200 μL preparation of nude or MINGAG VLPs with or without aluminum phosphate as adjuvant. Immunogens were prepared maintaining the same Gag antigen concentration between groups, wherein the only difference was the presence or not of the MIN fragment in MINGAG VLPs. Accordingly, all animals were injected with four doses (at 3 weeks interval) of 32 ng of gag antigen.

Figure 4:
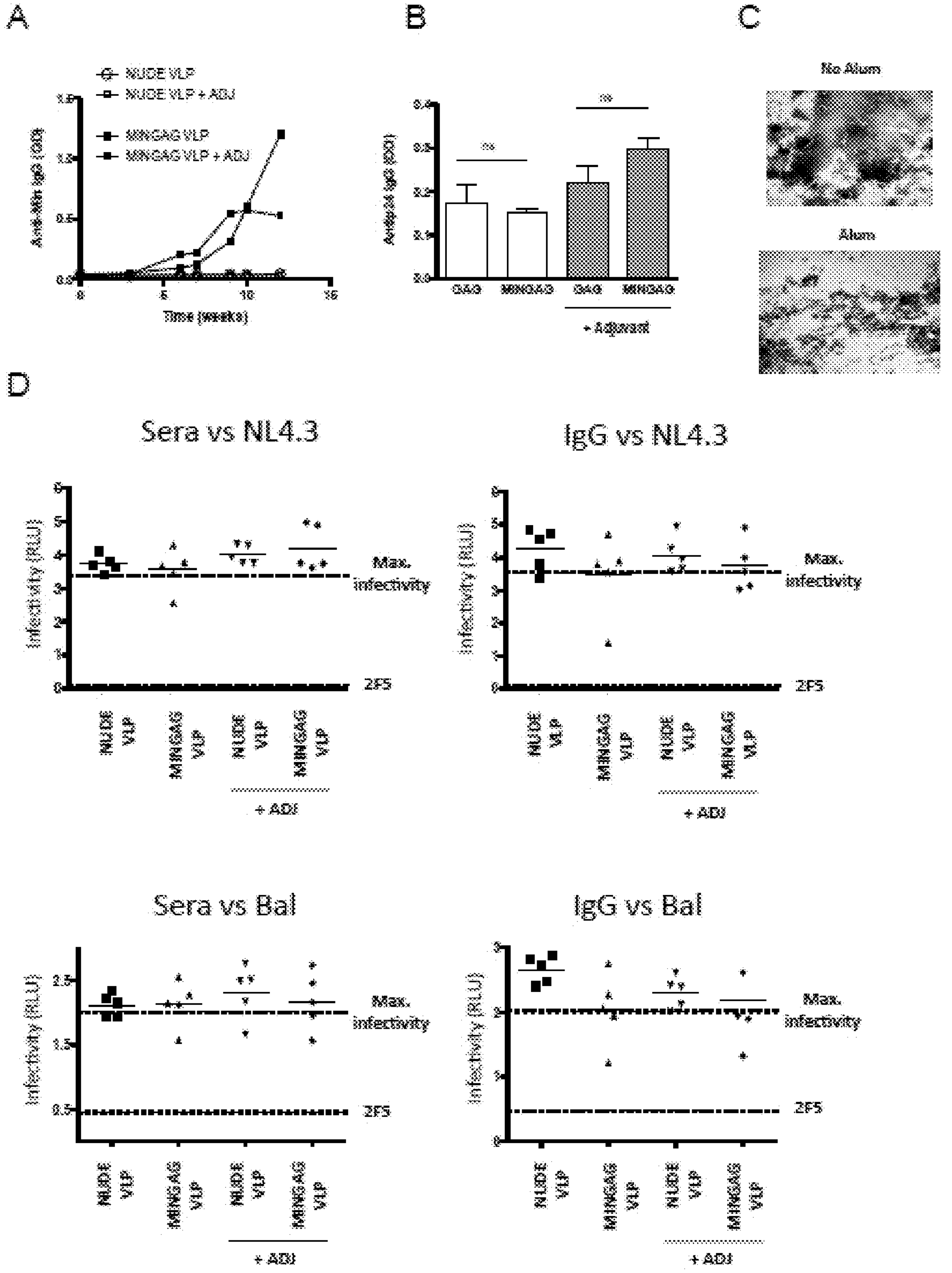
FIG. 4. MINGAG VLP immunogenicity in mice. (A) Time course of anti-MIN IgG in mice immunized with nude VLPs or MINGAG VLPs with or without the adjuvant aluminum phosphate (+ADJ). (B) Magnitude of anti-Gag IgGs after sacrifice in mice immunized with nude VLPs or MINGAG VLPs with or without the adjuvant aluminum phosphate. (C) Electron microscopy analysis of untreated (top) and aluminum phosphate treated (bottom) VLP used for immunization. (D) Neutralizing activity of sera (1/100 dilution) and purified IgG (100 μg/mL) from sacrificed animals was assayed in TZM-b1 cells against the indicated viruses. NL43 and BaL infectivity in the presence of individual animal sera or IgGs is shown.

The time course of anti-gp41 IgG responses (measured using the MIN antigen) showed high and specific immunogenicity in both MINGAG immunized groups, with a faster elicitation in adjuvanted animals but higher final levels in animals immunized only with VLP. See FIG. 4A. Conversely, anti p24-Gag IgGs that were similar in animals immunized with nude or MINGAG-VLPs and were higher in both groups of adjuvanted animals. See FIG. 4B. Whether the enhancing effect of adjuvant on anti-Gag responses and the inhibitory effect on anti-gp41 responses could be due to undesired effects on VLP structure was tested. Electron microscopy analysis showed that aluminum phosphate treated VLPs loss native structure suggesting that release of GAG content could explain these results. See FIG. 4C.

These results indicate that the preparation of MINGAG VLPs is immunogenic, as some of the animals immunized with this preparation could mount a strong IgG response. However, no significant neutralizing activity was observed in both sera and purified IgG obtained from control or immunized animals against two laboratory adapted viruses (i.e. NL43 and BaL). See FIG. 4D.

Figure 5:
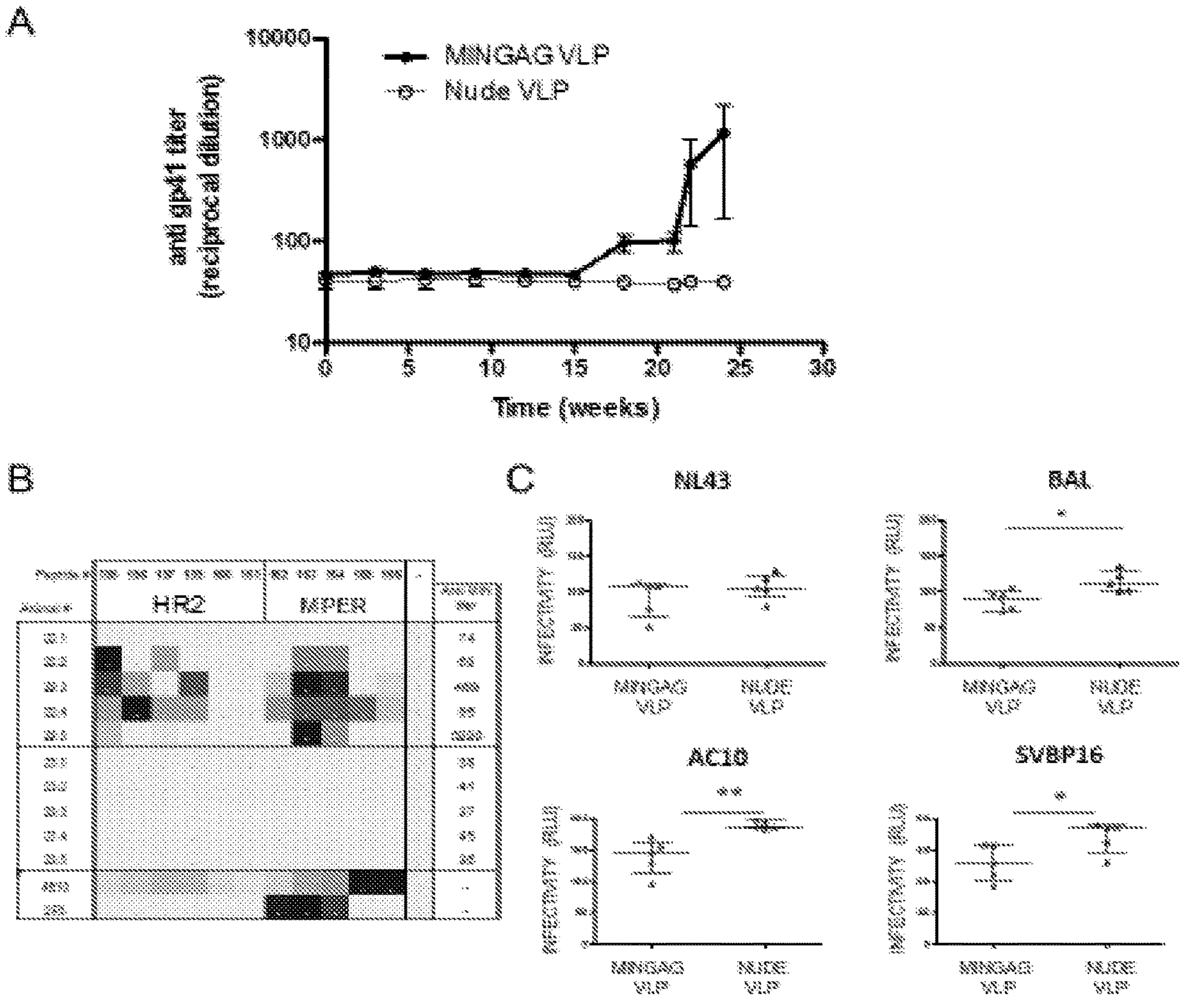
FIG. 5. Peptide/VLP immunization in mice. (A) Time course of anti-MIN IgGs in mice immunized with four doses of KLH-MPER and four doses of MINGAG VLPs or with control KLH and NUDE VLPs. (B) Mapping of anti-MIN IgG responses in immunized mice. Data show reactivity of serum obtained from individual animals against a set of 15mers overlapping peptides that cover the HR2 and MPER sequences of gp41 as described in methods. (C) Neutralizing activity of sera from sacrificed animals (1/100 dilution) was assayed in TZM-b1 cells against the indicated viruses. Viral infectivity in the presence of individual animal sera is shown. Asterisks denote statistical significance.

To increase the response to the MPER of our MINGAG protein, a second immunization procedure was designed in which animals were immunized with MPER peptides coupled to KLH (four doses every three weeks) before VLP immunization (as the immunization protocol described above) in the absence of adjuvant. Again, all animals showed similar anti-Gag responses, while only MINGAG immunized animals showed strong anti-gp41 IgG responses. See FIG. 5A. Mapping of anti-gp41 IgG responses showed two main immunogenic areas, one of them covering the HR2 region, and the second one in the MPER sequence overlapping with the 2F5 epitope. See FIG. 5B. Consistently, a low but significant neutralizing activity was observed in sera from MINGAG VLP immunized animals compared to control mice. See FIG. 5C. Neutralization was observed against the BaL, AC10 and SVBP16 isolates of HIV (all subtype B) and was specifically elicited by immunization since it was retained in the IgG fraction of sera and was absent in preimmune sera.

Example 4

Immunogenicity of VLP-Gag and VLP-MinGag in Rabbits

Figure 6:
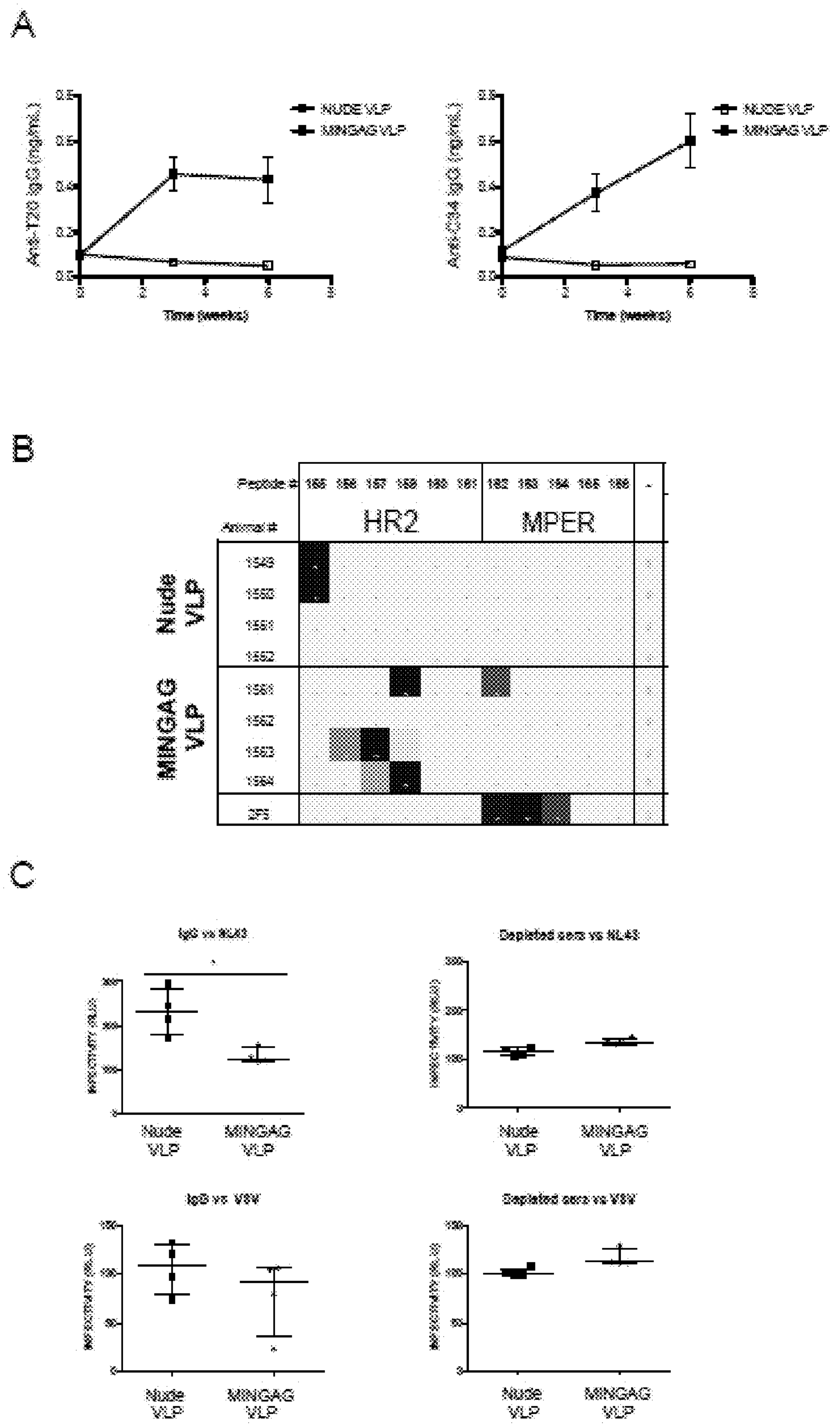
FIG. 6. MINGAG VLP immunization in rabbits. (A) Time course of anti-T-20 and anti-C34 IgGs in rabbits immunized with two doses of nude NUDE VLPs or MINGAG VLPs. (B) Mapping of anti-MIN IgG responses in immunized rabbits. Data show reactivity of serum samples obtained from immunized animals against a set of 15mers overlapping peptides that cover the HR2 and MPER sequences of gp41 as described in methods. (C) Neutralizing activity of purified IgGs (100 μg/mL) and IgG depleted sera from sacrificed animals were assayed in TZM-b1 cells against the indicated viruses. Viral infectivity in the presence of individual animal IgGs is shown. Asterisks denote statistical significance.

A similar approach to Example 3 was used to test the immunogenicity of the MINGAG VLP in rabbits. VLP were injected (two doses of MINGAG VLPs) in the absence of adjuvants and animals were primed with gag and env DNA. All animals generated significant anti-gp41 IgG responses (as measured by the T-20 peptide and the C34 peptides) that mapped to the HR2 and the MPER sequences of the immunogen protein, with some overlap with the 2F5 neutralizing epitope See FIGS. 6A and 6B. Again, a low but significant neutralizing activity was observed in sera from MINGAG VLP immunized animals compared to control rabbits. Neutralization was observed against the NL4-3 isolate, was retained in the IgG fraction, and was specific since no significant activity was detected against VSV pseudotyped viruses. See (FIG. 6C).

Example 5

Codon Optimization Increases VLP Production

Figure 7:
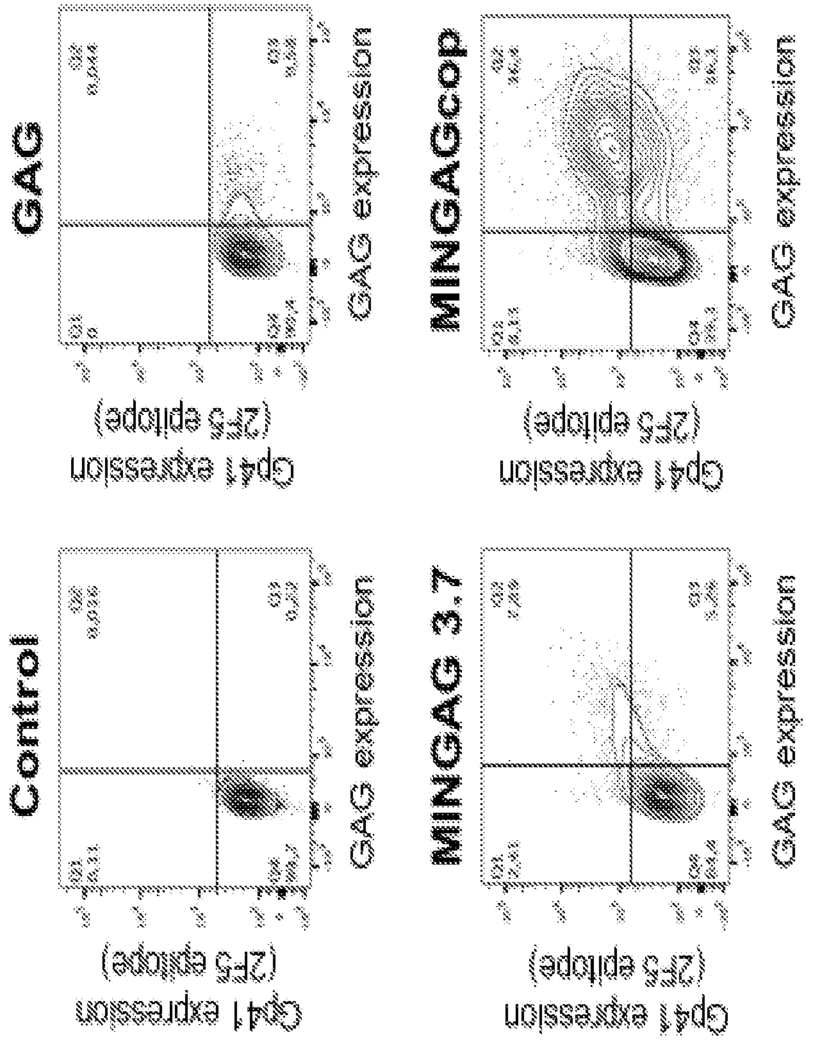
FIG. 7. The effect of codon-optimization on VLP expression. Representative dot plots of HEK-293T cells transfected with an empty plasmid (upper left), a GAG expressing plasmid (wild type, upper right), the MINGAG plasmid 3.7 (non-optimized, lower left) and a codon optimized version of MINGAG (lower right). Cells were stained 24 h after transfection with anti-MPER antibody 2F5 and the anti-GAG antibody Kc57 (intracellular staining). Codon optimization significantly increased both MPER and GAG expression.

A codon optimized (cop) version of the nucleotide sequences coding for the GAG protein and MINGAG fusion protein were cloned in pcDNA3.1 vectors to yield the plasmids pcDNA3.1/GAGcop and pcDNA3.1/MINGAGcop. Transient transfection of HEK-293T cells with original pcDNA3.1/MINGAG-3.7 and the new codon optimized pcDNA3.1/MINGAGcop resulted in a significant higher expression of the codon optimized version. See FIG. 7. The level of expression of both GAG and MPER was 5 to 10 times higher in the codon-optimized version.

Example 6

DNA Sequences Coding for MINGAGcop are Immunogenic in Mice

The higher expression of codon optimized MINGAGcop fusion proteins led to exploring the immunogenicity of naked DNA in murine models. pVax' expression vectors (Thermo Fisher Scientific, Waltham, Mass., USA) coding for MINGAG fusion protein, GAG protein and an empty pVax vector were constructed, purified using EndoFree Plasmid Giga Kit (Qiagen NV, Venlo, NL) and injected to C57BL/6 mice. Five animals per group were injected with a 100 μg of each plasmid, four times at 3-weeks intervals.

Figure 8:
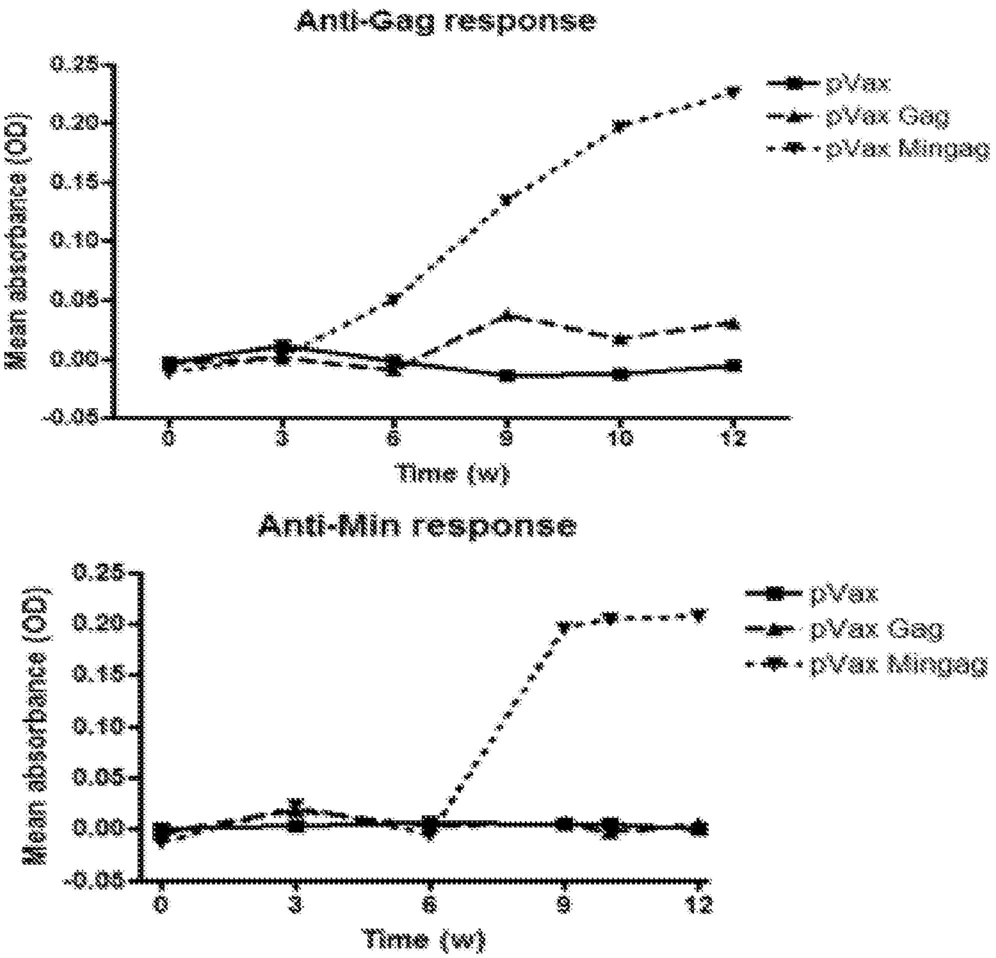
FIG. 8. Immunization of mice with DNA coding for self-packing VLP induces anti-Gag and anti-gp41 humoral responses. Time course of anti-GAG (upper panel) and anti-MIN (lower panel) IgG responses in mice immunized with four doses of naked DNA (using empty, GAG coding and MINGAG coding pVAX1 vectors.

The time course of anti-gp41 IgG responses (measured using the MIN antigen) showed specific immunogenicity exclusively in the pVaxMINGAGcop immunized group. See FIG. 8. Conversely, anti-p24-Gag IgGs were detected in animals immunized with pVAXGAGcop and pVaxMINGAGcop. See FIG. 8. Altogether, these data indicate that DNA vaccination induces GAG and MINGAG expression in vivo capable of eliciting a humoral response.

Example 7

Linker Sequences are Relevant for Antigenicity

Figure 9A:
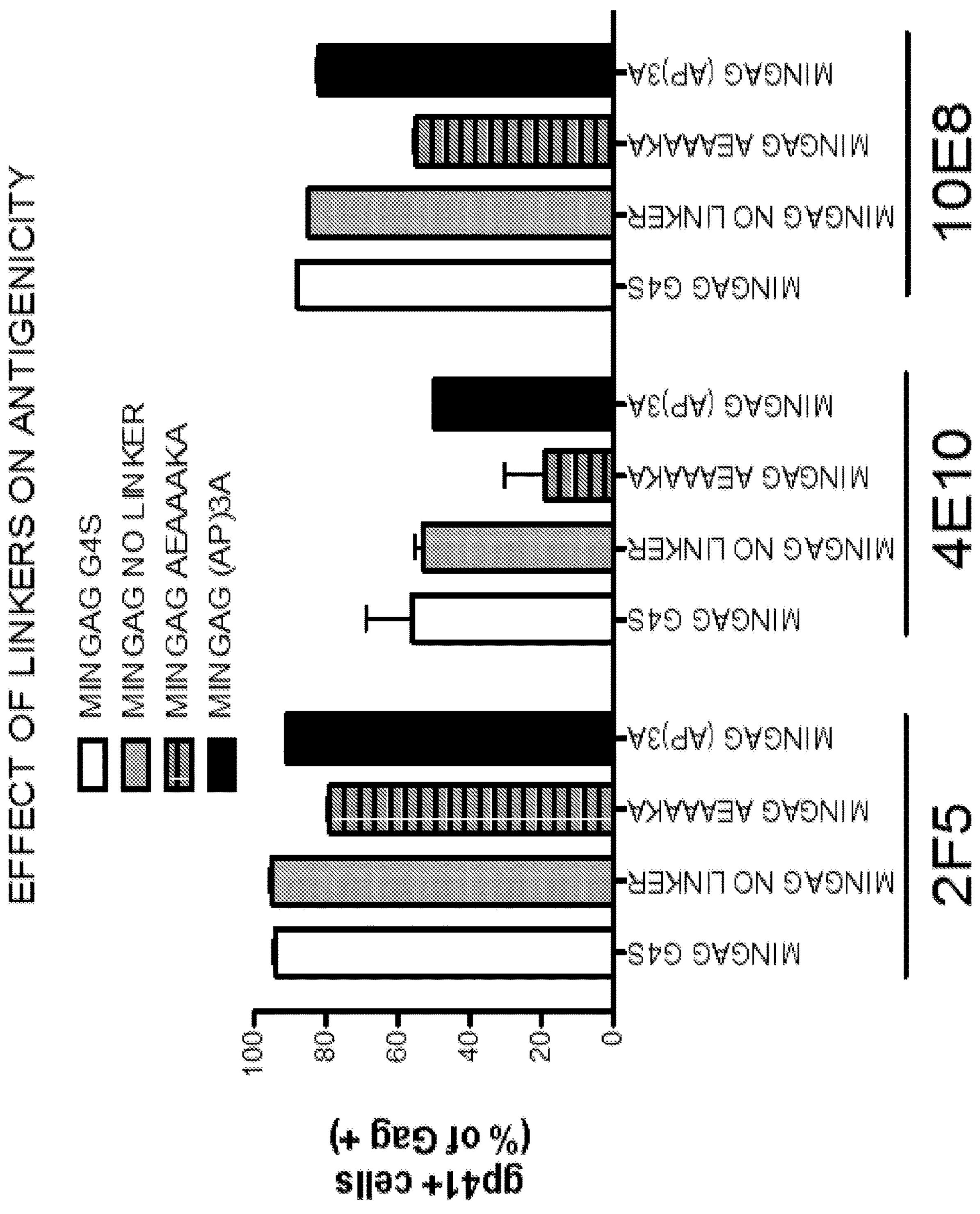
FIG. 9. The effect of different linkers placed between MIN and GAG on VLP antigenicity and production. MINGAG fusion proteins with a G4S, with no linker or with AEAAAKA or APAPAPA linkers were expressed in HEK-293T cells. (A) 48 h after transfection cells were stained with the indicated anti-MPER antibodies (2F5, 10E8 and 4E10) and with the anti-GAG antibody Kc57. The percentage of MPER+ cells among the GAG+ events is shown as a measure of epitope exposure. (B) The production of VLP was measured by ELISA in supernatants of transfected cells and normalized to the MINGAG G4S construct.
Figure 9B:
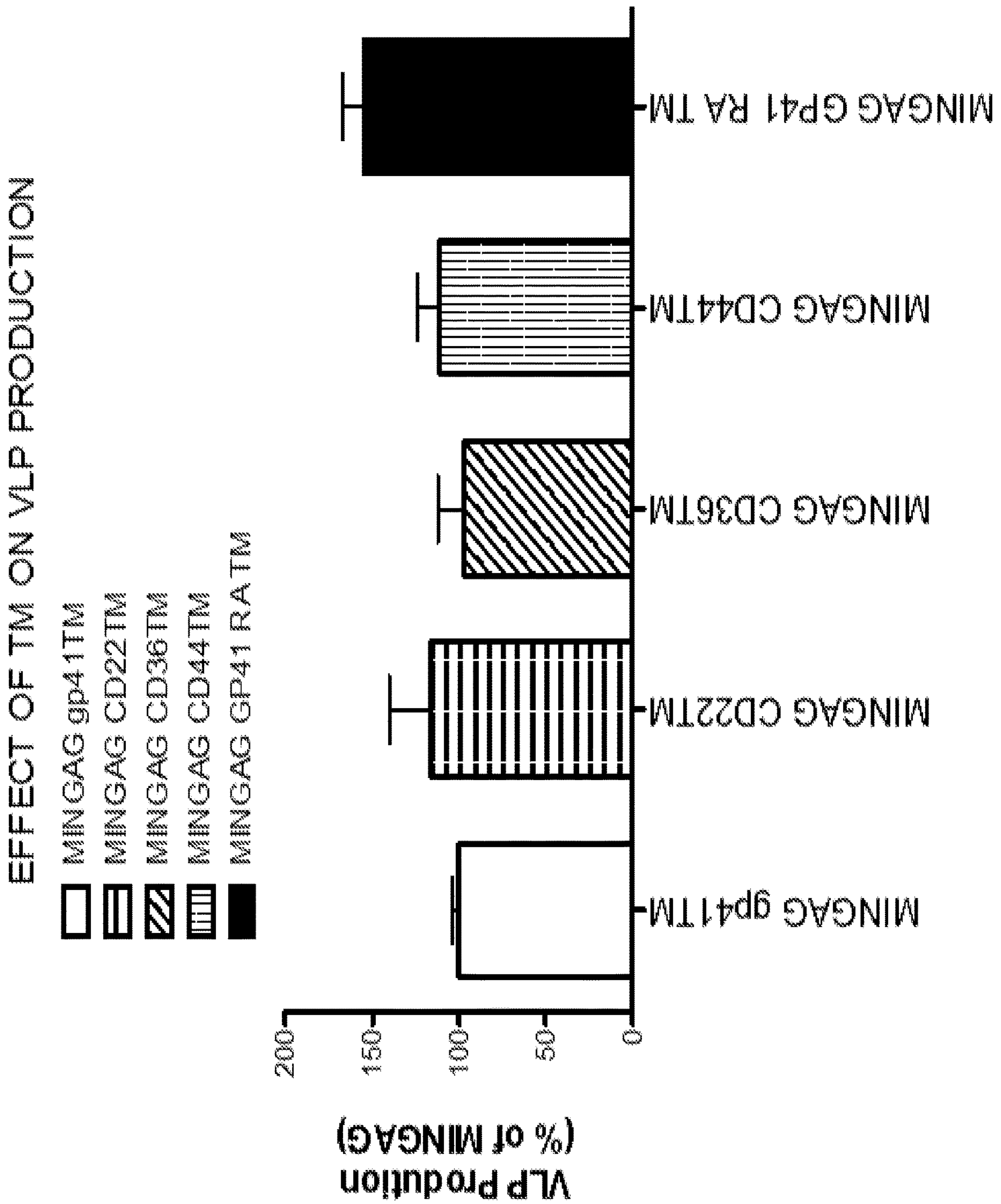

The general structure of fusion proteins according to the invention includes a small linker region between the TM and the GAG sequences. Whether changes in this small linker sequence affect the expression and production of VLPs was evaluated. For addressing this issue, different versions of the codon optimized pcDNA3.1/MINGAGcop were generated containing a GGGS (SEQ ID: 23), no linker, an alanine/glutamic acid and lysine linker (SEQ ID NO: 26) or an alanine/proline linker (SEQ ID NO: 27) sequences. See FIG. 9. The results show that the surface expression of three different epitopes of gp41 (defined by the antibodies 2F5, 4E10 and 10E8) was affected significantly by the linker sequence. See FIG. 9A. The linker GGGS (G3S) exhibited the highest level of expression of 4E10 and 10E8 antigenic sites. Interestingly, no significant effects on the level of VLP production (as measured by the content of GAG in culture supernatants) were noticed. See FIG. 9B.

Example 8

TM Sequences are Relevant for Antigenicity and Production

Similarly, the effect of the TM sequence was analyzed, by replacing the TM region of HIV by:

(a) the TM region of the human CD22 molecule (SEQ ID NO: 17), (b) the TM region of the human CD36 molecule (SEQ ID NO: 18), (c) the TM region of the human CD44 molecule (SEQ ID NO: 19) or (d) the R696A mutant of HIV-1 Env (SEQ ID NO: 30).

The expression of epitopes 2F5, 4E10 and 10E8 as well as the production of VLP was assessed.

Figure 10A:
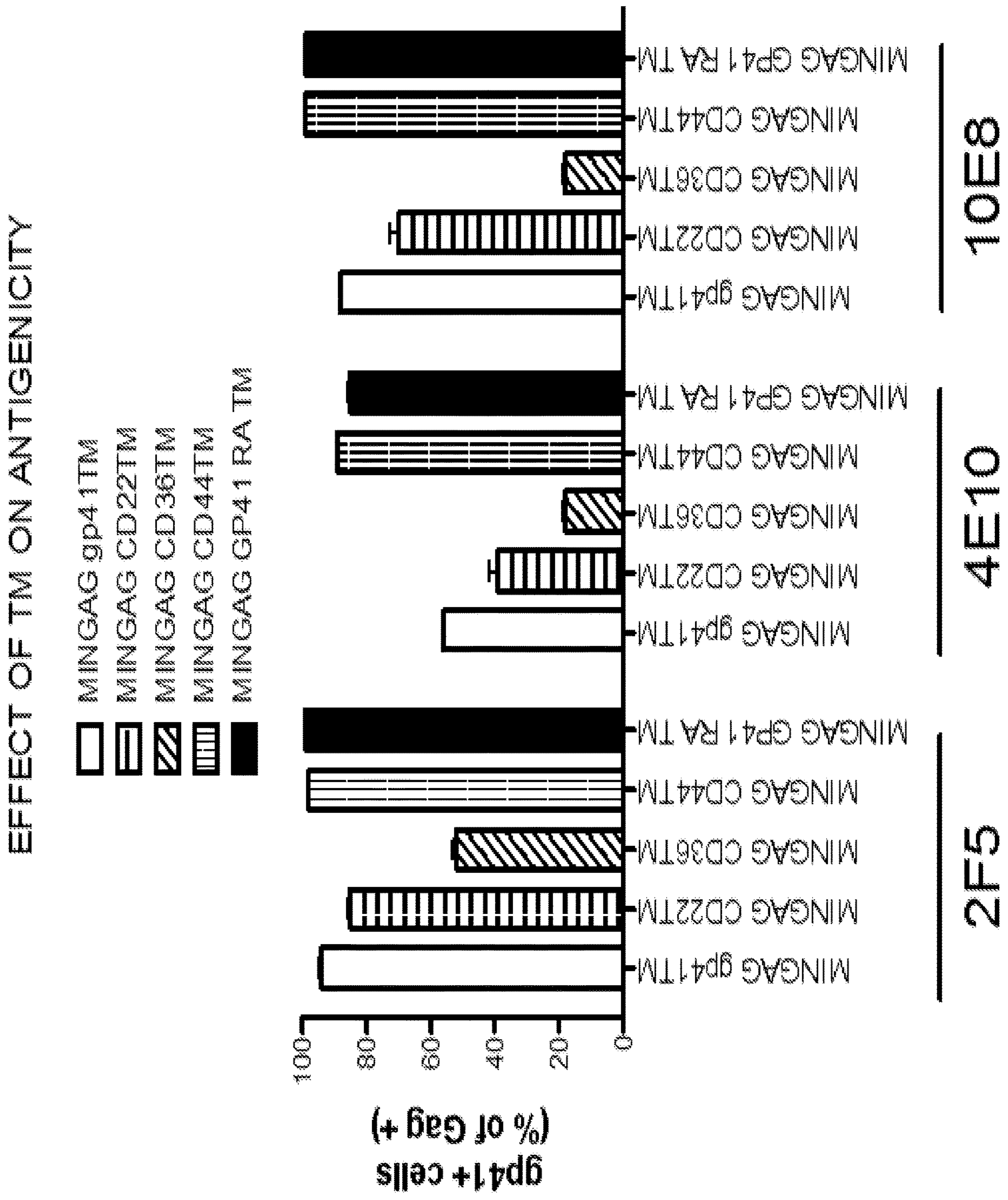
FIG. 10. The effect of different TM sequences placed between the extracellular gp41 sequences and GAG on VLP antigenicity and production. MINGAG fusion proteins with the wild type gp41 TM, the human CD22 TM, the human CD36 TM, the human CD44 TM or the R696A mutated gp41 TM were expressed in HEK-293T cells. (A) 48 h after transfection cells were stained with the indicated anti-MPER antibodies (2F5, 10E8 and 4E10) and with the anti-GAG antibody Kc57. The percentage of MPER+ cells among the GAG+ events is shown as a measure of epitope exposure. (B) The production of VLPs was measured by ELISA in supernatants of transfected cells and normalized to the MINGAG (wild type TM) construct.

The different TM sequences strongly affected the exposure of relevant MPER epitopes. Compared to the wild type gp41 TM, the CD22 and CD36 sequences notably decreased the expression of antigenic sites (mainly the 4E10 and 10E8 epitopes), while both the CD44 TM and the mutated gp41 TM sequences greatly enhanced epitope exposure. This effect was specially observed for the 4E10 antigenic site, indicating that the latter constructs offer a better and more balanced exposure of the MPER than the wild type MIN-GAGcop construct. See FIG. 10A.

Figure 10B:
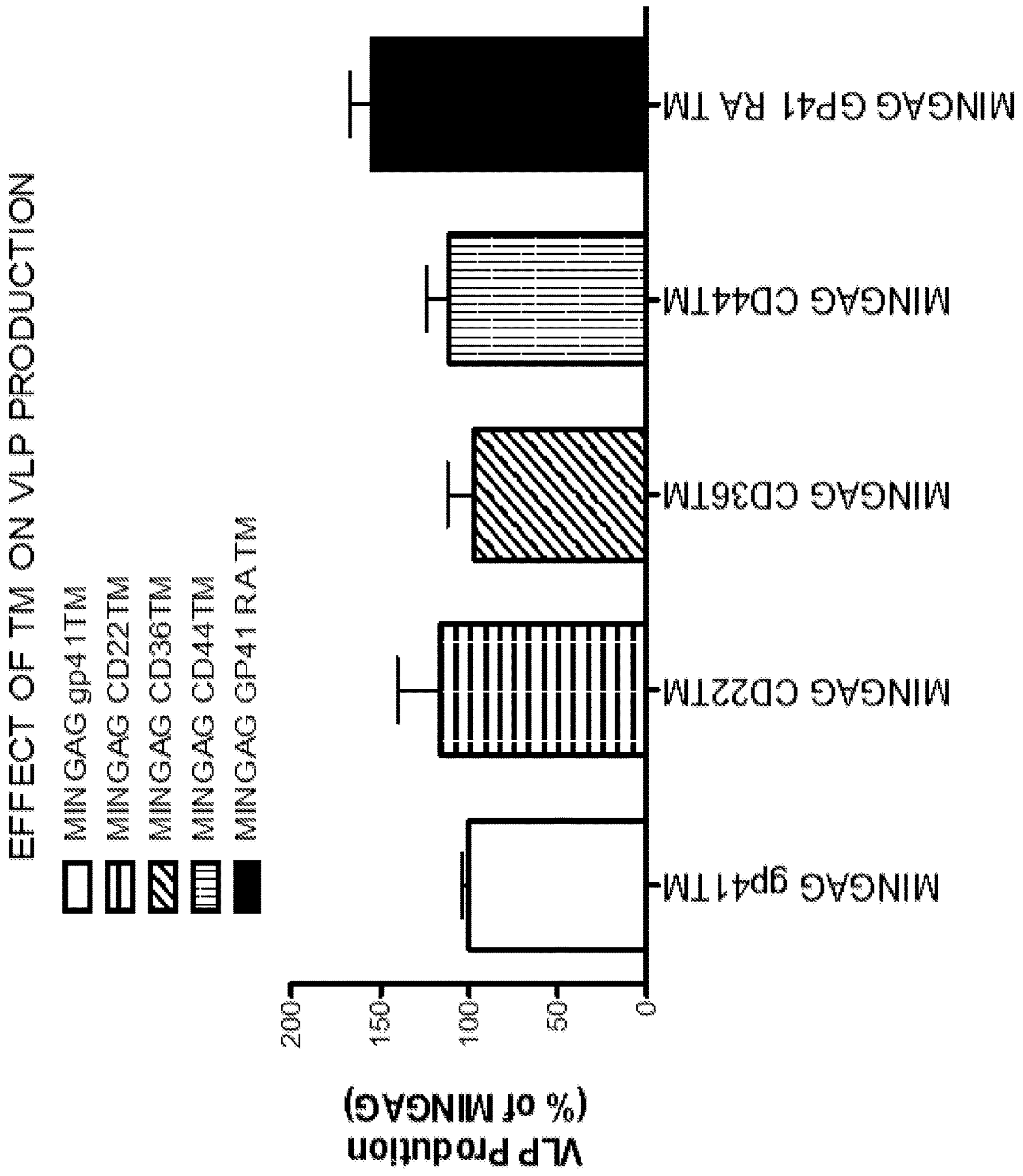

Furthermore, when the production of VLP was assessed and compared to the wild type MINGAGcop construct, the CD22, CD36 and CD44 constructs had no effect on VLP recovery, while a significant higher yield was observed for the mutated gp41 TM sequence, whose production was 1.5-fold higher than the production observed for the MIN-GAGcop reference. See FIG. 10B.

Example 9

Figure 11A:
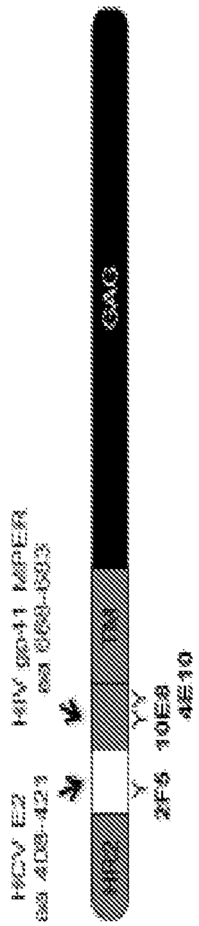
FIG. 11. Expression of short epitopes engrafted on the surface of VLPs. MINGAG fusion protein in which the 2F5 epitope has been replaced by a HCV neutralizing epitope was expressed in HEK-293T cells. (A) Scheme of the fusion protein. (B) 48 h after transfection cells were stained with the indicated anti-MPER antibodies (2F5, 10E8 and 4E10) or the anti-HCV antibody AP33 in combination with the anti-GAG antibody Kc57. Flow cytometry dot plots are shown. (C) The production of VLPs was measured by ELISA in supernatants of transfected cells and normalized to the MINGAG construct.
Figure 11C:
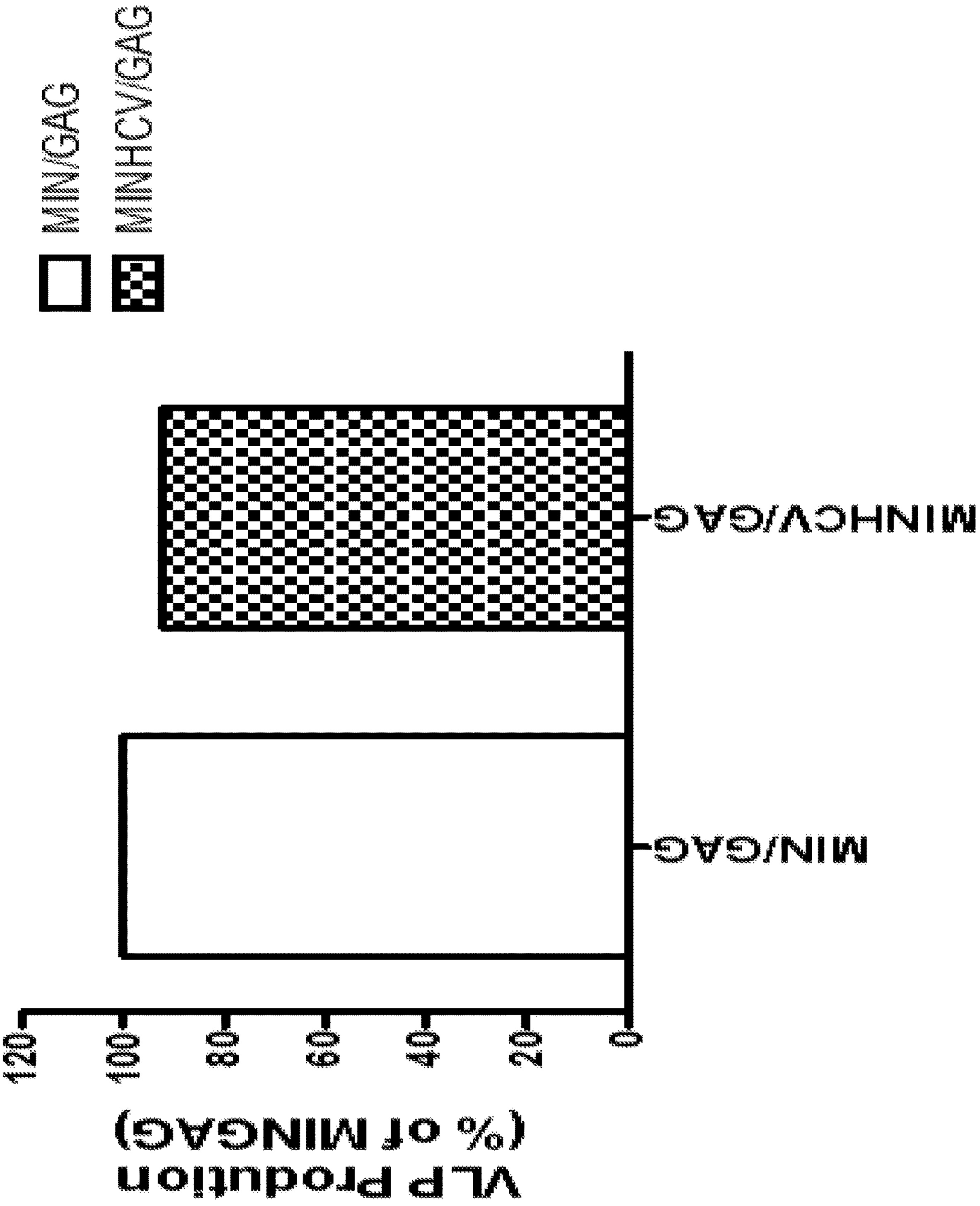

Self-Packing GAG Based VLPs can be Engrafted with Heterologous Small Epitopes To demonstrate the ability of MIN/GAG fusion proteins to expose different epitopes, a neutralizing epitope of the HCV E2 protein was engrafted into the extracellular moiety of MIN. The 2F5 epitope of MIN/GAGcop (aa 655-667 of gp41) was replaced by the peptide KQNIQLINTNGSWH corresponding to aa 408-421 of HCV E2 sequence to generate a MINHCVGAG chimeric protein (SEQ ID NO: 32). The nucleotide sequence (SEQ ID NO: 31) was cloned into pcDNA3.1 vector and expressed in HEK-293T cells. FIG. 11A shows GAG and HCV co-expression in transfected cells, demonstrating epitope exposure. Furthermore, the gp41 2F5 epitope was absent while the 4E10 and 10E8 epitopes (corresponding to the C-term moiety of MPER) were properly exposed. Therefore, MINGAG-based VLPs can be used to expose small epitopes with high density on their surface. Engraftment of the HCV epitope on MIN-GAGcop VLPs did not alter the recovery of VLPs on the supernatant of transfected cells. See FIG. 11B.

Example 10

Versatility of Self-Packing GAG Based VLPs: Accommodation of Different Signal Peptides, Large Antigens and TM Sequences The capacity of the external immunogenic moiety of the GAG based fusion protein for accommodating antigens different from HIV was demonstrated. Several antigens relating to widely different pathologies were selected:

(i) The HCV external protein was selected as an example of viral (non-HIV) infection. A mosaic protein containing several fragments of the HCV E2 sequences, including the membrane proximal heptad repeat sequence and a mutated HCV E2 TM region, was constructed and fused to HIV-1 GAG to generate a sequence optimized HCVE2/GAGcop fusion protein (SEQ ID NO: 34).

(ii) The outer surface protein A (OspA, uniprot POCL66) of the bacteria *Borrelia burgdorferi* (strain ATCC 35210/B31/CIP 102532/DSM 4680), the etiologic agent of Lyme disease. The ospA signal peptide sequence (residues 1-16) was replaced by the human T-cell immunoglobulin mucin receptor TIM-3 (Uniprot Q8TDQ0) signal peptide and fused to the ospA aa 17-273, this construct was placed prior to the CD44 TM to generate a sequence optimized ospA/GAGcop fusion protein (SEQ ID NO: 36)

(iii) The human T-cell immunoglobulin mucin receptor TIM-3 protein (Uniprot Q8TDQ0). TIM-3 is a member of the family of checkpoint immune regulators and is involved in the T cell response to pathogens and tumors. The extracellular and TM regions of the human TIM_3 sequences were placed prior to the GAG sequence to generate a sequence optimized TIM-3/GAGcop fusion protein (SEQ ID NO: 38)

Figure 12A:
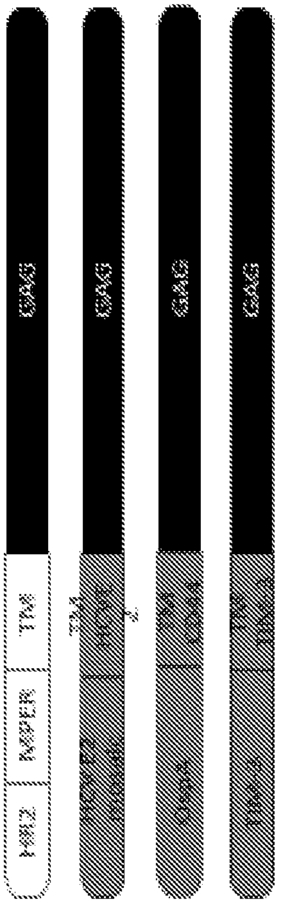
FIG. 12. Expression of large antigens on the surface of VLPs. MINGAG fusion protein in which the extracellular gp41 sequences have been replaced by different antigens were expressed in HEK-293T cells. (A) Scheme of the fusion proteins. (B) 48 h after transfection cells were stained with the indicated antibodies in combination with the anti-GAG antibody Kc57. Flow cytometry dot plots are shown. (C) The production of VLPs was measured by ELISA in supernatants of transfected cells and normalized to the MINGAG construct.
Figure 12C:
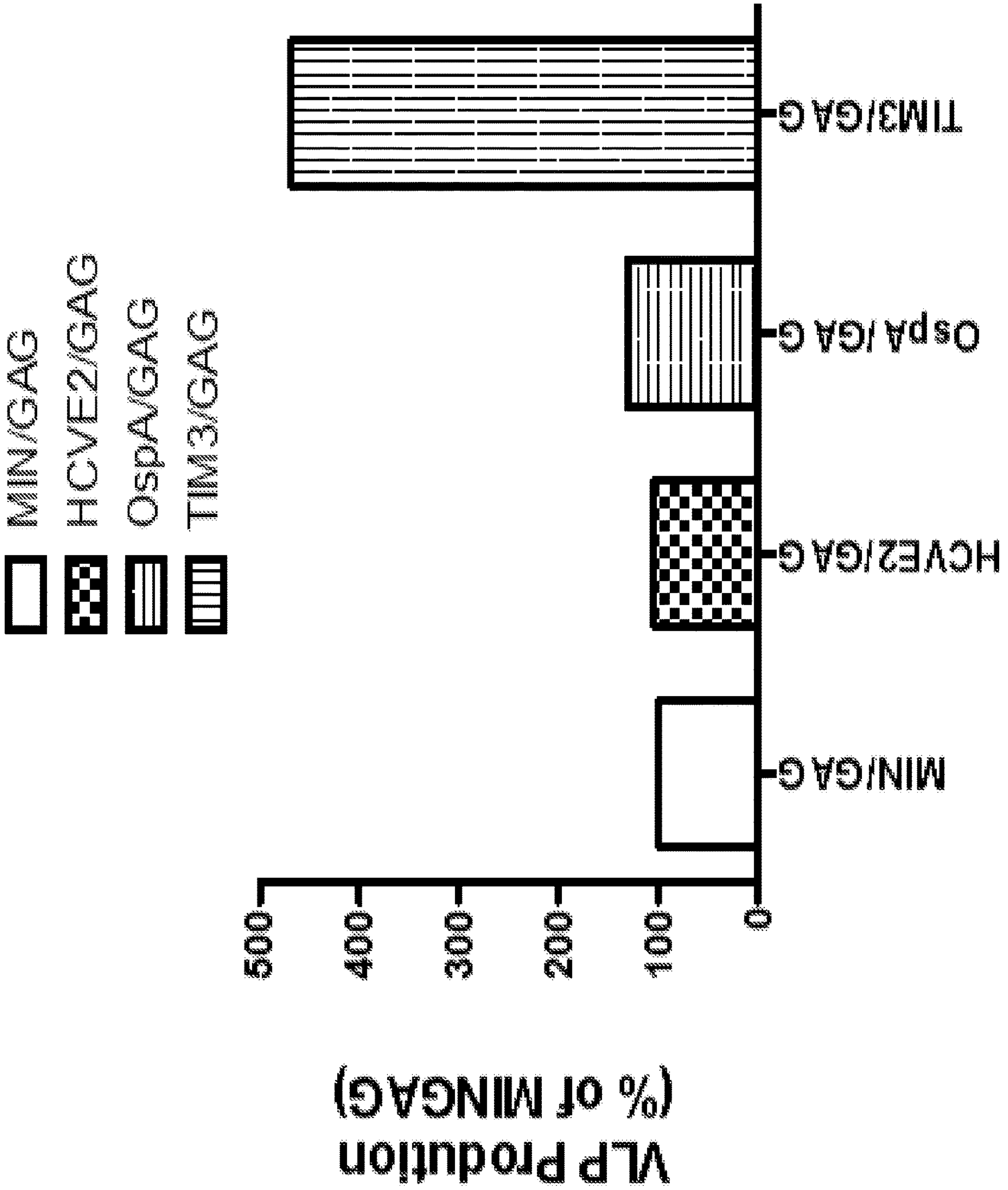

A diagram of these constructs is shown in FIG. 12A. All three constructs were cloned into pcDNA3.1 vectors and transfected in HEK-293T cells. Intracellular GAG and cell surface expressed immunogenic sequences were analyzed by flow cytometry. FIG. 12B shows that the expression of all selected antigens was comparable to the one observed for the original MINGAGcop construct. FIG. 12C shows that the production of all VLPs bearing different antigens is similar or higher to the production of MINGAGcop VLPs.

SEQUENCE LISTING

```
<160> NUMBER OF SEQ ID NOS: 39

<210> SEQ ID NO 1
<211> LENGTH: 500
<212> TYPE: PRT
<213> ORGANISM: Human immunodeficiency virus
<220> FEATURE:
<221> NAME/KEY: PEPTIDE
<222> LOCATION: (1)..(500)
<223> OTHER INFORMATION: SEQ ID NO:1 HIV gag polypeptide sequence
      (isolate HXB2) (aa)

<400> SEQUENCE: 1

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30
```

-continued

```
His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
```

```
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500


<210> SEQ ID NO 2
<211> LENGTH: 499
<212> TYPE: PRT
<213> ORGANISM: Human immunodeficiency virus
<220> FEATURE:
<221> NAME/KEY: PEPTIDE
<222> LOCATION: (1)..(499)
<223> OTHER INFORMATION: SEQ ID NO: 2 HIV gag polypeptide lacking the
      myristoylation sequence (aa)

<400> SEQUENCE: 2

Gly Ala Arg Ala Ser Val Leu Ser Gly Gly Glu Leu Asp Arg Trp Gly
1               5                   10                  15

Lys Ile Arg Leu Arg Pro Gly Gly Lys Lys Lys Tyr Lys Leu Lys His
            20                  25                  30

Ile Val Trp Ala Ser Arg Glu Leu Glu Arg Phe Ala Val Asn Pro Gly
        35                  40                  45

Leu Leu Glu Thr Ser Glu Gly Cys Arg Gln Ile Leu Gly Gln Leu Gln
    50                  55                  60

Pro Ser Leu Gln Thr Gly Ser Glu Glu Leu Arg Ser Leu Tyr Asn Thr
65                  70                  75                  80

Val Ala Thr Leu Tyr Cys Val His Gln Arg Ile Glu Ile Lys Asp Thr
                85                  90                  95

Lys Glu Ala Leu Asp Lys Ile Glu Glu Glu Gln Asn Lys Ser Lys Lys
            100                 105                 110

Lys Ala Gln Gln Ala Ala Ala Asp Thr Gly His Ser Asn Gln Val Ser
        115                 120                 125

Gln Asn Tyr Pro Ile Val Gln Asn Ile Gln Gly Gln Met Val His Gln
    130                 135                 140

Ala Ile Ser Pro Arg Thr Leu Asn Ala Trp Val Lys Val Val Glu Glu
145                 150                 155                 160

Lys Ala Phe Ser Pro Glu Val Ile Pro Met Phe Ser Ala Leu Ser Glu
                165                 170                 175

Gly Ala Thr Pro Gln Asp Leu Asn Thr Met Leu Asn Thr Val Gly Gly
            180                 185                 190

His Gln Ala Ala Met Gln Met Leu Lys Glu Thr Ile Asn Glu Glu Ala
        195                 200                 205

Ala Glu Trp Asp Arg Val His Pro Val His Ala Gly Pro Ile Ala Pro
    210                 215                 220

Gly Gln Met Arg Glu Pro Arg Gly Ser Asp Ile Ala Gly Thr Thr Ser
225                 230                 235                 240

Thr Leu Gln Glu Gln Ile Gly Trp Met Thr Asn Asn Pro Pro Ile Pro
                245                 250                 255

Val Gly Glu Ile Tyr Lys Arg Trp Ile Ile Leu Gly Leu Asn Lys Ile
            260                 265                 270

Val Arg Met Tyr Ser Pro Thr Ser Ile Leu Asp Ile Arg Gln Gly Pro
        275                 280                 285

Lys Glu Pro Phe Arg Asp Tyr Val Asp Arg Phe Tyr Lys Thr Leu Arg
```

-continued

```
    290                 295                 300

Ala Glu Gln Ala Ser Gln Glu Val Lys Asn Trp Met Thr Glu Thr Leu
305                 310                 315                 320

Leu Val Gln Asn Ala Asn Pro Asp Cys Lys Thr Ile Leu Lys Ala Leu
                325                 330                 335

Gly Pro Ala Ala Thr Leu Glu Glu Met Met Thr Ala Cys Gln Gly Val
            340                 345                 350

Gly Gly Pro Gly His Lys Ala Arg Val Leu Ala Glu Ala Met Ser Gln
        355                 360                 365

Val Thr Asn Ser Ala Thr Ile Met Met Gln Arg Gly Asn Phe Arg Asn
    370                 375                 380

Gln Arg Lys Ile Val Lys Cys Phe Asn Cys Gly Lys Glu Gly His Thr
385                 390                 395                 400

Ala Arg Asn Cys Arg Ala Pro Arg Lys Lys Gly Cys Trp Lys Cys Gly
                405                 410                 415

Lys Glu Gly His Gln Met Lys Asp Cys Thr Glu Arg Gln Ala Asn Phe
            420                 425                 430

Leu Gly Lys Ile Trp Pro Ser Tyr Lys Gly Arg Pro Gly Asn Phe Leu
        435                 440                 445

Gln Ser Arg Pro Glu Pro Thr Ala Pro Pro Glu Glu Ser Phe Arg Ser
    450                 455                 460

Gly Val Glu Thr Thr Thr Pro Pro Gln Lys Gln Glu Pro Ile Asp Lys
465                 470                 475                 480

Glu Leu Tyr Pro Leu Thr Ser Leu Arg Ser Leu Phe Gly Asn Asp Pro
                485                 490                 495

Ser Ser Gln


<210> SEQ ID NO 3
<211> LENGTH: 1497
<212> TYPE: DNA
<213> ORGANISM: Human immunodeficiency virus
<220> FEATURE:
<221> NAME/KEY: gene
<222> LOCATION: (1)..(1497)
<223> OTHER INFORMATION: SEQ ID NO: 3 HIV Gag coding for gag polypeptide
      lacking the myristoylation sequence (nt)

<400> SEQUENCE: 3

ggtgcgagag cgtcagtatt aagcggggga gaattagatc gatggggaaa aattcggtta      60

aggccagggg gaaagaagaa gtacaagcta aagcacatcg tatgggcaag cagggagcta     120

gaacgattcg cagttaatcc tggcctgtta gaaacatcag aaggctgtag acaaatactg     180

ggacagctac aaccatccct tcagacagga tcagaggagc ttcgatcact atacaacaca     240

gtagcaaccc tctattgtgt gcaccagcgg atcgagatca aggacaccaa ggaagcttta     300

gacaagatag aggaagagca aaacaagtcc aagaagaagg cccagcaggc agcagctgac     360

acaggacaca gcaatcaggt cagccaaaat taccctatag tgcagaacat ccaggggcaa     420

atggtacatc aggccatatc acctagaact ttaaatgcat gggtaaaagt agtagaagag     480

aaggctttca gcccagaagt gatacccatg ttttcagcat tatcagaagg agccacccca     540

caggacctga acacgatgtt gaacaccgtg gggggacatc aagcagccat gcaaatgtta     600

aaagagacca tcaatgagga agctgcagaa tgggatagag tgcatccagt gcatgcaggg     660

cctattgcac caggccagat gagagaacca aggggaagtg acatagcagg aactactagt     720

acccttcagg aacaaatagg atggatgaca aataatccac ctatcccagt aggagagatc     780
```

-continued

```
tacaagaggt ggataatcct gggattgaac aagatcgtga ggatgtatag ccctaccagc    840

attctggaca taagacaagg accaaaagaa ccctttagag actatgtaga ccggttctat    900

aaaactctaa gagctgagca agcttcacag gaggtaaaaa attggatgac agaaaccttg    960

ttggtccaaa atgcgaaccc agattgtaag accatcctga aggctctcgg cccagcggct   1020

acactagaag aaatgatgac agcatgtcag ggagtaggag gacccggcca taaggcaaga   1080

gttttggctg aagcaatgag ccaagtaaca aattcagcta ccataatgat gcagagaggc   1140

aattttagga accaaagaaa gattgttaag tgtttcaatt gtggcaaaga agggcacaca   1200

gccagaaatt gcagggcccc taggaaaaag ggctgttgga aatgtggaaa ggaaggacac   1260

caaatgaaag attgtactga gagacaggct aattttttag ggaagatctg gccttcctac   1320

aagggaaggc cagggaattt tcttcagagc agaccagagc caacagcccc accagaagag   1380

agcttcaggt ctggggtaga gacaacaact ccccctcaga agcaggagcc gatagacaag   1440

gaactgtatc ctttaacttc cctcagatca ctctttggca acgacccctc gtcacaa      1497


<210> SEQ ID NO 4
<211> LENGTH: 263
<212> TYPE: DNA
<213> ORGANISM: Human immunodeficiency virus
<220> FEATURE:
<221> NAME/KEY: gene
<222> LOCATION: (1)..(263)
<223> OTHER INFORMATION: SEQ ID NO: 4 Min protein gp41 variant (HR2+
      MPER+TM) (nt)

<400> SEQUENCE: 4

atgatttgga ataacatgac ctggatggag tgggacagag aaattaacaa ttacacaagc     60

ttaatacact ccttaattga agaatcgcaa aaccagcaag aaaagaatga acaagaatta    120

ttggaattag ataaatgggc aagtttgtgg aattggttta acataacaaa ttggctgtgg    180

tacataaaat tattcataat gatagtagga ggcttggtag gtttaagaat agtttttgct    240

gtactttcta tagtgaatag agc                                            263


<210> SEQ ID NO 5
<211> LENGTH: 87
<212> TYPE: PRT
<213> ORGANISM: Human immunodeficiency virus
<220> FEATURE:
<221> NAME/KEY: PEPTIDE
<222> LOCATION: (1)..(87)
<223> OTHER INFORMATION: SEQ ID NO: 5 gp41 variant (aa)

<400> SEQUENCE: 5

Met Ile Trp Asn Asn Met Thr Trp Met Glu Trp Asp Arg Glu Ile Asn
1               5                   10                  15

Asn Tyr Thr Ser Leu Ile His Ser Leu Ile Glu Glu Ser Gln Asn Gln
            20                  25                  30

Gln Glu Lys Asn Glu Gln Glu Leu Leu Glu Leu Asp Lys Trp Ala Ser
        35                  40                  45

Leu Trp Asn Trp Phe Asn Ile Thr Asn Trp Leu Trp Tyr Ile Lys Leu
    50                  55                  60

Phe Ile Met Ile Val Gly Gly Leu Val Gly Leu Arg Ile Val Phe Ala
65                  70                  75                  80

Val Leu Ser Ile Val Asn Arg
                85


<210> SEQ ID NO 6
```

```
<211> LENGTH: 12
<212> TYPE: DNA
<213> ORGANISM: Artificial Sequence
<220> FEATURE:
<221> NAME/KEY: gene
<222> LOCATION: (1)..(12)
<223> OTHER INFORMATION: SEQ ID NO: 6 Glycine linker (nt)

<400> SEQUENCE: 6

ggtggcggtg gc                                                           12


<210> SEQ ID NO 7
<211> LENGTH: 27
<212> TYPE: DNA
<213> ORGANISM: Artificial Sequence
<220> FEATURE:
<221> NAME/KEY: gene
<222> LOCATION: (1)..(27)
<223> OTHER INFORMATION: SEQ ID NO: 7 Partial polylinker derived from
      pcDNA3.1D/V5-His-TOPO (Invitrogen) (nt)

<400> SEQUENCE: 7

aagggtcaag acaattctgc agatatc                                           27


<210> SEQ ID NO 8
<211> LENGTH: 108
<212> TYPE: DNA
<213> ORGANISM: Artificial Sequence
<220> FEATURE:
<221> NAME/KEY: gene
<222> LOCATION: (1)..(108)
<223> OTHER INFORMATION: SEQ ID NO: 8 Vector sequence including
      V5-epitope, 6xHis tag and stop codon (nt)

<400> SEQUENCE: 8

ggcggccgct cgagtctaga gggcccgcgg ttcgaaggta agcctatccc taaccctctc      60

ctcggtctcg attctacgcg taccggtcat catcaccatc accattga                   108


<210> SEQ ID NO 9
<211> LENGTH: 1908
<212> TYPE: DNA
<213> ORGANISM: Artificial Sequence
<220> FEATURE:
<221> NAME/KEY: gene
<222> LOCATION: (1)..(1908)
<223> OTHER INFORMATION: SEQ ID NO: 9 MINGAG3.7 fusion protein (nt)

<400> SEQUENCE: 9

atgatttgga ataacatgac ctggatggag tgggacagag aaattaacaa ttacacaagc      60

ttaatacact ccttaattga agaatcgcaa aaccagcaag aaaagaatga acaagaatta     120

ttggaattag ataaatgggc aagtttgtgg aattggttta acataacaaa ttggctgtgg     180

tacataaaat tattcataat gatagtagga ggcttggtag gtttaagaat agtttttgct     240

gtactttcta tagtgaatag agctggtggc ggtggcaagg gtcaagacaa ttctgcagat     300

atcggtgcga gagcgtcagt attaagcggg ggagaattag atcgatgggg aaaaaattcgg    360

ttaaggccag ggggaaagaa gaagtacaag ctaaagcaca tcgtatgggc aagcagggag     420

ctagaacgat tcgcagttaa tcctggcctg ttagaaacat cagaaggctg tagacaaata     480

ctgggacagc tacaaccatc ccttcagaca ggatcagagg agcttcgatc actatacaac     540

acagtagcaa ccctctattg tgtgcaccag cggatcgaga tcaaggacac caaggaagct     600

ttagacaaga tagaggaaga gcaaaacaag tccaagaaga aggcccagca ggcagcagct     660

gacacaggac acagcaatca ggtcagccaa aattacccta tagtgcagaa catccagggg     720
```

caaatggtac atcaggccat atcacctaga actttaaatg catgggtaaa agtagtagaa 780
gagaaggctt tcagcccaga agtgataccc atgttttcag cattatcaga aggagccacc 840
ccacaggacc tgaacacgat gttgaacacc gtgggggggac atcaagcagc catgcaaatg 900
ttaaaagaga ccatcaatga ggaagctgca gaatgggata gagtgcatcc agtgcatgca 960
gggcctattg caccaggcca gatgagagaa ccaaggggaa gtgacatagc aggaactact 1020
agtacccttc aggaacaaat aggatggatg acaaataatc cacctatccc agtaggagag 1080
atctacaaga ggtggataat cctgggattg aacaagatcg tgaggatgta tagccctacc 1140
agcattctgg acataagaca aggaccaaaa gaacccttta gagactatgt agaccggttc 1200
tataaaactc taagagctga gcaagcttca caggaggtaa aaaattggat gacagaaacc 1260
ttgttggtcc aaaatgcgaa cccagattgt aagaccatcc tgaaggctct cggcccagcg 1320
gctacactag aagaaatgat gacagcatgt cagggagtag gaggacccgg ccataaggca 1380
agagttttgg ctgaagcaat gagccaagta acaaattcag ctaccataat gatgcagaga 1440
ggcaatttta ggaaccaaag aaagattgtt aagtgtttca attgtggcaa agaagggcac 1500
acagccagaa attgcagggc ccctaggaaa aagggctgtt ggaaatgtgg aaaggaagga 1560
caccaaatga aagattgtac tgagagacag gctaattttt tagggaagat ctggccttcc 1620
tacaagggaa ggccagggaa ttttcttcag agcagaccag agccaacagc cccaccagaa 1680
gagagcttca ggtctggggt agagacaaca actccccctc agaagcagga gccgatagac 1740
aaggaactgt atcctttaac ttccctcaga tcactctttg gcaacgaccc ctcgtcacaa 1800
ggcggccgct cgagtctaga gggcccgcgg ttcgaaggta agcctatccc taaccctctc 1860
ctcggtctcg attctacgcg taccggtcat catcaccatc accattga 1908

<210> SEQ ID NO 10
<211> LENGTH: 50
<212> TYPE: DNA
<213> ORGANISM: Artificial Sequence
<220> FEATURE:
<221> NAME/KEY: sig_peptide
<222> LOCATION: (1)..(50)
<223> OTHER INFORMATION: SEQ ID NO: 10 GM-CSF signal peptide (nt)

<400> SEQUENCE: 10
atgtggctgc agtctctgct gctgctgggc accgtggcct gcagcatcag 50

<210> SEQ ID NO 11
<211> LENGTH: 259
<212> TYPE: DNA
<213> ORGANISM: Artificial Sequence
<220> FEATURE:
<221> NAME/KEY: gene
<222> LOCATION: (1)..(259)
<223> OTHER INFORMATION: SEQ ID NO: 11 Codon optimized MIN protein (nt)

<400> SEQUENCE: 11
catctggaac cacaccacct ggatggaatg ggacagagag atcaacaact acaccagcct 60
gatccactcc ctgatcgagg aaagccagaa ccagcaggaa aagaacgaac aggaactgct 120
ggaactggac aagtgggcca gcctgtggaa ctggttcaac atcaccaact ggctgtggta 180
catcaagctg ttcatcatga tcgtgggcgg cctcgtgggc ctgagaatcg tgtttgccgt 240
gctgagcatc gtgaaccgg 259

<210> SEQ ID NO 12

<211> LENGTH: 15
<212> TYPE: DNA
<213> ORGANISM: Artificial Sequence
<220> FEATURE:
<221> NAME/KEY: gene
<222> LOCATION: (1)..(15)
<223> OTHER INFORMATION: SEQ ID NO: 12 GS linker

<400> SEQUENCE: 12
ggaggcggag gatcc 15

<210> SEQ ID NO 13
<211> LENGTH: 1497
<212> TYPE: DNA
<213> ORGANISM: Artificial Sequence
<220> FEATURE:
<221> NAME/KEY: gene
<222> LOCATION: (1)..(1497)
<223> OTHER INFORMATION: SEQ ID NO:13 Codon optimized GAGHXB2 cop (nt)

<400> SEQUENCE: 13
ggcgctagag cttctgtgct gtctgggggc gaactggata gatgggagaa gatccggctg 60
cggcctggcg gcaagaagaa gtacaagctg aagcacatcg tgtgggcctc cagagagctg 120
gaaagattcg ccgtgaaccc cggcctgctg gaaaccagcg agggctgcag acagatcctg 180
ggacagctgc agcccagcct gcagaccgga agcgaggaac tgcggagcct gtacaacacc 240
gtggccacac tgtattgcgt gcaccagcgg atcgagatca aggacaccaa agaggccctg 300
gacaagatcg aggaagaaca gaacaagtct aagaagaagg cccagcaggc tgccgccgat 360
accggccact ctaatcaggt gtcccagaac taccccatcg tgcagaacat ccagggccag 420
atggtgcatc aggccatcag ccccagaacc ctgaacgcct gggtcaaggt ggtggaagag 480
aaggccttta gccccgaagt gatccccatg ttcagcgccc tgtctgaggg cgccacaccc 540
caggacctga acaccatgct gaacacagtg ggcggacacc aggccgccat gcagatgctg 600
aaagagacaa tcaacgaaga ggccgccgag tgggacagag tgcaccctgt gcatgccgga 660
cctatcgccc ctggccagat gagagagccc agaggctctg atatcgccgg caccaccagc 720
accctgcagg aacagatcgg ctggatgacc aacaaccccc ccatccccgt gggcgagatc 780
tacaagcggt ggatcatcct gggcctgaac aagattgtgc ggatgtacag ccccacctcc 840
atcctggaca tccggcaggg ccccaaagag cccttcagag actacgtgga ccggttctac 900
aagaccctga gagccgagca ggccagccag gaagtgaaga attggatgac cgagacactg 960
ctggtgcaga acgccaaccc cgactgcaag accatcctga aggccctggg acctgccgcc 1020
accctggaag agatgatgac agcctgtcag ggcgtgggag gcccaggcca caaagctaga 1080
gtgctggccg aggccatgag ccaagtgacc aactccgcca ccattatgat gcagcggggc 1140
aacttccgga accagcggaa gatcgtgaag tgcttcaact gcggcaaaga gggccacacc 1200
gcccggaatt gcagagcccc cagaaagaaa ggctgctgga agtgtggaaa agaggggcac 1260
cagatgaagg actgcaccga gcggcaggcc aacttcctgg gcaagatctg gcctagctac 1320
aagggcagac ccggcaattt cctgcagagc agacccgagc ctaccgcccc tcccgaggaa 1380
agctttagaa gcggcgtgga aaccaccacc cccccacaga agcaggaacc catcgacaaa 1440
gagctgtacc ccctgaccag cctgagaagc ctgttcggca acgaccccag cagccag 1497

<210> SEQ ID NO 14
<211> LENGTH: 1827
<212> TYPE: DNA
<213> ORGANISM: Artificial Sequence
<220> FEATURE:
<221> NAME/KEY: gene
<222> LOCATION: (1)..(1827)
<223> OTHER INFORMATION: SEQ ID NO: 15 MINGAGHXB2 cop (nt)

<400> SEQUENCE: 14

```
atgtggctgc agtctctgct gctgctgggc accgtggcct gcagcatcag catctggaac     60
cacaccacct ggatggaatg ggacagagag atcaacaact acaccagcct gatccactcc    120
ctgatcgagg aaagccagaa ccagcaggaa aagaacgaac aggaactgct ggaactggac    180
aagtgggcca gcctgtggaa ctggttcaac atcaccaact ggctgtggta catcaagctg    240
ttcatcatga tcgtgggcgg cctcgtgggc ctgagaatcg tgtttgccgt gctgagcatc    300
gtgaaccggg gaggcggagg atccggcgcg cgcgcgagcg tgctgagcgg cggcgaactg    360
gatcgctggg aaaaaattcg cctgcgcccg ggcggcaaaa aaaaatataa actgaaacat    420
attgtgtggg cgagccgcga actggaacgc tttgcggtga acccgggcct gctggaaacc    480
agcgaaggct gccgccagat tctgggccag ctgcagccga gcctgcagac cggcagcgaa    540
gaactgcgca gcctgtataa caccgtggcg accctgtatt gcgtgcatca gcgcattgaa    600
attaaagata ccaaagaagc gctggataaa attgaagaag aacagaacaa aagcaaaaaa    660
aaagcgcagc aggcggcggc ggataccggc catagcaacc aggtgagcca gaactatccg    720
attgtgcaga acattcaggg ccagatggtg catcaggcga ttagcccgcg caccctgaac    780
gcgtgggtga aagtggtgga agaaaaagcg tttagcccgg aagtgattcc gatgtttagc    840
gcgctgagcg aaggcgcgac cccgcaggat ctgaacacca tgctgaacac cgtgggcggc    900
catcaggcgg cgatgcagat gctgaaagaa accattaacg aagaagcggc ggaatgggat    960
cgcgtgcatc cggtgcatgc gggcccgatt gcgccgggcc agatgcgcga accgcgcggc   1020
agcgatattg cgggcaccac cagcaccctg caggaacaga ttggctggat gaccaacaac   1080
ccgccgattc cggtgggcga aatttataaa cgctggatta ttctgggcct gaacaaaatt   1140
gtgcgcatgt atagcccgac cagcattctg gatattcgcc agggcccgaa agaaccgttt   1200
cgcgattatg tggatcgctt ttataaaacc ctgcgcgcgg aacaggcgag ccaggaagtg   1260
aaaaactgga tgaccgaaac cctgctggtg cagaacgcga acccggattg caaaaccatt   1320
ctgaaagcgc tgggcccggc ggcgaccctg gaagaaatga tgaccgcgtg ccagggcgtg   1380
ggcggcccgg gccataaagc gcgcgtgctg gcggaagcga tgagccaggt gaccaacagc   1440
gcgaccatta tgatgcagcg cggcaacttt cgcaaccagc gcaaaattgt gaaatgcttt   1500
aactgcggca aagaaggcca taccgcgcgc aactgccgcg cgccgcgcaa aaaaggctgc   1560
tggaaatgcg gcaaagaagg ccatcagatg aaagattgca ccgaacgcca ggcgaacttt   1620
ctgggcaaaa tttggccgag ctataaaggc cgcccgggca actttctgca gagccgcccg   1680
gaaccgaccg cgccgccgga agaaagcttt cgcagcggcg tggaaaccac caccccgccg   1740
cagaaacagg aaccgattga taaagaactg tatccgctga ccagcctgcg cagcctgttt   1800
ggcaacgatc cgagcagcca gtgatga                                       1827
```

<210> SEQ ID NO 15
<211> LENGTH: 173
<212> TYPE: PRT
<213> ORGANISM: Artificial Sequence
<220> FEATURE:
<221> NAME/KEY: PEPTIDE
<222> LOCATION: (1)..(173)
<223> OTHER INFORMATION: SEQ ID NO: 16 gp41 extracellular region (aa)

-continued

<400> SEQUENCE: 15

```
Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu
                165                 170
```

<210> SEQ ID NO 16
<211> LENGTH: 23
<212> TYPE: PRT
<213> ORGANISM: Artificial Sequence
<220> FEATURE:
<221> NAME/KEY: TRANSMEM
<222> LOCATION: (1)..(23)
<223> OTHER INFORMATION: SEQ ID NO: 17 gp41 transmembrane sequence (aa)

<400> SEQUENCE: 16

```
Trp Leu Trp Tyr Ile Lys Leu Phe Ile Met Ile Val Gly Gly Leu Val
1               5                   10                  15

Gly Leu Arg Ile Val Phe Ala
            20
```

<210> SEQ ID NO 17
<211> LENGTH: 19
<212> TYPE: PRT
<213> ORGANISM: Artificial Sequence
<220> FEATURE:
<221> NAME/KEY: TRANSMEM
<222> LOCATION: (1)..(19)
<223> OTHER INFORMATION: SEQ ID NO:18 CD22 transmembrane sequence (aa)

<400> SEQUENCE: 17

```
Val Ala Val Gly Leu Gly Ser Cys Leu Ala Ile Leu Ile Leu Ala Ile
1               5                   10                  15

Cys Gly Leu
```

<210> SEQ ID NO 18
<211> LENGTH: 22
<212> TYPE: PRT
<213> ORGANISM: Artificial Sequence
<220> FEATURE:
<221> NAME/KEY: TRANSMEM
<222> LOCATION: (1)..(22)
<223> OTHER INFORMATION: SEQ ID NO:19 CD36 transmembrane sequence

<400> SEQUENCE: 18

Leu Leu Gly Leu Ile Glu Met Ile Leu Leu Ser Val Gly Val Val Met
1               5                   10                  15

Phe Val Ala Phe Met Ile
            20

<210> SEQ ID NO 19
<211> LENGTH: 21
<212> TYPE: PRT
<213> ORGANISM: Artificial Sequence
<220> FEATURE:
<221> NAME/KEY: TRANSMEM
<222> LOCATION: (1)..(21)
<223> OTHER INFORMATION: SEQ ID NO: 20 CD44 transmembrane sequence (aa)

<400> SEQUENCE: 19

Trp Leu Ile Ile Leu Ala Ser Leu Leu Ala Leu Ala Leu Ile Leu Ala
1               5                   10                  15

Val Cys Ile Ala Val
            20

<210> SEQ ID NO 20
<211> LENGTH: 856
<212> TYPE: PRT
<213> ORGANISM: Artificial Sequence
<220> FEATURE:
<221> NAME/KEY: PEPTIDE
<222> LOCATION: (1)..(856)
<223> OTHER INFORMATION: HIV Env protein of gp160 (isolate HXB2) (aa)

<400> SEQUENCE: 20

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala

-continued

```
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640
```

Leu Ile His Ser Leu Ile Glu Glu Ser Gln Asn Gln Gln Glu Lys Asn
645 650 655

Glu Gln Glu Leu Leu Glu Leu Asp Lys Trp Ala Ser Leu Trp Asn Trp
660 665 670

Phe Asn Ile Thr Asn Trp Leu Trp Tyr Ile Lys Leu Phe Ile Met Ile
675 680 685

Val Gly Gly Leu Val Gly Leu Arg Ile Val Phe Ala Val Leu Ser Ile
690 695 700

Val Asn Arg Val Arg Gln Gly Tyr Ser Pro Leu Ser Phe Gln Thr His
705 710 715 720

Leu Pro Thr Pro Arg Gly Pro Asp Arg Pro Glu Gly Ile Glu Glu Glu
725 730 735

Gly Gly Glu Arg Asp Arg Asp Arg Ser Ile Arg Leu Val Asn Gly Ser
740 745 750

Leu Ala Leu Ile Trp Asp Asp Leu Arg Ser Leu Cys Leu Phe Ser Tyr
755 760 765

His Arg Leu Arg Asp Leu Leu Leu Ile Val Thr Arg Ile Val Glu Leu
770 775 780

Leu Gly Arg Arg Gly Trp Glu Ala Leu Lys Tyr Trp Trp Asn Leu Leu
785 790 795 800

Gln Tyr Trp Ser Gln Glu Leu Lys Asn Ser Ala Val Ser Leu Leu Asn
805 810 815

Ala Thr Ala Ile Ala Val Ala Glu Gly Thr Asp Arg Val Ile Glu Val
820 825 830

Val Gln Gly Ala Cys Arg Ala Ile Arg His Ile Pro Arg Arg Ile Arg
835 840 845

Gln Gly Leu Glu Arg Ile Leu Leu
850 855

<210> SEQ ID NO 21
<211> LENGTH: 41
<212> TYPE: PRT
<213> ORGANISM: Artificial Sequence
<220> FEATURE:
<221> NAME/KEY: PEPTIDE
<222> LOCATION: (1)..(41)
<223> OTHER INFORMATION: SEQ ID NO: 22 HR2 region (aa)

<400> SEQUENCE: 21

Met Ile Trp Asn Asn Met Thr Trp Met Glu Trp Asp Arg Glu Ile Asn
1 5 10 15

Asn Tyr Thr Ser Leu Ile His Ser Leu Ile Glu Glu Ser Gln Asn Gln
20 25 30

Gln Glu Lys Asn Glu Gln Glu Leu Leu
35 40

<210> SEQ ID NO 22
<211> LENGTH: 22
<212> TYPE: PRT
<213> ORGANISM: Artificial Sequence
<220> FEATURE:
<221> NAME/KEY: PEPTIDE
<222> LOCATION: (1)..(22)
<223> OTHER INFORMATION: SEQ ID NO: 23 MPER region (aa)

<400> SEQUENCE: 22

Glu Leu Asp Lys Trp Ala Ser Leu Trp Asn Trp Phe Asn Ile Thr Asn
1 5 10 15

Trp Leu Trp Tyr Ile Lys
20

<210> SEQ ID NO 23
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: SEQ ID NO: 24 GS linker (aa)

<400> SEQUENCE: 23

Gly Gly Gly Ser
1

<210> SEQ ID NO 24
<211> LENGTH: 13
<212> TYPE: PRT
<213> ORGANISM: Artificial Sequence
<220> FEATURE:
<221> NAME/KEY: PEPTIDE
<222> LOCATION: (1)..(13)
<223> OTHER INFORMATION: SEQ ID NO: 25 Linker (aa)

<400> SEQUENCE: 24

Gly Gly Gly Gly Lys Gly Gln Asp Asn Ser Ala Asp Ile
1 5 10

<210> SEQ ID NO 25
<211> LENGTH: 12
<212> TYPE: PRT
<213> ORGANISM: Artificial Sequence
<220> FEATURE:
<221> NAME/KEY: PEPTIDE
<222> LOCATION: (1)..(12)
<223> OTHER INFORMATION: SEQ ID NO: 26 Linker (aa)

<400> SEQUENCE: 25

Gly Ser Ala Gly Ser Ala Ala Gly Ser Gly Glu Phe
1 5 10

<210> SEQ ID NO 26
<211> LENGTH: 7
<212> TYPE: PRT
<213> ORGANISM: Artificial Sequence
<220> FEATURE:
<221> NAME/KEY: PEPTIDE
<222> LOCATION: (1)..(7)
<223> OTHER INFORMATION: SEQ ID NO: 27 Linker (aa)

<400> SEQUENCE: 26

Ala Glu Ala Ala Ala Lys Ala
1 5

<210> SEQ ID NO 27
<211> LENGTH: 7
<212> TYPE: PRT
<213> ORGANISM: Artificial Sequence
<220> FEATURE:
<221> NAME/KEY: PEPTIDE
<222> LOCATION: (1)..(7)
<223> OTHER INFORMATION: SEQ ID NO: 28 Linker (aa)

<400> SEQUENCE: 27

Ala Pro Ala Pro Ala Pro Ala
1 5

<210> SEQ ID NO 28
<211> LENGTH: 635
<212> TYPE: PRT
<213> ORGANISM: Artificial Sequence
<220> FEATURE:
<221> NAME/KEY: PEPTIDE
<222> LOCATION: (1)..(635)
<223> OTHER INFORMATION: MINGAG3.7 fusion protein (aa)

<400> SEQUENCE: 28

```
Met Ile Trp Asn Asn Met Thr Trp Met Glu Trp Asp Arg Glu Ile Asn
1               5                   10                  15

Asn Tyr Thr Ser Leu Ile His Ser Leu Ile Glu Glu Ser Gln Asn Gln
            20                  25                  30

Gln Glu Lys Asn Glu Gln Glu Leu Leu Glu Leu Asp Lys Trp Ala Ser
        35                  40                  45

Leu Trp Asn Trp Phe Asn Ile Thr Asn Trp Leu Trp Tyr Ile Lys Leu
    50                  55                  60

Phe Ile Met Ile Val Gly Gly Leu Val Gly Leu Arg Ile Val Phe Ala
65                  70                  75                  80

Val Leu Ser Ile Val Asn Arg Ala Gly Gly Gly Gly Lys Gly Gln Asp
                85                  90                  95

Asn Ser Ala Asp Ile Gly Ala Arg Ala Ser Val Leu Ser Gly Gly Glu
            100                 105                 110

Leu Asp Arg Trp Gly Lys Ile Arg Leu Arg Pro Gly Gly Lys Lys Lys
        115                 120                 125

Tyr Lys Leu Lys His Ile Val Trp Ala Ser Arg Glu Leu Glu Arg Phe
    130                 135                 140

Ala Val Asn Pro Gly Leu Leu Glu Thr Ser Glu Gly Cys Arg Gln Ile
145                 150                 155                 160

Leu Gly Gln Leu Gln Pro Ser Leu Gln Thr Gly Ser Glu Glu Leu Arg
                165                 170                 175

Ser Leu Tyr Asn Thr Val Ala Thr Leu Tyr Cys Val His Gln Arg Ile
            180                 185                 190

Glu Ile Lys Asp Thr Lys Glu Ala Leu Asp Lys Ile Glu Glu Glu Gln
        195                 200                 205

Asn Lys Ser Lys Lys Lys Ala Gln Gln Ala Ala Ala Asp Thr Gly His
    210                 215                 220

Ser Asn Gln Val Ser Gln Asn Tyr Pro Ile Val Gln Asn Ile Gln Gly
225                 230                 235                 240

Gln Met Val His Gln Ala Ile Ser Pro Arg Thr Leu Asn Ala Trp Val
                245                 250                 255

Lys Val Val Glu Glu Lys Ala Phe Ser Pro Glu Val Ile Pro Met Phe
            260                 265                 270

Ser Ala Leu Ser Glu Gly Ala Thr Pro Gln Asp Leu Asn Thr Met Leu
        275                 280                 285

Asn Thr Val Gly Gly His Gln Ala Ala Met Gln Met Leu Lys Glu Thr
    290                 295                 300

Ile Asn Glu Glu Ala Ala Glu Trp Asp Arg Val His Pro Val His Ala
305                 310                 315                 320

Gly Pro Ile Ala Pro Gly Gln Met Arg Glu Pro Arg Gly Ser Asp Ile
                325                 330                 335

Ala Gly Thr Thr Ser Thr Leu Gln Glu Gln Ile Gly Trp Met Thr Asn
            340                 345                 350

Asn Pro Pro Ile Pro Val Gly Glu Ile Tyr Lys Arg Trp Ile Ile Leu
        355                 360                 365
```

```
Gly Leu Asn Lys Ile Val Arg Met Tyr Ser Pro Thr Ser Ile Leu Asp
    370                 375                 380

Ile Arg Gln Gly Pro Lys Glu Pro Phe Arg Asp Tyr Val Asp Arg Phe
385                 390                 395                 400

Tyr Lys Thr Leu Arg Ala Glu Gln Ala Ser Gln Glu Val Lys Asn Trp
                405                 410                 415

Met Thr Glu Thr Leu Leu Val Gln Asn Ala Asn Pro Asp Cys Lys Thr
            420                 425                 430

Ile Leu Lys Ala Leu Gly Pro Ala Ala Thr Leu Glu Glu Met Met Thr
        435                 440                 445

Ala Cys Gln Gly Val Gly Gly Pro Gly His Lys Ala Arg Val Leu Ala
    450                 455                 460

Glu Ala Met Ser Gln Val Thr Asn Ser Ala Thr Ile Met Met Gln Arg
465                 470                 475                 480

Gly Asn Phe Arg Asn Gln Arg Lys Ile Val Lys Cys Phe Asn Cys Gly
                485                 490                 495

Lys Glu Gly His Thr Ala Arg Asn Cys Arg Ala Pro Arg Lys Lys Gly
            500                 505                 510

Cys Trp Lys Cys Gly Lys Glu Gly His Gln Met Lys Asp Cys Thr Glu
        515                 520                 525

Arg Gln Ala Asn Phe Leu Gly Lys Ile Trp Pro Ser Tyr Lys Gly Arg
    530                 535                 540

Pro Gly Asn Phe Leu Gln Ser Arg Pro Glu Pro Thr Ala Pro Pro Glu
545                 550                 555                 560

Glu Ser Phe Arg Ser Gly Val Glu Thr Thr Thr Pro Pro Gln Lys Gln
                565                 570                 575

Glu Pro Ile Asp Lys Glu Leu Tyr Pro Leu Thr Ser Leu Arg Ser Leu
            580                 585                 590

Phe Gly Asn Asp Pro Ser Ser Gln Gly Gly Arg Ser Ser Leu Glu Gly
        595                 600                 605

Pro Arg Phe Glu Gly Lys Pro Ile Pro Asn Pro Leu Leu Gly Leu Asp
    610                 615                 620

Ser Thr Arg Thr Gly His His His His His His
625                 630                 635
```

<210> SEQ ID NO 29
<211> LENGTH: 72
<212> TYPE: DNA
<213> ORGANISM: Artificial Sequence
<220> FEATURE:
<221> NAME/KEY: gene
<222> LOCATION: (1)..(72)
<223> OTHER INFORMATION: SEQ ID NO: 30 HIV R696A mutated transmembrane domain (nt)

<400> SEQUENCE: 29

```
ctgttcatca tgatcgtcgg cggcctcgtt ggactggcca ttgtgtttgc cgtgctgagc     60

atcgtgaaca ga                                                         72
```

<210> SEQ ID NO 30
<211> LENGTH: 24
<212> TYPE: PRT
<213> ORGANISM: Artificial Sequence
<220> FEATURE:
<221> NAME/KEY: TRANSMEM
<222> LOCATION: (1)..(24)
<223> OTHER INFORMATION: SEQ ID NO: 31 HIV R696A mutated transmembrane domain (aa)

<400> SEQUENCE: 30

Leu Phe Ile Met Ile Val Gly Gly Leu Val Gly Leu Ala Ile Val Phe
1               5                   10                  15

Ala Val Leu Ser Ile Val Asn Arg
            20

<210> SEQ ID NO 31
<211> LENGTH: 1830
<212> TYPE: DNA
<213> ORGANISM: Artificial Sequence
<220> FEATURE:
<221> NAME/KEY: gene
<222> LOCATION: (1)..(1830)
<223> OTHER INFORMATION: SEQ ID NO: 32 HCV engrafted MINGAG fusion
      protein (including, the HR2 region of HIVgp41, the neutralizing
      HCV epitope XX, the c-term moiety of the HIVgp41 MPER the TM of
      HIVgp41, a GGGGS linker and the GAG sequence devoid of
      myristoylation signal (nt)

<400> SEQUENCE: 31
atgtggctgc aatctctgct gctgctgggc acagtggcct gcagcatcag catctggaat     60
cacaccacct ggatggaatg ggaccgcgag atcaacaact acaccagcct gatccacagc    120
ctgattgagg aaagccagaa ccagcaagag aagcagaaca tccagctgat caacaccaac    180
ggcagctggc acagcctgtg gaactggttc aacatcacca actggctgtg gtacatcaag    240
ctgttcatca tgatcgtcgg cggcctcgtg ggcctgagaa ttgtgtttgc cgtgctgagc    300
atcgtgaaca gaggtggcgg aggatccggc gctagagctt ctgtgctgtc tgggggcgaa    360
ctggatagat gggagaagat ccggctgcgg cctggcggca agaagaagta caagctgaag    420
cacatcgtgt gggcctccag agagctggaa agattcgccg tgaaccccgg cctgctggaa    480
accagcgagg gctgcagaca gatcctggga cagctgcagc ccagcctgca gaccggaagc    540
gaggaactgc ggagcctgta caacaccgtg gccacactgt attgcgtgca ccagcggatc    600
gagatcaagg acaccaaaga ggccctggac aagatcgagg aagaacagaa caagtctaag    660
aagaaggccc agcaggctgc cgccgatacc ggccactcta atcaggtgtc ccagaactac    720
cccatcgtgc agaacatcca gggccagatg gtgcatcagg ccatcagccc cagaaccctg    780
aacgcctggg tcaaggtggt ggaagagaag gcctttagcc ccgaagtgat ccccatgttc    840
agcgccctgt ctgagggcgc cacaccccag gacctgaaca ccatgctgaa cacagtgggc    900
ggacaccagg ccgccatgca gatgctgaaa gagacaatca acgaagaggc cgccgagtgg    960
gacagagtgc accctgtgca tgccggacct atcgcccctg gccagatgag agagcccaga   1020
ggctctgata tcgccggcac caccagcacc ctgcaggaac agatcggctg gatgaccaac   1080 aacccccca tccccgtggg cgagatctac aagcggtgga tcatcctggg cctgaacaag   1140
attgtgcgga tgtacagccc cacctccatc ctggacatcc ggcagggccc caaagagccc   1200
ttcagagact acgtggaccg gttctacaag accctgagag ccgagcaggc cagccaggaa   1260
gtgaagaatt ggatgaccga gacactgctg gtgcagaacg ccaaccccga ctgcaagacc   1320
atcctgaagg ccctgggacc tgccgccacc ctggaagaga tgatgacagc ctgtcagggc   1380
gtgggaggcc caggccacaa agctagagtg ctggccgagg ccatgagcca agtgaccaac   1440
tccgccacca ttatgatgca gcggggcaac ttccggaacc agcggaagat cgtgaagtgc   1500
ttcaactgcg gcaaagaggg ccacaccgcc cggaattgca gagcccccag aaagaaaggc   1560
tgctggaagt gtggaaaaga ggggcaccag atgaaggact gcaccgagcg gcaggccaac   1620

-continued

```
ttcctgggca agatctggcc tagctacaag ggcagacccg gcaatttcct gcagagcaga   1680

cccgagccta ccgcccctcc cgaggaaagc tttagaagcg gcgtggaaac caccaccccc   1740

ccacagaagc aggaacccat cgacaaagag ctgtaccccc tgaccagcct gagaagcctg   1800

ttcggcaacg accccagcag ccagtgatga                                    1830


<210> SEQ ID NO 32
<211> LENGTH: 608
<212> TYPE: PRT
<213> ORGANISM: Artificial Sequence
<220> FEATURE:
<221> NAME/KEY: PEPTIDE
<222> LOCATION: (1)..(608)
<223> OTHER INFORMATION: SEQ ID NO: 33 HCV engrafted MINGAG fusion
      protein (including, the HR2 region of HIVgp41, the neutralizing
      HCV epitope XX, the c-term moiety of the HIVgp41 MPER the TM of
      HIVgp41, a GGGGS linker and the GAG sequence devoid of
      myristoylation signal (aa)

<400> SEQUENCE: 32

Met Trp Leu Gln Ser Leu Leu Leu Leu Gly Thr Val Ala Cys Ser Ile
1               5                   10                  15

Ser Ile Trp Asn His Thr Thr Trp Met Glu Trp Asp Arg Glu Ile Asn
            20                  25                  30

Asn Tyr Thr Ser Leu Ile His Ser Leu Ile Glu Glu Ser Gln Asn Gln
        35                  40                  45

Gln Glu Lys Gln Asn Ile Gln Leu Ile Asn Thr Asn Gly Ser Trp His
    50                  55                  60

Ser Leu Trp Asn Trp Phe Asn Ile Thr Asn Trp Leu Trp Tyr Ile Lys
65                  70                  75                  80

Leu Phe Ile Met Ile Val Gly Gly Leu Val Gly Leu Arg Ile Val Phe
                85                  90                  95

Ala Val Leu Ser Ile Val Asn Arg Gly Gly Gly Gly Ser Gly Ala Arg
            100                 105                 110

Ala Ser Val Leu Ser Gly Gly Glu Leu Asp Arg Trp Glu Lys Ile Arg
        115                 120                 125

Leu Arg Pro Gly Gly Lys Lys Lys Tyr Lys Leu Lys His Ile Val Trp
    130                 135                 140

Ala Ser Arg Glu Leu Glu Arg Phe Ala Val Asn Pro Gly Leu Leu Glu
145                 150                 155                 160

Thr Ser Glu Gly Cys Arg Gln Ile Leu Gly Gln Leu Gln Pro Ser Leu
                165                 170                 175

Gln Thr Gly Ser Glu Glu Leu Arg Ser Leu Tyr Asn Thr Val Ala Thr
            180                 185                 190

Leu Tyr Cys Val His Gln Arg Ile Glu Ile Lys Asp Thr Lys Glu Ala
        195                 200                 205

Leu Asp Lys Ile Glu Glu Glu Gln Asn Lys Ser Lys Lys Lys Ala Gln
    210                 215                 220

Gln Ala Ala Ala Asp Thr Gly His Ser Asn Gln Val Ser Gln Asn Tyr
225                 230                 235                 240

Pro Ile Val Gln Asn Ile Gln Gly Gln Met Val His Gln Ala Ile Ser
                245                 250                 255

Pro Arg Thr Leu Asn Ala Trp Val Lys Val Val Glu Glu Lys Ala Phe
            260                 265                 270

Ser Pro Glu Val Ile Pro Met Phe Ser Ala Leu Ser Glu Gly Ala Thr
        275                 280                 285

Pro Gln Asp Leu Asn Thr Met Leu Asn Thr Val Gly Gly His Gln Ala
```

```
    290                 295                 300

Ala Met Gln Met Leu Lys Glu Thr Ile Asn Glu Glu Ala Ala Glu Trp
305                 310                 315                 320

Asp Arg Val His Pro Val His Ala Gly Pro Ile Ala Pro Gly Gln Met
                325                 330                 335

Arg Glu Pro Arg Gly Ser Asp Ile Ala Gly Thr Thr Ser Thr Leu Gln
            340                 345                 350

Glu Gln Ile Gly Trp Met Thr Asn Asn Pro Pro Ile Pro Val Gly Glu
        355                 360                 365

Ile Tyr Lys Arg Trp Ile Ile Leu Gly Leu Asn Lys Ile Val Arg Met
    370                 375                 380

Tyr Ser Pro Thr Ser Ile Leu Asp Ile Arg Gln Gly Pro Lys Glu Pro
385                 390                 395                 400

Phe Arg Asp Tyr Val Asp Arg Phe Tyr Lys Thr Leu Arg Ala Glu Gln
                405                 410                 415

Ala Ser Gln Glu Val Lys Asn Trp Met Thr Glu Thr Leu Leu Val Gln
            420                 425                 430

Asn Ala Asn Pro Asp Cys Lys Thr Ile Leu Lys Ala Leu Gly Pro Ala
        435                 440                 445

Ala Thr Leu Glu Glu Met Met Thr Ala Cys Gln Gly Val Gly Gly Pro
    450                 455                 460

Gly His Lys Ala Arg Val Leu Ala Glu Ala Met Ser Gln Val Thr Asn
465                 470                 475                 480

Ser Ala Thr Ile Met Met Gln Arg Gly Asn Phe Arg Asn Gln Arg Lys
                485                 490                 495

Ile Val Lys Cys Phe Asn Cys Gly Lys Glu Gly His Thr Ala Arg Asn
            500                 505                 510

Cys Arg Ala Pro Arg Lys Lys Gly Cys Trp Lys Cys Gly Lys Glu Gly
        515                 520                 525

His Gln Met Lys Asp Cys Thr Glu Arg Gln Ala Asn Phe Leu Gly Lys
    530                 535                 540

Ile Trp Pro Ser Tyr Lys Gly Arg Pro Gly Asn Phe Leu Gln Ser Arg
545                 550                 555                 560

Pro Glu Pro Thr Ala Pro Pro Glu Glu Ser Phe Arg Ser Gly Val Glu
                565                 570                 575

Thr Thr Thr Pro Pro Gln Lys Gln Glu Pro Ile Asp Lys Glu Leu Tyr
            580                 585                 590

Pro Leu Thr Ser Leu Arg Ser Leu Phe Gly Asn Asp Pro Ser Ser Gln
        595                 600                 605


<210> SEQ ID NO 33
<211> LENGTH: 2202
<212> TYPE: DNA
<213> ORGANISM: Artificial Sequence
<220> FEATURE:
<221> NAME/KEY: gene
<222> LOCATION: (1)..(2202)
<223> OTHER INFORMATION: HCV E2 protein fused to GAG (HCVE2/GAGcop)
      including, the mosaic HCV E2 design  the TM of HCVE2 mutated at
      the RxxxA, a GS linker and the HIV GAG sequence devoid of
      myristoylation signal (nt)

<400> SEQUENCE: 33

atgttcagcc atctgccttt cgactgcgtg ctgctgctcc tgcttctgct gctgacaaga      60

agccagctga tcaacaccaa cggcagctgg cacatcaaca gcacagccct gaactgcaac     120

gagagcctga ataccggatg gctggccggc ctgttctacc agcacaagtt caatagcagc     180
```

-continued

```
ggctgccccg agagactggc cagctgtgga tcttctggct gctggcacta ccctccaaga    240
ccttgtggaa tcgtgcccgc caagtctgtg tgtggccctg tgtactgctt caccccatct    300
ccagtggtcg tgggcaccac cgatagatct ggcgccccaa catatagctg ggagccaac     360
gacaccgacg tgttcgtgct gaacaatacc agacctcctc tcggcaattg gttcggctgc    420
acctggatga acagcaccgg cttcacaaaa gtgtgcggag cccctccatg tggcagctcc    480
ggctgtagct ttaccacact gcctgctctg agcaccggcc tgattcatct gcaccagaac    540
atcgtggacg tgcagtacct gtacggcgtg ggaagctcta ttgccagctg ggccatcaag    600
tgggagtacg tggtgctgct gtttctgctc ctggccgatg ccgccgtgtg tagctgtctg    660
tggatgatgc tgctgatctc ccaggccgaa gctggatccg gcgctagagc ttctgtgctg    720
tctgggggcg aactggatag atgggagaag atccggctgc ggcctggcgg caagaagaag    780
tacaagctga agcacatcgt gtgggcctcc agagagctgg aaagattcgc cgtgaacccc    840
ggcctgctgg aaaccagcga gggctgcaga cagatcctgg gacagctgca gcccagcctg    900
cagaccggaa gcgaggaact gcggagcctg tacaacaccg tggccacact gtattgcgtg    960
caccagcgga tcgagatcaa ggacaccaaa gaggccctgg acaagatcga ggaagaacag   1020
aacaagtcta agaagaaggc ccagcaggct gccgccgata ccggccactc taatcaggtg   1080
tcccagaact accccatcgt gcagaacatc cagggccaga tggtgcatca ggccatcagc   1140
cccagaaccc tgaacgcctg ggtcaaggtg gtggaagaga aggcctttag ccccgaagtg   1200
atccccatgt tcagcgccct gtctgagggc gccacacccc aggacctgaa caccatgctg   1260
aacacagtgg gcggacacca ggccgccatg cagatgctga aagagacaat caacgaagag   1320
gccgccgagt gggacagagt gcaccctgtg catgccggac ctatcgcccc tggccagatg   1380
agagagccca gaggctctga tatcgccggc accaccagca ccctgcagga acagatcggc   1440
tggatgacca acaacccccc catccccgtg ggcgagatct acaagcggtg gatcatcctg   1500
ggcctgaaca agattgtgcg gatgtacagc cccacctcca tcctggacat ccggcagggc   1560
cccaaagagc ccttcagaga ctacgtggac cggttctaca agaccctgag agccgagcag   1620
gccagccagg aagtgaagaa ttggatgacc gagacactgc tggtgcagaa cgccaacccc   1680
gactgcaaga ccatcctgaa ggccctggga cctgccgcca ccctggaaga gatgatgaca   1740
gcctgtcagg gcgtgggagg cccaggccac aaagctagag tgctggccga ggccatgagc   1800
caagtgacca actccgccac cattatgatg cagcggggca acttccggaa ccagcggaag   1860
atcgtgaagt gcttcaactg cggcaaagag ggccacaccg cccggaattg cagagccccc   1920
agaaagaaag gctgctggaa gtgtggaaaa gaggggcacc agatgaagga ctgcaccgag   1980
cggcaggcca acttcctggg caagatctgg cctagctaca agggcagacc cggcaatttc   2040
ctgcagagca gacccgagcc taccgcccct cccgaggaaa gctttagaag cggcgtggaa   2100
accaccaccc ccccacagaa gcaggaaccc atcgacaaag agctgtaccc cctgaccagc   2160
ctgagaagcc tgttcggcaa cgaccccagc agccagtgat ga                      2202
```

```
<210> SEQ ID NO 34
<211> LENGTH: 732
<212> TYPE: PRT
<213> ORGANISM: Artificial Sequence
<220> FEATURE:
<221> NAME/KEY: PEPTIDE
<222> LOCATION: (1)..(732)
<223> OTHER INFORMATION: SEQ ID NO: 35 HCV E2 protein fused to GAG
      (HCVE2/GAGcop) including, the mosaic HCV E2 design  the TM of
```

-continued

HCVE2 mutated at the RxxxA, a GS linker and the HIV GAG sequence
devoid of myristoylation signal (aa)

<400> SEQUENCE: 34

Met Phe Ser His Leu Pro Phe Asp Cys Val Leu Leu Leu Leu Leu Leu
1               5                   10                  15

Leu Leu Thr Arg Ser Gln Leu Ile Asn Thr Asn Gly Ser Trp His Ile
            20                  25                  30

Asn Ser Thr Ala Leu Asn Cys Asn Glu Ser Leu Asn Thr Gly Trp Leu
        35                  40                  45

Ala Gly Leu Phe Tyr Gln His Lys Phe Asn Ser Ser Gly Cys Pro Glu
    50                  55                  60

Arg Leu Ala Ser Cys Gly Ser Ser Gly Cys Trp His Tyr Pro Pro Arg
65                  70                  75                  80

Pro Cys Gly Ile Val Pro Ala Lys Ser Val Cys Gly Pro Val Tyr Cys
                85                  90                  95

Phe Thr Pro Ser Pro Val Val Val Gly Thr Thr Asp Arg Ser Gly Ala
            100                 105                 110

Pro Thr Tyr Ser Trp Gly Ala Asn Asp Thr Asp Val Phe Val Leu Asn
        115                 120                 125

Asn Thr Arg Pro Pro Leu Gly Asn Trp Phe Gly Cys Thr Trp Met Asn
    130                 135                 140

Ser Thr Gly Phe Thr Lys Val Cys Gly Ala Pro Pro Cys Gly Ser Ser
145                 150                 155                 160

Gly Cys Ser Phe Thr Thr Leu Pro Ala Leu Ser Thr Gly Leu Ile His
                165                 170                 175

Leu His Gln Asn Ile Val Asp Val Gln Tyr Leu Tyr Gly Val Gly Ser
            180                 185                 190

Ser Ile Ala Ser Trp Ala Ile Lys Trp Glu Tyr Val Val Leu Leu Phe
        195                 200                 205

Leu Leu Leu Ala Asp Ala Ala Val Cys Ser Cys Leu Trp Met Met Leu
    210                 215                 220

Leu Ile Ser Gln Ala Glu Ala Gly Ser Gly Ala Arg Ala Ser Val Leu
225                 230                 235                 240

Ser Gly Gly Glu Leu Asp Arg Trp Glu Lys Ile Arg Leu Arg Pro Gly
                245                 250                 255

Gly Lys Lys Lys Tyr Lys Leu Lys His Ile Val Trp Ala Ser Arg Glu
            260                 265                 270

Leu Glu Arg Phe Ala Val Asn Pro Gly Leu Leu Glu Thr Ser Glu Gly
        275                 280                 285

Cys Arg Gln Ile Leu Gly Gln Leu Gln Pro Ser Leu Gln Thr Gly Ser
    290                 295                 300

Glu Glu Leu Arg Ser Leu Tyr Asn Thr Val Ala Thr Leu Tyr Cys Val
305                 310                 315                 320

His Gln Arg Ile Glu Ile Lys Asp Thr Lys Glu Ala Leu Asp Lys Ile
                325                 330                 335

Glu Glu Glu Gln Asn Lys Ser Lys Lys Lys Ala Gln Gln Ala Ala Ala
            340                 345                 350

Asp Thr Gly His Ser Asn Gln Val Ser Gln Asn Tyr Pro Ile Val Gln
        355                 360                 365

Asn Ile Gln Gly Gln Met Val His Gln Ala Ile Ser Pro Arg Thr Leu
    370                 375                 380

Asn Ala Trp Val Lys Val Val Glu Glu Lys Ala Phe Ser Pro Glu Val
385                 390                 395                 400

Ile Pro Met Phe Ser Ala Leu Ser Glu Gly Ala Thr Pro Gln Asp Leu
405 410 415

Asn Thr Met Leu Asn Thr Val Gly Gly His Gln Ala Ala Met Gln Met
420 425 430

Leu Lys Glu Thr Ile Asn Glu Glu Ala Ala Glu Trp Asp Arg Val His
435 440 445

Pro Val His Ala Gly Pro Ile Ala Pro Gly Gln Met Arg Glu Pro Arg
450 455 460

Gly Ser Asp Ile Ala Gly Thr Thr Ser Thr Leu Gln Glu Gln Ile Gly
465 470 475 480

Trp Met Thr Asn Asn Pro Pro Ile Pro Val Gly Glu Ile Tyr Lys Arg
485 490 495

Trp Ile Ile Leu Gly Leu Asn Lys Ile Val Arg Met Tyr Ser Pro Thr
500 505 510

Ser Ile Leu Asp Ile Arg Gln Gly Pro Lys Glu Pro Phe Arg Asp Tyr
515 520 525

Val Asp Arg Phe Tyr Lys Thr Leu Arg Ala Glu Gln Ala Ser Gln Glu
530 535 540

Val Lys Asn Trp Met Thr Glu Thr Leu Leu Val Gln Asn Ala Asn Pro
545 550 555 560

Asp Cys Lys Thr Ile Leu Lys Ala Leu Gly Pro Ala Ala Thr Leu Glu
565 570 575

Glu Met Met Thr Ala Cys Gln Gly Val Gly Gly Pro Gly His Lys Ala
580 585 590

Arg Val Leu Ala Glu Ala Met Ser Gln Val Thr Asn Ser Ala Thr Ile
595 600 605

Met Met Gln Arg Gly Asn Phe Arg Asn Gln Arg Lys Ile Val Lys Cys
610 615 620

Phe Asn Cys Gly Lys Glu Gly His Thr Ala Arg Asn Cys Arg Ala Pro
625 630 635 640

Arg Lys Lys Gly Cys Trp Lys Cys Gly Lys Glu Gly His Gln Met Lys
645 650 655

Asp Cys Thr Glu Arg Gln Ala Asn Phe Leu Gly Lys Ile Trp Pro Ser
660 665 670

Tyr Lys Gly Arg Pro Gly Asn Phe Leu Gln Ser Arg Pro Glu Pro Thr
675 680 685

Ala Pro Pro Glu Glu Ser Phe Arg Ser Gly Val Glu Thr Thr Thr Pro
690 695 700

Pro Gln Lys Gln Glu Pro Ile Asp Lys Glu Leu Tyr Pro Leu Thr Ser
705 710 715 720

Leu Arg Ser Leu Phe Gly Asn Asp Pro Ser Ser Gln
725 730

<210> SEQ ID NO 35
<211> LENGTH: 2406
<212> TYPE: DNA
<213> ORGANISM: Artificial Sequence
<220> FEATURE:
<221> NAME/KEY: gene
<222> LOCATION: (1)..(2406)
<223> OTHER INFORMATION: SEQ ID NO: 36 Borrelia OspA protein fused to HIV GAG (ospA/GAGcop) including a human signal peptide (from TIM-3) the 17-273 sequence of ospA, a human CD44 TM, a GS linker and the HIV GAG sequence devoid of myristoylation signal (nt)

<400> SEQUENCE: 35

-continued

```
atgttcagcc atctgccttt cgactgcgtg ctgctgctcc tgcttctgct gctgaccaga     60
tcctgcaagc agaacgtgtc cagcctggac gagaagaaca gcgtgtccgt tgatctgccc    120
ggcgagatga aggtgctggt gtccaaagag aaaaacaagg acgggaagta cgacctgatc    180
gccaccgtgg acaagctgga actgaagggc accagcgaca agaacaatgg cagcggagtg    240
ctggaaggcg tgaaggccga taagagcaaa gtgaagctga ccatcagcga cgacctgggc    300
cagaccacac tggaagtgtt caaagaggac ggcaagaccc tggtgtctaa gaaagtgacc    360
agcaaggaca agagcagcac cgaggaaaag ttcaacgaga agggcgaagt gtccgagaag    420
atcatcacca gagccgacgg caccagactc gagtacacag gcatcaagtc cgacggcagc    480
ggcaaggcca aagaggtgct gaaaggctac gtgctcgagg gcacactgac cgccgagaaa    540
acaaccctgg tggtcaaaga gggcaccgtc acactgagca agaacatcag caagagcggc    600
gaggtgtccg tcgagctgaa cgatacagat agcagcgccg ccaccaagaa aaccgccgcc    660
tggaatagcg gcacaagcac cctgacaatc accgtgaaca gcaaaaagac caaggacctg    720
gtgttcacca aagaaaacac catcaccgtg cagcagtacg acagcaacgg caccaaactg    780
gaaggcagcg ccgtggaaat caccaagctg gatgagatca agaacgccct gaagtggctg    840
atcatcctgg ccagtctgct ggccctggct ctgattctgg ccgtgtgtat tgctgtggga    900
tccggcgcta gagcttctgt gctgtctggg ggcgaactgg atagatggga gaagatccgg    960
ctgcggcctg gcggcaagaa gaagtacaag ctgaagcaca tcgtgtgggc ctccagagag   1020
ctggaaagat tcgccgtgaa ccccggcctg ctggaaacca gcgagggctg cagacagatc   1080
ctgggacagc tgcagcccag cctgcagacc ggaagcgagg aactgcggag cctgtacaac   1140
accgtggcca cactgtattg cgtgcaccag cggatcgaga tcaaggacac caaagaggcc   1200
ctggacaaga tcgaggaaga acagaacaag tctaagaaga aggcccagca ggctgccgcc   1260
gataccggcc actctaatca ggtgtcccag aactacccca tcgtgcagaa catccagggc   1320
cagatggtgc atcaggccat cagccccaga accctgaacg cctgggtcaa ggtggtggaa   1380
gagaaggcct ttagccccga agtgatcccc atgttcagcg ccctgtctga gggcgccaca   1440
ccccaggacc tgaacaccat gctgaacaca gtgggcggac accaggccgc catgcagatg   1500
ctgaaagaga caatcaacga agaggccgcc gagtgggaca gagtgcaccc tgtgcatgcc   1560
ggacctatcg cccctggcca gatgagagag cccagaggct ctgatatcgc cggcaccacc   1620
agcaccctgc aggaacagat cggctggatg accaacaacc cccccatccc cgtgggcgag   1680
atctacaagc ggtggatcat cctgggcctg aacaagattg tgcggatgta cagccccacc   1740
tccatcctgg acatccggca gggccccaaa gagcccttca gagactacgt ggaccggttc   1800
tacaagaccc tgagagccga gcaggccagc caggaagtga agaattggat gaccgagaca   1860
ctgctggtgc agaacgccaa ccccgactgc aagaccatcc tgaaggccct gggacctgcc   1920
gccaccctgg aagagatgat gacagcctgt cagggcgtgg gaggccccag ccacaaagct   1980
agagtgctgg ccgaggccat gagccaagtg accaactccg ccaccattat gatgcagcgg   2040
ggcaacttcc ggaaccagcg gaagatcgtg aagtgcttca actgcggcaa agagggccac   2100
accgcccgga attgcagagc ccccagaaag aaaggctgct ggaagtgtgg aaaagagggg   2160
caccagatga aggactgcac cgagcggcag gccaacttcc tgggcaagat ctggcctagc   2220
tacaagggca gacccggcaa tttcctgcag agcagacccg agcctaccgc ccctcccgag   2280
gaaagcttta gaagcggcgt ggaaaccacc acccccccac agaagcagga acccatcgac   2340
aaagagctgt acccccctgac cagcctgaga agcctgttcg gcaacgaccc cagcagccag   2400
```

tgatga 2406

<210> SEQ ID NO 36
<211> LENGTH: 800
<212> TYPE: PRT
<213> ORGANISM: Artificial Sequence
<220> FEATURE:
<221> NAME/KEY: PEPTIDE
<222> LOCATION: (1)..(800)
<223> OTHER INFORMATION: SEQ ID NO: 37 Borrelia OspA protein fused to HIV GAG (ospA/GAGcop) including a human signal peptide (from TIM-3) the 17-273 sequence of ospA, a human CD44 TM, a GS linker and the HIV GAG sequence devoid of myristoylation signal (aa)

<400> SEQUENCE: 36

Met Phe Ser His Leu Pro Phe Asp Cys Val Leu Leu Leu Leu Leu Leu
1 5 10 15

Leu Leu Thr Arg Ser Cys Lys Gln Asn Val Ser Ser Leu Asp Glu Lys
20 25 30

Asn Ser Val Ser Val Asp Leu Pro Gly Glu Met Lys Val Leu Val Ser
35 40 45

Lys Glu Lys Asn Lys Asp Gly Lys Tyr Asp Leu Ile Ala Thr Val Asp
50 55 60

Lys Leu Glu Leu Lys Gly Thr Ser Asp Lys Asn Asn Gly Ser Gly Val
65 70 75 80

Leu Glu Gly Val Lys Ala Asp Lys Ser Lys Val Lys Leu Thr Ile Ser
85 90 95

Asp Asp Leu Gly Gln Thr Thr Leu Glu Val Phe Lys Glu Asp Gly Lys
100 105 110

Thr Leu Val Ser Lys Lys Val Thr Ser Lys Asp Lys Ser Ser Thr Glu
115 120 125

Glu Lys Phe Asn Glu Lys Gly Glu Val Ser Glu Lys Ile Ile Thr Arg
130 135 140

Ala Asp Gly Thr Arg Leu Glu Tyr Thr Gly Ile Lys Ser Asp Gly Ser
145 150 155 160

Gly Lys Ala Lys Glu Val Leu Lys Gly Tyr Val Leu Glu Gly Thr Leu
165 170 175

Thr Ala Glu Lys Thr Thr Leu Val Val Lys Glu Gly Thr Val Thr Leu
180 185 190

Ser Lys Asn Ile Ser Lys Ser Gly Glu Val Ser Val Glu Leu Asn Asp
195 200 205

Thr Asp Ser Ser Ala Ala Thr Lys Lys Thr Ala Ala Trp Asn Ser Gly
210 215 220

Thr Ser Thr Leu Thr Ile Thr Val Asn Ser Lys Lys Thr Lys Asp Leu
225 230 235 240

Val Phe Thr Lys Glu Asn Thr Ile Thr Val Gln Gln Tyr Asp Ser Asn
245 250 255

Gly Thr Lys Leu Glu Gly Ser Ala Val Glu Ile Thr Lys Leu Asp Glu
260 265 270

Ile Lys Asn Ala Leu Lys Trp Leu Ile Ile Leu Ala Ser Leu Leu Ala
275 280 285

Leu Ala Leu Ile Leu Ala Val Cys Ile Ala Val Gly Ser Gly Ala Arg
290 295 300

Ala Ser Val Leu Ser Gly Gly Glu Leu Asp Arg Trp Glu Lys Ile Arg
305 310 315 320

Leu Arg Pro Gly Gly Lys Lys Lys Tyr Lys Leu Lys His Ile Val Trp

-continued

```
                325                 330                 335

Ala Ser Arg Glu Leu Glu Arg Phe Ala Val Asn Pro Gly Leu Leu Glu
            340                 345                 350

Thr Ser Glu Gly Cys Arg Gln Ile Leu Gly Gln Leu Gln Pro Ser Leu
        355                 360                 365

Gln Thr Gly Ser Glu Glu Leu Arg Ser Leu Tyr Asn Thr Val Ala Thr
    370                 375                 380

Leu Tyr Cys Val His Gln Arg Ile Glu Ile Lys Asp Thr Lys Glu Ala
385                 390                 395                 400

Leu Asp Lys Ile Glu Glu Glu Gln Asn Lys Ser Lys Lys Lys Ala Gln
                405                 410                 415

Gln Ala Ala Ala Asp Thr Gly His Ser Asn Gln Val Ser Gln Asn Tyr
            420                 425                 430

Pro Ile Val Gln Asn Ile Gln Gly Gln Met Val His Gln Ala Ile Ser
        435                 440                 445

Pro Arg Thr Leu Asn Ala Trp Val Lys Val Val Glu Glu Lys Ala Phe
    450                 455                 460

Ser Pro Glu Val Ile Pro Met Phe Ser Ala Leu Ser Glu Gly Ala Thr
465                 470                 475                 480

Pro Gln Asp Leu Asn Thr Met Leu Asn Thr Val Gly Gly His Gln Ala
                485                 490                 495

Ala Met Gln Met Leu Lys Glu Thr Ile Asn Glu Glu Ala Ala Glu Trp
            500                 505                 510

Asp Arg Val His Pro Val His Ala Gly Pro Ile Ala Pro Gly Gln Met
        515                 520                 525

Arg Glu Pro Arg Gly Ser Asp Ile Ala Gly Thr Thr Ser Thr Leu Gln
    530                 535                 540

Glu Gln Ile Gly Trp Met Thr Asn Asn Pro Pro Ile Pro Val Gly Glu
545                 550                 555                 560

Ile Tyr Lys Arg Trp Ile Ile Leu Gly Leu Asn Lys Ile Val Arg Met
                565                 570                 575

Tyr Ser Pro Thr Ser Ile Leu Asp Ile Arg Gln Gly Pro Lys Glu Pro
            580                 585                 590

Phe Arg Asp Tyr Val Asp Arg Phe Tyr Lys Thr Leu Arg Ala Glu Gln
        595                 600                 605

Ala Ser Gln Glu Val Lys Asn Trp Met Thr Glu Thr Leu Leu Val Gln
    610                 615                 620

Asn Ala Asn Pro Asp Cys Lys Thr Ile Leu Lys Ala Leu Gly Pro Ala
625                 630                 635                 640

Ala Thr Leu Glu Glu Met Met Thr Ala Cys Gln Gly Val Gly Gly Pro
                645                 650                 655

Gly His Lys Ala Arg Val Leu Ala Glu Ala Met Ser Gln Val Thr Asn
            660                 665                 670

Ser Ala Thr Ile Met Met Gln Arg Gly Asn Phe Arg Asn Gln Arg Lys
        675                 680                 685

Ile Val Lys Cys Phe Asn Cys Gly Lys Glu Gly His Thr Ala Arg Asn
    690                 695                 700

Cys Arg Ala Pro Arg Lys Lys Gly Cys Trp Lys Cys Gly Lys Glu Gly
705                 710                 715                 720

His Gln Met Lys Asp Cys Thr Glu Arg Gln Ala Asn Phe Leu Gly Lys
                725                 730                 735

Ile Trp Pro Ser Tyr Lys Gly Arg Pro Gly Asn Phe Leu Gln Ser Arg
            740                 745                 750
```

```
Pro Glu Pro Thr Ala Pro Pro Glu Glu Ser Phe Arg Ser Gly Val Glu
        755                 760                 765

Thr Thr Thr Pro Pro Gln Lys Gln Glu Pro Ile Asp Lys Glu Leu Tyr
    770                 775                 780

Pro Leu Thr Ser Leu Arg Ser Leu Phe Gly Asn Asp Pro Ser Ser Gln
785                 790                 795                 800


<210> SEQ ID NO 37
<211> LENGTH: 2187
<212> TYPE: DNA
<213> ORGANISM: Artificial Sequence
<220> FEATURE:
<221> NAME/KEY: gene
<222> LOCATION: (1)..(2187)
<223> OTHER INFORMATION: Human TIM-3 protein fused to HIV GAG
      (TIM-3/GAGcop) including a human signal peptide (from TIM-3) full
      extracellular and TM sequences of human TIM-3, a GGGGS linker and
      the HIV GAG sequence devoid of myristoylation signal (nt)

<400> SEQUENCE: 37

atgttcagcc atctgccttt cgactgcgtg ctgctgctcc tgcttctgct gctgaccaga     60

tccagcgagg tcgagtacag agccgaagtg ggccagaatg cctacctgcc ttgcttctac    120

acaccagccg ctccaggcaa tctggtgcct gtgtgttggg gaaaaggcgc ctgtcctgtg    180

ttcgagtgcg gcaacgttgt gctgagaacc gacgagcggg acgtgaacta ctggaccagc    240

agatactggc tgaacggcga cttcagaaag ggcgacgtgt ccctgaccat cgagaatgtg    300

acactggccg acagcggcat ctactgctgc agaatccaga ttcctggcat catgaacgac    360

gagaagttca acctgaagct ggtcatcaag cccgccaaag tgacccctgc tcctaccaga    420

cagagagact tcaccgccgc ctttccacgg atgctgacca caagaggaca cggccctgcc    480

gagacacaga cacttggaag cctgcctgac atcaatctga cccagatcag caccctggcc    540

aacgagctga gagatagcag actggctaat gacctgagag acagcggcgc caccatccgg    600

atcggcatct atatcggagc cggcatctgt gccggactgg ccctggctct tattttcgga    660

gcactgatcg gaggcggcgg atccggcgct agagcttctg tgctgtctgg gggcgaactg    720

gatagatggg agaagatccg gctgcggcct ggcggcaaga agaagtacaa gctgaagcac    780

atcgtgtggg cctccagaga gctggaaaga ttcgccgtga accccggcct gctggaaacc    840

agcgagggct gcagacagat cctgggacag ctgcagccca gcctgcagac cggaagcgag    900

gaactgcgga gcctgtacaa caccgtggcc acactgtatt gcgtgcacca gcggatcgag    960

atcaaggaca ccaaagaggc cctggacaag atcgaggaag aacagaacaa gtctaagaag   1020

aaggcccagc aggctgccgc cgataccggc cactctaatc aggtgtccca gaactacccc   1080

atcgtgcaga acatccaggg ccagatggtg catcaggcca tcagccccag aaccctgaac   1140

gcctgggtca aggtggtgga agagaaggcc tttagccccg aagtgatccc catgttcagc   1200

gccctgtctg agggcgccac accccaggac ctgaacacca tgctgaacac agtgggcgga   1260

caccaggccg ccatgcagat gctgaaagag acaatcaacg aagaggccgc cgagtgggac   1320

agagtgcacc ctgtgcatgc cggacctatc gcccctggcc agatgagaga gcccagaggc   1380

tctgatatcg ccggcaccac cagcaccctg caggaacaga tcggctggat gaccaacaac   1440

ccccccatcc ccgtgggcga gatctacaag cggtggatca tcctgggcct gaacaagatt   1500

gtgcggatgt acagccccac ctccatcctg gacatccggc agggccccaa agagcccttc   1560

agagactacg tggaccggtt ctacaagacc ctgagagccg agcaggccag ccaggaagtg   1620
```

```
aagaattgga tgaccgagac actgctggtg cagaacgcca accccgactg caagaccatc   1680

ctgaaggccc tgggacctgc cgccaccctg gaagagatga tgacagcctg tcagggcgtg   1740

ggaggcccag gccacaaagc tagagtgctg gccgaggcca tgagccaagt gaccaactcc   1800

gccaccatta tgatgcagcg gggcaacttc cggaaccagc ggaagatcgt gaagtgcttc   1860

aactgcggca aagagggcca caccgcccgg aattgcagag cccccagaaa gaaaggctgc   1920

tggaagtgtg gaaaagaggg gcaccagatg aaggactgca ccgagcggca ggccaacttc   1980

ctgggcaaga tctggcctag ctacaagggc agacccggca atttcctgca gagcagaccc   2040

gagcctaccg cccctcccga ggaaagcttt agaagcggcg tggaaaccac cacccccccca   2100

cagaagcagg aacccatcga caaagagctg taccccctga ccagcctgag aagcctgttc   2160

ggcaacgacc ccagcagcca gtgatga                                        2187


<210> SEQ ID NO 38
<211> LENGTH: 727
<212> TYPE: PRT
<213> ORGANISM: Artificial Sequence
<220> FEATURE:
<221> NAME/KEY: PEPTIDE
<222> LOCATION: (1)..(727)
<223> OTHER INFORMATION: SEQ ID NO: 39 Human TIM-3 protein fused to HIV
      GAG (TIM-3/GAGcop) including a human signal peptide (from TIM-3)
      full extracellular and TM sequences of human TIM-3, a GGGGS
      linker and the HIV GAG sequence devoid of myristoylation signal
      (aa)

<400> SEQUENCE: 38

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Gly
    210                 215                 220

Gly Gly Gly Ser Gly Ala Arg Ala Ser Val Leu Ser Gly Gly Glu Leu
```

-continued

```
225                 230                 235                 240

Asp Arg Trp Glu Lys Ile Arg Leu Arg Pro Gly Gly Lys Lys Lys Tyr
                245                 250                 255

Lys Leu Lys His Ile Val Trp Ala Ser Arg Glu Leu Glu Arg Phe Ala
            260                 265                 270

Val Asn Pro Gly Leu Leu Glu Thr Ser Glu Gly Cys Arg Gln Ile Leu
        275                 280                 285

Gly Gln Leu Gln Pro Ser Leu Gln Thr Gly Ser Glu Glu Leu Arg Ser
    290                 295                 300

Leu Tyr Asn Thr Val Ala Thr Leu Tyr Cys Val His Gln Arg Ile Glu
305                 310                 315                 320

Ile Lys Asp Thr Lys Glu Ala Leu Asp Lys Ile Glu Glu Glu Gln Asn
                325                 330                 335

Lys Ser Lys Lys Lys Ala Gln Gln Ala Ala Ala Asp Thr Gly His Ser
            340                 345                 350

Asn Gln Val Ser Gln Asn Tyr Pro Ile Val Gln Asn Ile Gln Gly Gln
        355                 360                 365

Met Val His Gln Ala Ile Ser Pro Arg Thr Leu Asn Ala Trp Val Lys
    370                 375                 380

Val Val Glu Glu Lys Ala Phe Ser Pro Glu Val Ile Pro Met Phe Ser
385                 390                 395                 400

Ala Leu Ser Glu Gly Ala Thr Pro Gln Asp Leu Asn Thr Met Leu Asn
                405                 410                 415

Thr Val Gly Gly His Gln Ala Ala Met Gln Met Leu Lys Glu Thr Ile
            420                 425                 430

Asn Glu Glu Ala Ala Glu Trp Asp Arg Val His Pro Val His Ala Gly
        435                 440                 445

Pro Ile Ala Pro Gly Gln Met Arg Glu Pro Arg Gly Ser Asp Ile Ala
    450                 455                 460

Gly Thr Thr Ser Thr Leu Gln Glu Gln Ile Gly Trp Met Thr Asn Asn
465                 470                 475                 480

Pro Pro Ile Pro Val Gly Glu Ile Tyr Lys Arg Trp Ile Ile Leu Gly
                485                 490                 495

Leu Asn Lys Ile Val Arg Met Tyr Ser Pro Thr Ser Ile Leu Asp Ile
            500                 505                 510

Arg Gln Gly Pro Lys Glu Pro Phe Arg Asp Tyr Val Asp Arg Phe Tyr
        515                 520                 525

Lys Thr Leu Arg Ala Glu Gln Ala Ser Gln Glu Val Lys Asn Trp Met
    530                 535                 540

Thr Glu Thr Leu Leu Val Gln Asn Ala Asn Pro Asp Cys Lys Thr Ile
545                 550                 555                 560

Leu Lys Ala Leu Gly Pro Ala Ala Thr Leu Glu Glu Met Met Thr Ala
                565                 570                 575

Cys Gln Gly Val Gly Gly Pro Gly His Lys Ala Arg Val Leu Ala Glu
            580                 585                 590

Ala Met Ser Gln Val Thr Asn Ser Ala Thr Ile Met Met Gln Arg Gly
        595                 600                 605

Asn Phe Arg Asn Gln Arg Lys Ile Val Lys Cys Phe Asn Cys Gly Lys
    610                 615                 620

Glu Gly His Thr Ala Arg Asn Cys Arg Ala Pro Arg Lys Lys Gly Cys
625                 630                 635                 640

Trp Lys Cys Gly Lys Glu Gly His Gln Met Lys Asp Cys Thr Glu Arg
                645                 650                 655
```

```
Gln Ala Asn Phe Leu Gly Lys Ile Trp Pro Ser Tyr Lys Gly Arg Pro
            660                 665                 670

Gly Asn Phe Leu Gln Ser Arg Pro Glu Pro Thr Ala Pro Pro Glu Glu
        675                 680                 685

Ser Phe Arg Ser Gly Val Glu Thr Thr Thr Pro Pro Gln Lys Gln Glu
    690                 695                 700

Pro Ile Asp Lys Glu Leu Tyr Pro Leu Thr Ser Leu Arg Ser Leu Phe
705                 710                 715                 720

Gly Asn Asp Pro Ser Ser Gln
                725


<210> SEQ ID NO 39
<211> LENGTH: 1827
<212> TYPE: DNA
<213> ORGANISM: Artificial Sequence
<220> FEATURE:
<221> NAME/KEY: gene
<222> LOCATION: (1)..(1827)
<223> OTHER INFORMATION: SEQ ID NO: 40 MINGAG HXB2 cop (nt)

<400> SEQUENCE: 39

atgtggctgc agtctctgct gctgctgggc accgtggcct gcagcatcag catctggaac      60

cacaccacct ggatggaatg ggacagagag atcaacaact acaccagcct gatccactcc     120

ctgatcgagg aaagccagaa ccagcaggaa aagaacgaac aggaactgct ggaactggac     180

aagtgggcca gcctgtggaa ctggttcaac atcaccaact ggctgtggta catcaagctg     240

ttcatcatga tcgtgggcgg cctcgtgggc ctgagaatcg tgtttgccgt gctgagcatc     300

gtgaaccggg gaggcggagg atccggcgct agagcttctg tgctgtctgg gggcgaactg     360

gatagatggg agaagatccg gctgcggcct ggcggcaaga agaagtacaa gctgaagcac     420

atcgtgtggg cctccagaga gctggaaaga ttcgccgtga accccggcct gctggaaacc     480

agcgagggct gcagacagat cctgggacag ctgcagccca gcctgcagac cggaagcgag     540

gaactgcgga gcctgtacaa caccgtggcc acactgtatt gcgtgcacca gcggatcgag     600

atcaaggaca ccaaagaggc cctggacaag atcgaggaag aacagaacaa gtctaagaag     660

aaggcccagc aggctgccgc cgataccggc cactctaatc aggtgtccca gaactacccc     720

atcgtgcaga acatccaggg ccagatggtg catcaggcca tcagccccag aaccctgaac     780

gcctgggtca aggtggtgga agagaaggcc tttagccccg aagtgatccc catgttcagc     840

gccctgtctg agggcgccac accccaggac ctgaacacca tgctgaacac agtgggcgga     900

caccaggccg ccatgcagat gctgaaagag acaatcaacg aagaggccgc cgagtgggac     960

agagtgcacc ctgtgcatgc cggacctatc gcccctggcc agatgagaga gcccagaggc    1020

tctgatatcg ccggcaccac cagcaccctg caggaacaga tcggctggat gaccaacaac    1080

ccccccatcc ccgtgggcga gatctacaag cggtggatca tcctgggcct gaacaagatt    1140

gtgcggatgt acagccccac ctccatcctg gacatccggc agggccccaa agagcccttc    1200

agagactacg tggaccggtt ctacaagacc ctgagagccg agcaggccag ccaggaagtg    1260

aagaattgga tgaccgagac actgctggtg cagaacgcca accccgactg caagaccatc    1320

ctgaaggccc tgggacctgc cgccaccctg gaagagatga tgacagcctg tcagggcgtg    1380

ggaggcccag gccacaaagc tagagtgctg gccgaggcca tgagccaagt gaccaactcc    1440

gccaccatta tgatgcagcg gggcaacttc cggaaccagc ggaagatcgt gaagtgcttc    1500

aactgcggca aagagggcca caccgcccgg aattgcagag cccccagaaa gaaaggctgc    1560
```

-continued

```
tggaagtgtg gaaaagaggg gcaccagatg aaggactgca ccgagcggca ggccaacttc    1620

ctgggcaaga tctggcctag ctacaagggc agacccggca atttcctgca gagcagaccc    1680

gagcctaccg cccctcccga ggaaagcttt agaagcggcg tggaaaccac caccccccca    1740

cagaagcagg aacccatcga caaagagctg taccccctga ccagcctgag aagcctgttc    1800

ggcaacgacc ccagcagcca gtgatga                                        1827
```

The invention claimed is:

1. A virus-like particle comprising a fusion protein which comprises from the N- to the C-terminus:

(a) a polypeptide of interest, or a functionally equivalent variant thereof, (b) a transmembrane domain, or a functionally equivalent variant thereof, and (c) a HIV gag polypeptide, or a functionally equivalent variant thereof wherein the HIV gag polypeptide or its functionally equivalent variant lacks myristoylation sequence; or wherein the transmembrane domain comprises (a) the transmembrane domain of (i) the HIV gp41 polypeptide, (ii) the human CD22 molecule, (iii) the human CD36 molecule, or (iv) the human CD44 molecule; (b) the R696A mutant of HIV-1 Env; or (c) the functionally equivalent variants of (a) and (b).

2. A fusion protein according to claim 1, which comprises from the N- to the C-terminus:

(a) a polypeptide of interest, or a functionally equivalent variant thereof, (b) a transmembrane domain, or a functionally equivalent variant thereof, and (c) an HIV gag polypeptide, or a functionally equivalent variant thereof.

3. A polynucleotide encoding a fusion protein according to claim 2.

4. The polynucleotide according to claim 3 comprising sequence SEQ ID NO: 9 and/or comprising a sequence which sequence is codon-optimized for expression in human beings, companion or farm animals.

5. A vector comprising a polynucleotide according to claim 3.

6. A host cell comprising a fusion protein according to claim 2, a polynucleotide encoding the fusion protein or a vector comprising the polynucleotide.

7. A method for preparing a virus-like particle loaded with a polypeptide of interest comprising the steps of:

(a) expressing in a cell a fusion protein according to claim 2 and (b) recovering the VLPs from the extracellular medium.

8. A pharmaceutical composition comprising a therapeutically effective amount of the virus-like particle according to claim 1.

9. An immunogenic or vaccine composition comprising a therapeutically effective amount of the virus-like particle according to claim 1.

10. The immunogenic or vaccine composition according to claim 9 wherein composition is essentially free from aluminum phosphate.

11. A method for the treatment or prevention of a disease caused by a pathogen or a tumor in a subject, wherein the pathogen or tumor contain the polypeptide of interest or a region thereof, preferably the polypeptide of interest is an HIV polypeptide and the infection is an HIV infection, and more preferably the HIV polypeptide comprises the membrane proximal external region of gp41 or functionally equivalent variant thereof, preferably wherein the subject is previously treated with a conjugate comprising the polypeptide of interest forming part of the fusion protein coupled to a carrier, preferably the carrier is KLH, the method comprising administering to the subject the fusion protein according to claim 2, a polynucleotide encoding the fusion protein, a vector comprising the polynucleotide, a virus-like particle comprising the fusion protein, or a pharmaceutical, immunogenic or vaccine composition comprising the fusion protein or the virus-like particle.

12. The virus-like particle according to claim 1, wherein the polypeptide of interest, transmembrane domain and HIV gag polypeptide, or their functionally equivalent variants, are joined by a linker, or a functionally equivalent variant thereof.

13. The virus-like particle according to claim 1 wherein the polypeptide of interest is immunogenic.

14. The virus-like particle according to claim claim 12 wherein the linker is selected from the group consisting of:

(a) a linker comprising glycine residues, (b) a linker comprising glycine residues and serine residues, (c) a linker comprising three glycine residues and one serine residue and (d) a linker comprising sequences SEQ ID NO: 23 or SEQ ID NO: 24.

15. The virus-like particle according to claim 1 wherein the polypeptide of interest comprises at least one polypeptide from a virus, bacteria, fungi, protozoa, parasite, allergen or tumor marker or a functionally equivalent variant thereof.

16. The fusion protein according to claim 15 wherein the polypeptide of interest derives from an HIV env protein or a product resulting from the processing of an HIV env protein, preferably the HIV env protein is HIV gp41.

17. The virus-like particle according to claim 16 wherein the polypeptide of interest comprises from the N-to the C-terminus:

(a) the heptad repeat 2 of the HIV gp41 polypeptide or a functionally equivalent variant thereof, and (b) the membrane proximal external region of the HIV gp41 polypeptide or functionally equivalent variant thereof.

18. The virus-like particle according to claim 16 comprising sequence SEQ ID NO: 28.

* * * * *